US011458119B2

(12) United States Patent
Liu et al.

(10) Patent No.: US 11,458,119 B2
(45) Date of Patent: Oct. 4, 2022

(54) AMORPHOUS AND A CRYSTALLINE FORM OF GENZ 112638 HEMITARTRATE AS INHIBITOR OF GLUCOSYLCERAMIDE SYNTHASE

(75) Inventors: Hanlan Liu, Lexington, MA (US); Chris Willis, Southborough, MA (US); Renu Bhardwaj, Ashland, MA (US); Jianmei Kochling, Wellesley, MA (US); Craig Siegel, Woburn, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 13/511,768

(22) PCT Filed: Nov. 24, 2010

(86) PCT No.: PCT/US2010/057952
§ 371 (c)(1),
(2), (4) Date: Jan. 24, 2013

(87) PCT Pub. No.: WO2011/066352
PCT Pub. Date: Jun. 3, 2011

(65) Prior Publication Data
US 2013/0137743 A1 May 30, 2013

Related U.S. Application Data

(60) Provisional application No. 61/264,748, filed on Nov. 27, 2009.

(51) Int. Cl.
*A61K 31/4025* (2006.01)
*C07D 405/06* (2006.01)
*A61K 45/06* (2006.01)
*C07D 319/16* (2006.01)

(52) U.S. Cl.
CPC .......... *A61K 31/4025* (2013.01); *A61K 45/06* (2013.01); *C07D 319/16* (2013.01); *C07D 405/06* (2013.01)

(58) Field of Classification Search
CPC .. A61K 31/4025; A61K 45/06; C07D 319/16; C07D 405/06
See application file for complete search history.

(56) References Cited

U.S. PATENT DOCUMENTS

| | | | |
|---|---|---|---|
| 4,755,520 A | 7/1988 | Schon et al. |
| 5,041,441 A | 8/1991 | Radin et al. |
| 5,302,609 A | 4/1994 | Shayman et al. |
| 5,387,593 A | 2/1995 | Mattson et al. |
| 5,472,969 A | 12/1995 | Platt et al. |
| 5,525,616 A | 6/1996 | Platt et al. |
| 5,631,394 A | 5/1997 | Wei et al. |
| 5,684,020 A | 11/1997 | Peglion et al. |
| 5,707,649 A | 1/1998 | Inokuchi et al. |
| 5,763,438 A | 6/1998 | Inokuchi et al. |
| 5,849,326 A | 12/1998 | Inokuchi et al. |
| 5,907,039 A | 5/1999 | Jinbo et al. |
| 5,916,911 A | 6/1999 | Shayman et al. |
| 5,945,442 A | 8/1999 | Shayman et al. |
| 5,952,370 A | 9/1999 | Shayman et al. |
| 5,972,928 A | 10/1999 | Chatterjee |
| 6,030,995 A | 2/2000 | Shayman et al. |
| 6,040,332 A | 3/2000 | Shayman et al. |
| 6,051,598 A | 4/2000 | Shayman et al. |
| 6,228,889 B1 | 5/2001 | Chatterjee |
| 6,255,336 B1 | 7/2001 | Shayman et al. |
| 6,335,444 B1 | 1/2002 | Jinbo et al. |

(Continued)

FOREIGN PATENT DOCUMENTS

| CN | 107445938 A | 12/2017 |
|---|---|---|
| EP | 0 126 974 A1 | 12/1984 |

(Continued)

OTHER PUBLICATIONS

Hurst et al., Analytica Chimica Acta, 337 (1997), 233-52.*
Campbell Roberts et al., J. Pharm. Biomed. Anal., 28 (2002) 1149-59.*
Chen et al., J. Pharm. Sci., (1999), v. 88, p. 1191-1200.*
Tiwari et al., J. Pharm. Biomed. Anal., 43 (2007) 865-72.*
Brittain (Polymorphism in Pharmaceutical Solids, vol. 95, 1999, Taylor & Francis, Harry G. Brittain (Ed.), 427 pp.).*

(Continued)

*Primary Examiner* — Robert H Havlin
(74) *Attorney, Agent, or Firm* — Morrison & Foerster LLP

(57) ABSTRACT

The hemitartrate salt of a compound represented by the following structural formula: (Formula I Hemitartrate), which may be used in pharmaceutical applications, are disclosed. Particular single crystalline forms of the Formula (I) Hemitartrate are characterized by a variety of properties and physical measurements. As well, methods of producing crystalline Formula (I) Hemitartrate, and using it to inhibit glucosylceramide synthase or lowering glycosphingolipid concentrations in subjects to treat a number of diseases, are also discussed. Pharmaceutical compositions are also described.

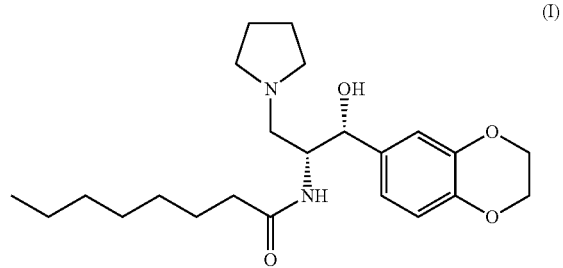

(I)

25 Claims, 15 Drawing Sheets

(56) References Cited

U.S. PATENT DOCUMENTS

| | | | |
|---|---|---|---|
| 6,436,987 B1 | 8/2002 | Allen et al. | |
| 6,511,979 B1 | 1/2003 | Chatterjee | |
| 6,569,889 B2 | 5/2003 | Shayman et al. | |
| 6,610,703 B1 | 8/2003 | Jacob et al. | |
| 6,660,749 B2 | 12/2003 | Butters et al. | |
| 6,855,830 B2* | 2/2005 | Hirth et al. | 548/526 |
| 6,890,949 B1 | 5/2005 | Shayman et al. | |
| 6,916,802 B2 | 7/2005 | Shayman et al. | |
| 6,977,723 B2 | 12/2005 | Lemmo et al. | |
| 7,148,251 B2 | 12/2006 | Shayman | |
| 7,196,205 B2 | 3/2007 | Siegel et al. | |
| 7,253,185 B2 | 8/2007 | Shayman et al. | |
| 7,265,228 B2 | 9/2007 | Hirth et al. | |
| 7,335,681 B2 | 2/2008 | Shayman | |
| 7,615,573 B2 | 11/2009 | Siegel et al. | |
| 7,674,935 B2 | 3/2010 | Levi et al. | |
| 7,763,738 B2 | 7/2010 | Hirth et al. | |
| 8,138,353 B2 | 3/2012 | Hirth et al. | |
| 8,586,610 B2 | 11/2013 | Wolfgang et al. | |
| 8,779,163 B2 | 7/2014 | Hirth et al. | |
| 8,933,088 B2 | 1/2015 | Selbo | |
| 8,962,654 B2 | 2/2015 | Beadle et al. | |
| 9,006,270 B2 | 4/2015 | Gallou et al. | |
| 9,018,243 B2 | 4/2015 | Muller et al. | |
| 9,546,161 B2 | 1/2017 | Hirth et al. | |
| 10,888,547 B2 | 1/2021 | Peterschmitt | |
| 2002/0198240 A1 | 12/2002 | Shayman et al. | |
| 2003/0050299 A1 | 3/2003 | Hirth et al. | |
| 2003/0073680 A1 | 4/2003 | Shayman et al. | |
| 2003/0083485 A1 | 5/2003 | Milos et al. | |
| 2004/0043457 A1 | 3/2004 | Schumacher et al. | |
| 2004/0220211 A1 | 11/2004 | Aronhime et al. | |
| 2004/0260099 A1 | 12/2004 | Shayman | |
| 2005/0032070 A1 | 2/2005 | Raimundo et al. | |
| 2005/0222244 A1 | 10/2005 | Siegel et al. | |
| 2005/0239862 A1 | 10/2005 | Shayman et al. | |
| 2005/0272721 A1* | 12/2005 | Keltjens | C07D 495/04 514/220 |
| 2006/0217560 A1 | 9/2006 | Shayman | |
| 2007/0072916 A1 | 3/2007 | Shayman | |
| 2007/0088082 A1* | 4/2007 | Aronhime | C07C 51/43 514/490 |
| 2007/0203223 A1 | 8/2007 | Siegel et al. | |
| 2008/0058514 A1 | 3/2008 | Hirth et al. | |
| 2008/0102541 A1 | 5/2008 | Kang et al. | |
| 2008/0137214 A1 | 6/2008 | Su et al. | |
| 2008/0293946 A1* | 11/2008 | Cheng | C07D 471/04 546/121 |
| 2009/0001773 A1 | 1/2009 | Leopold | |
| 2009/0307179 A1 | 12/2009 | Colby et al. | |
| 2012/0296088 A1 | 11/2012 | Hirth et al. | |
| 2016/0120842 A1 | 5/2016 | Liu et al. | |
| 2016/0166542 A1 | 6/2016 | Liu et al. | |
| 2021/0369672 A1 | 12/2021 | Liu et al. | |
| 2021/0393590 A1 | 12/2021 | Liu et al. | |

FOREIGN PATENT DOCUMENTS

| | | | |
|---|---|---|---|
| EP | 0 765 865 A1 | 4/1997 | |
| EP | 1 384 719 A1 | 1/2004 | |
| EP | 2504332 B1 | 6/2014 | |
| JP | 9-169664 A | 6/1997 | |
| JP | 9-216856 A | 8/1997 | |
| JP | 10-338636 A | 12/1998 | |
| JP | 10324671 A | 12/1998 | |
| JP | 2003335776 A | 11/2003 | |
| JP | 2005/535665 A | 11/2005 | |
| WO | WO-97/10817 A1 | 3/1997 | |
| WO | WO-1998/030883 A2 | 7/1998 | |
| WO | WO-1998/030883 A3 | 10/1998 | |
| WO | WO-98/52553 A1 | 11/1998 | |
| WO | WO-01/04108 A1 | 1/2001 | |
| WO | WO-02/062777 A2 | 8/2002 | |
| WO | WO-03/008399 A1 | 1/2003 | |
| WO | WO-2004/004702 A2 | 1/2004 | |
| WO | 2006/053043 A2 | 5/2006 | |
| WO | WO-2006/053043 A2 | 5/2006 | |
| WO | WO 2006053043 * | 5/2006 | A61K 31/395 |
| WO | WO-2007/134086 A2 | 11/2007 | |
| WO | WO-2008/068487 A1 | 6/2008 | |
| WO | WO-2008/121826 A2 | 10/2008 | |
| WO | WO-2008/134628 A2 | 11/2008 | |
| WO | 2008/150486 A2 | 12/2008 | |
| WO | 2009/117150 A2 | 9/2009 | |
| WO | 2011/066352 A1 | 6/2011 | |
| WO | 2011064171 A2 | 6/2011 | |
| WO | 2011064352 A1 | 6/2011 | |
| WO | 2011064474 A1 | 6/2011 | |
| WO | WO-2018/193090 A2 | 10/2018 | |

OTHER PUBLICATIONS

Morissette et al. (Advanced Drug Delivery Reviews 56 (2004) 275-300).*

US Pharmacopeia (X-ray diffraction; in US Pharmacopeia 29, Chapter 941 (2013)).*

Ivanisevic ("Uses of X-ray Powder Diffraction in the Pharmaceutical Industry" in Pharmaceutical Science Encyclopedia (2010), p. 1-42).*

Berge et al., J. Pharm. Sci., (1977) v. 66, No. 1, p. 1-19.*

Paulekuhn et al., J. Med. Chem. (2007), 50, 6665-6672).*

Registry Entry 928659-70-5 Entered STN: Mar. 29, 2007 for Eliglustat tartrate, Genz-112638.*

FDA Center for Drug Evaluation and Research, Application 205494Orig1s000, dated Aug. 19, 2014, 20 pages.*

"IUPAC", A Guide to IUPAC Nomenclature of Organic Compounds, "Salts and esters" (Recommendations 1993), 1993, Blackwell Scientific publications, reproduced by ACD at https://www.acdlabs.com/iupac/nomenclature/93/r93_511.htm , 4 pages provided.*

Zhao et al. (Diabetes, v. 56, May 2007, p. 1210-1218).*

Abdel-Magid, A., et al., "Metal-Assisted Aldol Condensation of Chiral α-Halogenated Imide Enolates: A Stereocontrolled Chiral Epoxide Synthesis," J. Am. Chem. Soc., 108: 4595-4602 (1986).

Abe, A., et al., "Improved Inhibitors of Glucosylceramide Synthase," J. Biochem., 111: 191-196 (1992).

Abe, A., et al., "Induction of Glucosylceramide Synthase by Synthase Inhibitors and Ceramide," Biochim. Biophys. Acta, 1299:333-341 (1996).

Abe, A., et al., "Metabolic Effects of Short-Chain Ceramide and Glucosylceramide on Sphingolipids and Protein Kinase C," Eur. J. Biochem., 210: 765-773 (1992).

Abe, A., et al., "Structural and stereochemical studies of potent inhibitors of glucosylceramide synthase and tumor cell growth," J. of Lipid Research, 36: 611-621 (1995).

Alker, D., et al., "Application of Enantiopure Templated Azomethine Ylids to β-Hydroxy-α-amino Acid Synthesis," Tetrahedron: 54: 6089-6098 (1998).

Alon, R., et al., "Glycolipid Ligands for Selectins Support Leukocyte Tethering and Rolling Under Physiologic Flow Conditions," J. Immunol., 154: 5356-5366 (1995).

Ames, Bruce N., "Assay of Inorganic Phosphate, Total Phosphate and Phosphatases," Methods Enzymol., 8: 115-118 (1966).

Bielawska, A., et al., "Ceramide-Mediated Biology: Determination of Structural and Stereospecific Requirements Through the Use of N-Acyl-Phenylaminoalcohol Analogs," J. Biol. Chem., 267: 18493-18497 (1992).

Bielawska, A., et al., "Modulation of Cell Growth and Differentiation by Ceramide," FEBS Letters, 307(2): 211-214 (1992).

Blobe, G. C., et al., "Regulation of Protein Kinase C and Role in Cancer Biology," Cancer Metastasis Rev., 13:411-431 (1994).

Brenkert, A., et al., "Synthesis of Galactosyl Ceramide and Glucosyl Ceramide by Rat Brain: Assay Procedures and Changes with Age," Brain Res., 36: 183-193 (1972).

Carson, K.G., et al., "Studies on Morpholinosphingolipids: Potent Inhibitors of Glucosylceramide Synthase," Tetrahedron Letters, 35(17):2659-2662 (1994).

(56) References Cited

OTHER PUBLICATIONS

Dellaria, Jr., J.F., et al., "Enantioselective Synthesis of α-Amino Acid Derivatives via the Stereoselective Alkylation of a Homochiral Glycine Enolate Synthon," J. Org. Chem., 54: 3916-3926 (1989).
Evans, D. A., et al., "Stereoselective Aldol Condensations Via Boron Enolates," J. Am. Chem. Soc., 103:3099-3111 (1981).
Felding-Habermann, B., et al., "A Ceramide Analog Inhibits T Cell Proliferative Response Through Inhibition of Glycosphingolipid Synthesis and Enhancement of N, N-Dimethylsphingosine Synthesis," Biochemistry, 29: 6314-6322 (1990).
Gatt, S., et al., "Assay of Enzymes of Lipid Metabolism With Colored and Fluorescent Derivatives of Natural Lipids," Meth. in Enzymol., 72: 351-375 (1981).
Hakomori, S., "New Directions in Cancer Therapy Based on Aberrant Expression of Glycosphingolipids: Anti-Adhesion and Ortho-Signaling Therapy," Cancer Cells, 3(12): 461-470 (1991).
Harwood, L.M., et al., "Asymmetric Cycloadditions of Aldehydes to Stabilized Azomethine Ylids: Enantiocontrolled Construction of β-Hydroxy-α-amino acid Derivitives," Tetrahedron: Asymmetry, 3(9): 1127-1130 (1992).
Harwood, L.M., et al., "Double diastereocontrol in the synthesis of enantiomerically pure polyoxamic acid," Chem. Commun., 2641-2642 (1998).
Högberg, T., et al., "Theoretical and Experimental Methods in Drug Design Applied on Antipsychotic Dopamine Antagonists." In Textbook of Drug Design and Development, pp. 55-91 (1991).
Hospattankar, A. V., et al., "Changes in Liver Lipids After Administration of 2-Decanoylamino-3-Morpholinopropiophenone and Chlorpromazine," Lipids, 17(8): 538-543 (1982).
Inokuchi, J., et al., "Antitumor Activity: Via Inhibition of Glycosphingolipid Biosynthesis," Cancer Letters, 38: 23-30 (1987).
Inokuchi, J., et al., "Inhibition of Experimental Metastasis of Murine Lewis Lung Carcinoma by an Inhibitor of Glucosylceramide Synthase and Its Possible Mechanism of Action," Cancer Res., 50:6731-6737 (1990).
Inokuchi, J., et al., "Preparation of the active isomer of 1-phenyl-2-decanoylamino-3-morpholino-1-propanol, inhibitor of murine glucocerebroside synthetase," J. of Lipid Research, 28:565-571 (1987).
Jaffrézou, J., et al., "Inhibition of Lysosomal Acid Sphingomyelinase by Agents which Reverse Multidrug Resistance," Biochim. Biophys. Acta, 1266: 1-8 (1995).
Kalén, A., et al., "Elevated Ceramide Levels in GH4C1 Cells Treated with Retinoic Acid," Biochim. Biophys. Acta, 1125: 90-96 (1992).
Kopaczyk, K. C., et al., "In Vivo Conversions of Cerebroside and Ceramide in Rat Brain," J. Lipid Res., 6:140-145(1965).
Kurosawa, M., et al., "14C-Labeling of a Novel Atypical β-Adrenoceptor Agonist, SM-11044," Journal of Labelled Compounds and Radiopharmaceuticals, 38(3): 285-297 (1996).
Lee, L., et al., "Improved Inhibitors of Glucosylceramide Synthase," J. Biol. Chem., 274(21): 14662-14669(1999).
Mitchell, S.A., et al., "Glycosyltransferase Inhibitors: Synthesis of D-threo-PDMP, L-threo-PDMP, and Other Brain Glucosylceramide Synthase Inhibitors from D- or L-Serine," J. Org. Chem., 63: 8837-8842 (1998).
Nakamura, K., et al., "Coomassie Brilliant Blue Staining of Lipids on Thin-Layer Plates," Anal. Biochem., 142: 406-410 (1984).
Nicolaou, K.C., et al., "A Practical and Enantioselective Synthesis of Glycosphingolipids and Related Compounds. Total Synthesis of Globotriaosylceramide (Gb3)," J. Am. Chem. Soc., 110:7910-7912(1988).
Nishida, A., et al., "Practical Synthesis of threo-(1S, 2S)- and erythro-(1R, 2S)-1-Phenyl-2-palmitoylamino-3-morpholino-1-propanol (PPMP) from L-Serine," Synlett, 389-390 (1998).
Ogawa, S., et al., "Synthesis and Biological Evaluation of Four Stereoisomers of PDMP-Analogue, N-(2-Decylamino-3-Hydroxy-3-Phenylprop-1-YL)-β-Valienamine, and Related Compounds," Bioorganic & Medicinal Chemistry Letters, 7(14):1915-1920 (1997).

Preiss, J., et al., "Quantitative Measurement of sn-1,2-Diacylglycerols Present in Platelets, Hepatocytes, and ras- and sis-Transformed Normal Rat Kidney Cells," J. Biol. Chem., 261(19): 8597-8600 (1986).
Radin, N. S., "Killing Cancer Cells by Poly-drug Elevation of Ceramide Levels, A Hypothesis Whose Time Has Come?," Eur. J. Biochem. 268(2): 193-204 (2001).
Radin, N. S., et al., "Metabolic Effects of Inhibiting Glucosylceramide Synthesis with PDMP and Other Substances." In Advances in Lipid Research; Sphingolipids, Part B., R. M. Bell et al., Eds. (San Deigo: Academic Press), 26:183-213 (1993).
Radin, N. S., et al., "Ultrasonic Baths as Substitutes for Shaking Incubator Baths," Enzyme, 45:67-70 (1991).
Radin, N. S., et al., "Use of an Inhibitor of Glucosylceramide Synthesis, D-1-Phenyl-2-decanoylamino-3-morpholino-1-propanol," In NeuroProtocols: A Companion to Methods in Neurosciences, S. K. Fisher et al., Eds., (San Diego: Academic Press) 3:145-155 (1993).
Rosenwald, A. G., et al., "Effects of the Glucosphingolipid Synthesis Inhibitor, PDMP, on Lysosomes in Cultured Cells," J. Lipid Res., 35:1232-1240 (1994).
Rosenwald, A. G., et al., "Effects of a Sphingolipid Synthesis Inhibitor on Membrane Transport Through the Secretory Pathway," Biochemistry, 31: 3581-3590 (1992).
Shayman, J. A., et al., "Glucosphingolipid Dependence of Hormone-Stimulated Inositol Trisphophate Formation," J. Biol. Chem., 265(21): 12135-12138 (1990).
Shayman, J. A., et al., "Modulation of Renal Epithelial Cell Growth by Glucosylceramide: Association with Protein Kinase C, Sphingosine, and Diacylglycerol," J. Biol. Chem., 266(34):22968-22974(1991).
Shukla, A., et al., "Metabolism of D-[$^3$H]threo-1-phenyl-2-decanoylamino-3-morpholino-1-propanol, an inhibitor of glucosylceramide synthesis and the synergistic action of an inhibitor of microsomal momooxygenase," J. of Lipid Research, 32:713-722 (1991).
Shukla, G. S., et al., "Glucosylceramide Synthase of Mouse Kidney: Further Characterization with an Improved Assay Method," Arch. Biochem. Biophys., 283(2): 372-378 (1990).
Shukla, G., et al., "Rapid Kidney Changes Resulting From Glycosphingolipid Depletion by Treatment with a Glucosyltransferase Inhibitor," Biochim. Biophys. Acta, 1083: 101-108 (1991).
Skehan, P., et al., "New Colorimetric Cytotoxicity Assay for Anticancer-Drug Screening," J. Natl. Cancer Inst., 82(13): 1107-1112 (1990).
Strum, J. C., et al., "1-β-D-Arabinofuranosylcytosine Stimulates Ceramide and Diglyceride Formation in HL-60 Cells," J. Biol. Chem., 269(22): 15493-15497 (1994).
Svensson, M., et al., "Epithelial Glucosphingolipid Expression as a Determinant of Bacterial Adherence and Cytokine Production," Infect. Immun., 62(10): 4404-4410 (1994).
Tang, W., et al., "Phorbol Ester Inhibits 13-Cis-Retinoic Acid-Induced Hydrolysis of Phosphatidylinositol 4,5-Biophosphate in Cultured Murine Keratinocytes: A Possible Negative Feedback Via Protein Kinase C-Activation," Cell Bloch. Funct., 9: 183-191 (1991).
Uemura, K., et al., "Effect of an Inhibitor of Glucosylceramide Synthesis on Cultured Rabbit Skin Fibroblasts," J. Biochem., (Tokyo) 108(4): 525-530 (1990).
Vunnam, R.R., et al., "Analogs of Ceramide That Inhibit Glucocerebroside Synthetase in Mouse Brain," Chemistry and Physics of Lipids, L.D. Bergelson, et al., eds. (Elsevier/North-Holland Scientific Publishers Ltd.), 26: 265-278 (1980).
Wong, C-H., et al., "Synthesis and Evaluation of Homoazasugars as Glycosidase Inhibitors," J. Org. Chem., 60: 1492-1501, (1995).
Zador, I. Z., et al., "A Role for Glycosphingolipid Accumulation in the Renal Hypertrophy of Streptozotocin-Induced Diabetes Mellitus," J. Clin. Invest., 91: 797-803 (1993).
Ziche, M., et al., "Angiogenesis Can be Stimulated or Repressed in In Vivo by a Change in GM3:GD3 Ganglioside Ratio," Lab. Invest., 67(6): 711-715 (1992).
Abe, A., et al., "Reduction of Globotriasylceramide in Fabry disease mice by substrate deprivation", J. Clin. Invest. 105(11): 1563-1571, Jun. 2000.
Jimbo, M., et al., "Development of a New Inhibitor of Glucosylceramide Synthase", J. Biochem. 127(3), 485-91, (2000).

(56) References Cited

OTHER PUBLICATIONS

Miura, T., et al., "Synthesis and Evaluation of Morpholino and Pyrrolidinosphingolipids as Inhibitors of Glucosylceramide Synthase", Bioorganic and Medicinal Chemistry, (6) 1481-1489 (1998).
Zhao et al., Diabetes, vol. 56, May 2007, pp. 1210-1218.
McEachern et al., "A Specific and Potent Inhibitor of Glucosylceramide Synthase for Substrate Inhibition therapy of Gaucher Disease", Molecular Genetics and Metabolism, 91, pp. 259-267 (2007).
Chemical Abstract, American Chemical Society, Science IP Order 3026454, Registry No. 928659-70-5, Registry Date: Mar. 29, 2007.
Morissette et al., "High-throughput crystallization: polymorphs, salts, co-crystals and solvates of pharmaceutical solids" Advanced Drug Delivery Reviews, Amsterdam, vol. 56, No. 3, 2004, pp. 275-300.
E.R.K. Morris, "Structural aspects of hydrates and solvates" in "Polymorphism in Pharmaceutical Solids", Ed. H.G. Brittain, Marcel Dekker, New York 1999, pp. 125-181.
Michael E. Aulton, "Pharmacy. The science of the design of pharmaceutical forms", 2nd Ed. 2004, pp. 1-9.
Byrn S., Pharmaceutical Solids: A strategic Approach in Regulatory Considerations, Pharmaceutical Research, 12(7):945-954 (1995).
Carla MR., Crystalline Polymorphism of Organic Compounds, Topics in Current Chemistry, 198:163-208(1998).
Genzyme, Clinical Trial NCT00891202, A Study of Eliglustat Tartrate (Genz-112638) in Patients With Gaucher Disease (ENGAGE), Apr. 30, 2009, downloaded from the internet, http://clinicaltrials.gov/ct2/show/study/NCT00891202?show_locs=Y#locn, pp. 1-6.
"Substance Name: Eliglustat tartrate [USAN]" http://chem.sis.nlm.nih.gov/chemidplus/rn/928659-707-5, Oct. 20, 2014.
Bavin, Mike, "Polymorphism in Process Development", Chemistry & Industry, 527-529, 1989.
Byrn et al., "Pharmaceutical Solids: A strategic Approach to Regulatory Considerations", Pharmaceutical Research, vol. 12, No. 7, 945-954, 1995.
Clinical Trial Information on Eliglustat, derived from ClinicalTrials.gov: https://clinicaltrials.gov/ct2/results?term=eliglustat&Search=Search.
Eller G. Mark, Chapter 4, Phase I, II, and III FDA Submission, in "Pharmacokinetics in Drug Discovery and Development", edited by Ronal D. Schoenwald, CRC Press, pp. 73-96, 2002.
EMEA, "Public summary of positive opinion for orphan designation", Committee for Orphan Medicinal Products, pp. 1-5, Jul. 1, 2008.
EMEA, "Guideline on the chemistry of new active substances", Committee for Proprietary Medicinal Products (CPMP), 1-13, Dec. 17, 2003.
EMEA, ICH Topic Q 6 A, Specifications: Test Procedures and Acceptance Criteria for New Drug Substances and New Drug Products: Chemical Substances; May 2000, published 2006.
Excerpt from IUPAC nomenclature in R-5.7.4 (salts and esters), www.acdlabs.com, last accessed on Oct. 2, 2014.
Experiment 13, Solubility Product of Potassium Acid Tartrate, pp. 1-8, Jun. 6, 2004.
FDA, Centre for Drug Evaluation and Research, "Summary Review for Regulatory Action on application No. 205494Orig1s00", Cerdelga(eliglustat tartrate), 1-20, Aug. 19, 2014.
Hirayama, Reimei, Handbook on the Preparation of Organic Compound Crystals, p. 11 and p. 57, 2008.
Information on Clinical Trial NCT00358150, derived from Clinical Trials.gov Archive, 1-3, dated Jun. 22, 2008.
Rowe et al., "Handbook of Pharmaceutical Excipients", Pharmaceutical Press, 5th Edition, pp. v-viii, 2006.
Search results for clinical studies with relevant date of Jul. 1, 2008 or before and Gaucher disease.
Vidal, Le Dictionnaire, 81e Édition, monographies de spécialités pharmaceutiques. Cover page and p. 2279, 2005.
Butters, T. "Pharmacotherapeutic strategies using small moleucles for the treatment of glycolipid lysosomal storage disorders" Expert Opinion on Pharmacotherapy, 8(4):427-435 (2007).
Platt et al. "Treating lysosomal storage disorders: Current practice and future prospects", Biochemica et biophysica Acta 1793: 737-745 (2009).
Capablo et al. "Neurologic Improvement in a Type 3 Gaucher Disease Patient Treated with Imiglucerase/Miglustat Combination", Epilepsia 48(7):1406-1408 (2007).
Hollack et al. "Novel therapeutic targets for the treatment of Fabry disease", Expert Opinion on Therpauetic Targets, 11(6):821-833 (2007).
Zanger et al. "Cytochrome P450 2D6:overview and update on pharmacology, genetics, biochemistry", Naunyn-Schmiedeberg's Arch Pharmacol, 369:23-37 (2004).
Winjnen et al. "Review article: the prevalence and clinical relevance of cytochrome P450 polymorphisms", Ailment Pharmacol Ther, 26(Suppl 2):211-219 (2007).
Peterschmitt, J. et al., "102. Genz-112638, an investigation oral treatment for Gaucher disease type 1: Preliminary Phase 2 clinical trial results," Molecular Genetics and Metabolism, vol. 96, No. 2, pp. S34, 2009.
Shayman, J.A., "Eliglustat Tartrate: Glucosylceramide Synthase Inhibitor Treatment of Type 1 Gaucher Disease," Drugs of the Future, vol. 35, No. 8, pp. 613-620, 2010.
McMurry, J. et al., Organic Chemistry, vol. 1, 3rd ed., pp. 274-279, 1994, translated by Mitsuaki Kodama et al., Tokyo Kagaku Dojin Co. LTD.
Warren, S., Program Learning Organic Synthetic Chemistry, pp. 16-19, 1979, translated by Yujirou Nomura, Kondasha LTD.
Takahashi, H. et al., Organic Synthesis of Targeted Compounds, pp. 6-7, 1981, Sankyo Shuppan Co.
Andersson et al., "N-Butyldeoxygalactonojirimycin: A More Selective Inhibitor of Glycosphingolipid Biosynthesis than N-Butyldeoxynojirimycin, In Vitro and In Vivo," Biochem Pharm, 59:821-829 (2000).
Andersson et al. "Inhibition of glycogen breakdown by imino sugars in vitro and in vivo," Biochem Pharm 67:697-705 (2004).
Doering et al. "Sphingolipid Activator Proteins Are Required for Epidermal Permeability Barrier Formation," J bio chem, 274(16):11038-11045 (1999).
Grabowski et al. "Enzyme Therapy in Type 1 Gaucher Disease: Comparative Efficacy of Mannose-terminated Glucocerebrosidase from Natural and Recombinant Sources," Ann Intern Med, 122:33-39 (1995).
McEachern et al. "AAV8-mediated expression of glucocerebrosidase ameliorates the storage pathology in the visceral organs of a mouse model of Gaucher disease," J Gene Med, 8:719-729 (2006).
Miller et al. "Analysis of the lipids of normal and Gaucher bone marrow," J Lab Clin Med, 127:353-358 (1996).
Overkleeft, et al. "Generation of Specific Deoxynojirimycin-type Inhibitors of the Non-lysosomal Glucosylceramidase," J bio chem, 273(41):26522-26527 (1998).
Van Patten et al. "Effect of mannose chain length on targeting of glucocerebrosidase for enzyme replacement therapy of Gaucher disease," Glycobiology, 17(5):467-478 (2007).
Wang et al. "Fabry disease:generation of a mouse model with a-galactosidase A deficiency," J Hum Genet, Abstract 1192, 59:A208 (1996).
Xu et al. "Viable Mouse Model of Acid b-Glucosidase Deficiency," Am J Path, 163(5):2093-2101 (2003).
Ziegler et al. "Correction of the Biochemical and Functional Deficits in Fabry Mice Following AAV8-mediated Hepatic Expression of a-galactosidase A," Mol Therapy, 15(3):492-500 (2007).
Aerts et al., "Pharmacological Inhibition of Glucosylceramide Synthase Enhances Insulin Sensitivity," Diabetes, 56:1341-1349 (2007).
Notice of Opposition to EP2504332 as filed by Sandoz AG with the EPO on Feb. 27, 2015.
Mulberg, A., Division Deputy Director Summary Review, FDA Center for Drug Evaluation and Research, Application Mo. 205494Orig1s000, dated Aug. 9, 2014, 18 pages.
IX. Evidence Presented, List of Publications, and Facts & Arguments by Kraus & Weisert as filed with the EPO in Dpposition to EP2504332 on Feb. 27, 2015.
Communication of a Notice of Opposition to EP2504332 to Applicant by the EPO, dated Mar. 10, 2015.

(56) References Cited

OTHER PUBLICATIONS

Communication of Notice(s) of Opposition and request to file observations, to Potter Clarkson LLP by EPO dated Apr. 15, 2015.
Notice of Further Opposition to Opponent(s), to Kraus & Weisert by EPO dated Apr. 15, 2015.
Auxiliary Request 1 included with Patentee's Observations filed by Mathys & Squire with the EPO in EP2504332 on Feb. 25, 2016, 4 pages.
Patentee's Observations as filed by Mathys & Squire with the EPO in EP2504332 on Feb. 25, 2016.
Assessment Report for Fablyn, Procedure No. EMEA/H/C/000977, European Medicines Agency, dated 2009 on front page, pp. 1/44-7/44 (included as D17 to Patentee's Observations as filed by Mathys & Squire with the EPO in EP2504332 on Feb. 25, 2016).
Assessment Report for Mirvaso, Procedure No. EMEA/H/C/002642/0000, European Medicines Agency, dated Dec. 19, 2013 on front page, pp. 1/107-10/107 (included as D18 to Patentee's Observations as filed by Mathys & Squire with the EPO in EP2504332 on Feb. 25, 2016).
Annex to the Opposition Communication from the EPO in EP2504332 dated May 31, 2016.
Auxiliary Request 3 (filed with Letter Regarding the Opposition Procedure filed by Mathys & Squire in EP2504332 on Sep. 7, 2016).
Auxiliary Request 4 (filed with Letter Regarding the Opposition Procedure filed by Mathys & Squire in EP2504332 on Sep. 7, 2016).
Auxiliary Request 5 (filed with Letter Regarding the Opposition Procedure filed by Mathys & Squire in EP2504332 on Sep. 7, 2016).
Auxiliary Request 2 (filed with Letter Regarding the Opposition Procedure filed by Mathys & Squire in EP2504332 on Sep. 7, 2016).
Directive 65/65/EEC of Jan. 26, 1965 on the approximation of provisions laid down by law, regulation or administrative action relating to medicinal products, OJ L No. 22 of 9.2. 1965. p. 369. (filed with Letter Regarding the Opposition Procedure filed by Mathys & Squire in EP2504332 on Sep. 7, 2016).
Regulation (EC) No. 141/2000 of the European Parliament and of the Council on orphan medicinal products, Dec. 16, 1999, from the Official Journal of the European Communities, Jan. 22, 2000, pp. L18/1-L18/5). (filed with Letter Regarding the Opposition Procedure filed by Mathys & Squire in EP2504332 on Sep. 7, 2016).
Recommendations on Elements required to support the medical plausibility and the assumption of significant benefit dr an orphan designation, European Medicines Agency, London, UK, dated on front page Mar. 2, 2010, pp. 1-8. (filed with Letter Regarding the Opposition Procedure filed by Mathys & Squire in EP2504332 on Sep. 7, 2016).
Curriculum Vitae of Dr. Craig S. Siegel, Scientific Director of Genzyme Corporation, 2pgs. (filed with Letter Regarding he Opposition Procedure filed by Mathys & Squire in EP2504332 on Sep. 7, 2016).
Annex to the Opposition Letter entitled "A Study Comparing the Chemical Reactivity of Eliglustate Hemitartrate in a Crystalline Form Versus an Amorphous Form" (filed with Letter Regarding the Opposition Procedure filed by Mathys & Squire in EP2504332 on Sep. 7, 2016).
Letter Regarding the Opposition Procedure filed by Mathys & Squire in EP2504332 on Sep. 7, 2016.
Reply to Patentee's Observations and the Opposition Division's Summons to attend Oral Proceedings in EP2504332 as filed in the EPO on Sep. 7, 2016.
Means of Redress, EPO Form 2019 11.12TRI (included with the Decision of the Opposition Division in EP2504332 dated Dec. 12, 2016), 2pgs.
Minutes of the Oral Proceedings (included with the Decision of the Opposition Division in EP2504332 dated Dec. 12, 2016), 4 pgs.
Interlocutory Decision in Opposition Proceedings (Decision of the Opposition Division in EP2504332 dated Dec. 12, 2016), 41 pgs.
Druckexemplar in Opposition Procedure (included with the Decision of the Opposition Division in EP2504332 dated Dec. 12, 2016), 45 pgs.

Benedetti, M.S. et al. (Jul. 15, 2009). "Drug Metabolism and Pharmacokinetics," *Drug Metabolism Reviews* 41(3):344-390.
Benjamin, E.R. (Jun. 2009, e-pub. Apr. 18, 2009). "The pharmacological chaperone 1-deoxygalactonojirimycin increases α-galactosidase A levels in Fabry patient cell lines," *J. Inherit Metab. Dis.* 32(3)424-440.
*Brimonidine Tartrate 0.2%W/V/EYE Drops* (PL 15872/0018) UKPAR, Medicines and Healthcare Products Regulatory Agency (MHRA), 23 pages.
*Catharanthine Hemitartrate* (CAS# 4168-17-6), obtained from <https://www.chemblink.com/products/4168-17-6.htm>, on Jan. 15, 2013, 2 pages.
Cerdelga® (Jun. 25, 2014). "NDA 205494 Eliglustat Tartrate (Cerdelga)," Office of Clinical Pharmacology Review Addendum, located at: <https://www.accessdata.fda.gov/drugsatfda_docs/nda/2014/205494Orig1s000ClinPharmR.pdf>, Reference ID 3611718, 276 pages.
Chang, G.W.M. et al. (1999). "The Physiological and Pharmacological Roles of Cytochrome P450 Isoenzymes," *Anaesthesia* 54:42-50.
CHANTIX® (revised, Jul. 2011). *Highlights of Prescribing Information,* 18 pages.
Chen, J. et al. (Mar. 22, 2018). "Prediction of a Lack of Effect of Eliglustat on a Sensitive Cyp3A Substrate Using Physiologically Based Pharmacokinetic Modeling," *American Society for Clinical Pharmacology and Therapeutics,* Abstracts of 2018 Annual Meeting Hilton Orlando, Orlando, FL, Mar. 21-24, 2018, 103(S1):S27, 3 pages, Abstract No. PI-049.
Chen, J. et al. (Mar. 23, 2018). "Physiologically Based Pharmacokinetic Modeling for Assessment of Eliglustat Interaction Potential with Cyp2d6 and Cyp3a Inhibitors," *American Society for Clinical Pharmacology and Therapeutics,* Abstracts of 2018 Annual Meeting Hilton Orlando, Orlando, FL, Mar. 21-24, 2018, 103(S1):S62, 3 pages, Abstract No. PII-027.
De Leon, J. et al. (2006). "The AmpliChip™CYP450 Genotyping Test, Integrating a New Clinical Tool," *Mol. Diag. Ther.* 10(3): 135-151.
Dulsat, C. et al. (2009). "Gaucher'S Disease," *Drugs of the Future* 34(2):147-149.
Emoto, C. et al. (Sep. 2007). "Approach to Predict the Contribution of Cytochrome P450 Enzymes to Drug Metabolism in the Early Drug-Discovery Stage: The Effect of the Expression of Cytochrome b5 with Recombinant P450 Enzymes," *Xenobiotica,* 37(9):986-999.
Food and Drug Administration (Mar. 2005). "Guidance for Industry Pharmacogenomic Data Submissions," *Brochure,* 29 pages.
Food and Drug Administration Eligustat Approval (Aug. 18, 2014). "Cross Discipline Team Leader Review," Center for Drug Evaluation and Research, *Brochure,* 56 pages.
Fowler, S. et al. (2017, e-pub. Feb. 1, 2017). "Progress in Prediction and Interpretation of Clinically Relevant Metabolic Drug-Drug Interactions: a Minireview Illustrating Recent Developments and Current Opportunities," *Curr Pharmacol Rep* 3:36-49.
Genzyme (2008). "Genetic Diseases," Brochure, p. 12, (1 page).
Genzyme (Jul. 30, 2009). "A Study of the Efficacy and Safety of Genz-112638 in Type 1 Gaucher Patients (NCT00358150)," ClinicalTrials.gov archive, 3 pages.
Genzyme (Nov. 26, 2009). "Clinical Trials by Genzyme Before the Priority Date," ClinicalTrials.gov, 1 page.
Genzyme (Nov. 3, 2009). "A Study of Genz-112638 in Patients With Gaucher Disease (Engage) (NCT00891202)," ClinicalTrials.gov archive, 3 pages.
Genzyme (Nov. 5, 2009). "A Study of Genz-112638 in Patients With Gaucher Disease Who Have Been Stabilized on Cerezyme (NCT00943111)," ClinicalTrials.gov archive, 3 pages.
GlaxoSmithKline Australia Pty Ltd. (Jul. 21, 1997). TAGAMET® (cimetidine) Product Information, *Brochure,* 11 pages.
Grant, D.J.W. (1999). "Theory and Origin of Polymorphism," Chapter 1 in *Polymorphism in Pharmaceutical Solids,* BRITTAIN, Harry G. ed., Taylor & Francis, Milford, New Jersey, pp. 1-10, 27 pages.
Guggenbuhl, P. (Mar. 2008, e-pub. Aug. 31, 2007). "Gaucher Disease," *Joint Bone Spine* 75(2):116-124.

(56) References Cited

OTHER PUBLICATIONS

Guillory, J.K. (1999). "Generation of Polymorphs, Hydrates, Solvates, and Amorphous Solids," Chapter 5 in *Polymorphism in Pharmaceutical Solids,* BRITTAIN, Harry G. ed., Taylor & Francis, Milford, New Jersey, pp. 183-219, 53 pages.

Haynes, D.A. et al. (Oct. 2005). "Occurrence of Pharmaceutically Acceptable Anions and Cations in the Cambridge Structural Database," *Journal of Pharmaceutical Sciences* 94(10):2111-2120.

*Ifenprodil Hemitartrate* (Cat. No. 0545) obtained from. <https://www.tocris.com/products/ifenprodil-hemitartrate_0545>, on Jan. 8, 2013, 2 pages.

Inokuchi, J. (1987). "Preparation of the Active Isomer of 1-phenyl-2-decannoylamino-3-morpholino-1-propanol, Inhibitor of Murine Glucocerebroside Synthesis," *J. of Lipid Research* 28:565-571.

Kirchheiner, J. et al. (2007, e-pub Oct. 4, 2016). "Clinical Implications of Pharmacogenetics of Cytochrome P450 Drug Metabolizing Enzymes," *Biochimica et Biophysica Acta* 1770(3):489-494.

Kukes, V. G. (2006). *Clinical Pharmacology,* 5$^{th}$ Edition, GEOTAR-Media Publishing Group, Russia Moscow, 154-159 (18 pages including translation).

Liu, X. et al. (Dec. 2007). "The Conduct of Drug Metabolism Studies Considered Good Practice (I): Analytical Systems and In Vivo Studies," *Current Drug Metabolism* 8(8):815-821.

McElroy et.al. (2000). "CYP2D6 Genotyping as as Alternative to Phenotyping for Determination of Metabolic Status in a Clincal Trial Setting", *AAPS Pharmsci* 2(4):Article 33, 11 pages, (http://www.pharmsci.org/).

NCT00358150. (Jun. 16, 2016). "A Study of The Efficacy and Safety Of Eliglustat Tartrate (Genz-112638) In Type 1 Gaucher Patients," *Clinical Trials.Gov,* located at <https://clinicaltrials.gov/ct2/home>, last visited on Jan. 26, 2017, 5 pages.

NCT00358150. (May 12, 2009). "A Study of The Efficacy and Safety of Eliglustat Tartrate (Genz-112638) In Type 1 Gaucher Patients," *Clinical Trials.Gov,* located at <https://clinicaltrials.gov/ct2/home>, last visited on Jan. 26, 2017, 3 pages.

Notice of Grounds of Appeal as filed by *Sandoz AG* et al. on Apr. 22, 2017, 40 pages.

Oesch, F. (Jul. 15, 2009). "Importance of Knowledge on Drug Metabolism for the Safe Use of Drugs in Humans," *Drug Metabolism Reviews* 41(3):298-300.

Ogilvie, B.W. et al. (2008). In Vitro Study of Drug-Metabolizing Enzymes, in *Drug-Drug Interactions, Second Edition,* Rodrigues, A.D., et al. eds., Informa Healthcare: New York, New York, p. 294, 3 pages.

Shebley, M. et al. (Jan. 9, 2018). "Physiologically Based Pharmacokinetic Model Qualification and Reporting Procedures for Regulatory Submissions: A Consortium Perspective," *Clin. Pharmacol. Ther.* 0(0):23 pages.

*Trimeprazine Hemitartrate Salt* (CAS# 4330-99-8), obtained from <https://www.scbt.com/scbt/product/trimeprazine-hemitartrate-salt-4330-99-8?requestFrom=search> on Jan. 15, 2013, 1 page.

*Tylosin Hemitartrates Salt Dihydrate Suppliers List,* obtained from <http://www.chemicalbook.com/ProductChemicalPropertiesCB3219287_EN.htm >, on Jan. 15, 2013, 1 page.

Wienkers, L. C. et al. (Oct. 2005). "Predicting In Vivo Drug Interactions From In Vitro Drug Discovery Data," *Nature Reviews* 4:825-833.

Yoshida, K. et al. (May 2017, e-pub. Jan. 11, 2017). "Impact of Physiologically Based Pharmacokinetic Models on Regulatory Reviews and Product Labels: Frequent Utilization in the Field of Oncology," *Clinical Pharmacology & Therapeutics* 101(5):597-602.

Yu, J. et al. (Dec. 2014). "Drug Disposition and Drug-Drug Interaction Data in 2013 FDA New Drug Applications: A Systematic Review," *Drug Metabolism and Disposition* 42:1991-2001.

Yu, J. et al. (Jan. 2016). "Key Findings from Preclinical and Clinical Drug Interaction Studies Presented in New Drug and Biological License Applications Approved by the Food and Drug Administration in 2014," *Drug Metabolism and Disposition* 44:83-101.

Yu, J. et al. (Jan. 2017). "What Can Be Learned from Recent New Drug Applications? A Systematic Review of Drug Interaction Data for Drugs Approved by the US FDA in 2015," *Drug Metabolism and Disposition* 45:86-108.

Zhao, P. (2016). "Application of Physiologically-based Pharmacokinetic Modeling to Support Dosing Recommendations—The US Food and Drug Administration Experience," EMA Workshop on PBPK Guideline, U.S. F.D.A, 14 pages.

Zhou, S-F. (2008). "Drugs Behave as Substrates, Inhibitors and Inducers of Human Cytochrome P450 3A4" *Current Drug Metabolism* 8(4):310-322.

Zisaki, A. et al. (2015). "Antihypertensive Drugs Metabolism: An Update to Pharmacokinetic Profiles and Computational Approaches," *Current Pharmaceutical Design* 21(6):806-822.

Cox, T.M. (2008). "Gaucher's Disease: A Model Disorder for Therapeutic Exploration of the Lysosome," in *Mechanisms of Disease: An Introduction to Clinical Science,* Second Edition, Tomlinson, S et al. eds., Cambridge University Press, New York, New York, pp. 42-68.

Lukina, E. et al. (Jun. 4-7, 2009). "GENZ-112638, An Investigational Oral Therapy for Gaucher Disease Type 1: Phase 2 Clinical Trial Results after One Year of Treatment," Haematologica 94(Suppl. 2): 41 (Abstract No. 0106).

Cox, T.M. (2008). "Medicinal Use of Iminosugars", in *Iminosugars: From Synthesis to Therapeutic Applications,* Compain, P. et al. eds., John Wiley & Sons, West Sussex, England, pp. 295-326.

EMEA "Annual Report of the European Medicines Agency 2007," (Published May 13, 2008) Annex 13, p. 115, 138 pages.

Patentee's Response to the Statement of Grounds of Appeal filed in European Patent No. 2 504 332 B1, on Sep. 13, 2017, 24 pages.

Peterschmitt, J. et al. (2009). "Genz-112638 for Gaucher Disease Type 1: Phase 2 Clinical Trial Results After 18 Months of Treatment," Blood 114:1349, 5 pages.

Reply to the Submissions of the Patentee (Genzyme Corporation) filed on behalf of Sandoz AG, for EP 2 504 332, on Oct. 24, 2018, 20 pages.

Abe, A. et al. (2000). "Glycophosphingolipid Depletion in Fabry Disease Lymphoblasts with Potent Inhibitors of Glucosylceramide Synthase," *Kidney Int.* 57:446-454.

Beedham, C. (1997). "The Role of non-P450 Enzymes in Drug Oxidation," *Pharm. World. Sci.* 19(6):255-263.

Clinical Trials, History of Changes for Study NCT00358150, "A Study of the Efficacy and Safety of Eliglustat Tartrate (Genz-112638) in Type 1 Gaucher Patients," 2 pages, last printed on Dec. 11, 2019, located at https://clinicaltrials.gov/ct2/history/NCT00358150, last visited on Dec. 19, 2019.

Clinical Trials, results for NCT00358150 from Jul. 27-31, 2006, "A Study of the Efficacy and Safety of Eliglustat Tartrate (Genz-112638) in Type 1 Gaucher Patients," 9 pages, last printed on Dec. 17, 2019, located at https://www.clinicaltrials.gov/ct2/history/NCT003581507V_2=View, last visited on Dec. 19, 2019.

Response to Communications Under Rules 161(1) and Rule 162 EPC to Communication dated Jul. 25, 2012: Letter and Amended Claims, filed Jan. 30, 2013 on behalf of Applicant Genzyme Corporation, 58 pages.

Evans, W.E. et al. (Oct. 15, 1999). "Pharmacogenomics: Translating Functional Genomics into Rational Therapeutics," *Science* 286:487-491.

European Office Action Communication Article 94(3) dated May 8, 2013, for Patent Application No. 107852899, filed Dec. 9, 2010, 3 pages.

FDA, "Back to Pharmacogenomics: Overview of the Genomics and Targeted Therapy Group" from Table of Pharmacogenomic Biomarkers in Drug Labeling, located at: https://www.fda.gov/drugs/science-research-drugs/table-pharmacogenomic-biomarkers-drug-labeling, last visited on Dec. 19, 2019, 38 pages.

Gould, P.L. (1986). "Salt Selection for Basic Drugs," *Int. J. Pharmaceutics* 33:201-217.

Kawaguchi, Y. et al. (2002). "Pharmaceuticals and Polymorphs, Drug and Crystal Polymorphism," *Journal of Human Environmental Engineering* 4(2):310-317. (Machine Translation).

Liu, A. et al. (2007). "Warfarin-Drug Interactions Among Older Adults," *Geriatrics Aging* 10(10):643-646.

(56) References Cited

OTHER PUBLICATIONS

Oshima, H. (2007). "Crystallization of Polymorphs and Pseudopolymorphs and its Control," *Pharm Stage* 6(10):48-53. (Machine Translation).
Peck, G.E. et al. (1989). "Tablet Formulation and Design", in Pharmaceutical Dosage Forms: Tablets, vol. 1, Second Edition, Revised and Expanded, Liebermann, H.A. et al. eds., Marcel Dekker Inc. New York, New York, U.S.A, pp. 105-109.
Pharmaceutical Investigation No. 568 (May 1, 2001). "New Drug Standards and Test Methods" from Ministry of Health, Labor and Welfare, 84 pages. (Machine Translation).
Rodriguez-Spong, B. et al. (Feb. 23, 2004). "General Principles of Pharmaceutical Solid Polymorphism: A Supramolecular Perspective," *Advanced Drug Delivery Reviews* 56(3):241-274.
Rowe, R.C. et al. (2006). "Colloidal Silicon Dioxide," in Handbook of Pharmaceutical Excipients, 5th edition, Rowe, R.C et al. eds., Pharmaceutical Press, Great Britain, UK, pp. 188-190, 12 pages.
Stahl, P.H. et al. eds. (2002). Handbook of Pharmaceuticals Salts, International Union of Pure and Applied Chemistry (IUPAC), Wiley Publishing House, Verlag Helvetica Chimica Acta Zurich, 376 pages.
Takata, N. (2007). "API Form Screening and Selection in Drug Discovery Stage," *Pharm Stage* 6(10):20-25. (Machine Translation).
Yamano, M. (Sep. 1, 2007). "Approach to Crystal Polymorph in Process Research of New Drug," *Journal of Synthetic Organic Chemistry* (Japan) 65(9):907-913. (Machine Translation).
Zhang, H. et al. (2007). "Reduction of Site-Specific CYP3A-Mediated Metabolism for Dual Angiotensin and Endothelin Receptor Antagonists in Carious in Vitro Systems and in Cynomolgus Monkeys," *Drug Metabolism and Disposition* 35(5):795-805.
Applicant's Response to IPRP dated Jan. 30, 2013 from EP Application No. EP2504332, 87 pages.
Belle, D. et al. (Jun. 1, 2008). "Genetic Factors in Drug Metabolism," Amer Family Physician 77(11):1553-1560.
Bertilson, L. et al. (Feb. 2002). "Molecular Genetics of CYP2D6: Clinical Relevance With Focus on Psychotropic Drugs," Br. J. Clin. Pharmacol. 53(2):111-122.
Bozina, N. et al. (Jun. 1, 2009). "Genetic Polymorphism of Metabolic Enzymes P450 (CYP) as a Susceptibility Factor for Drug Response, Toxicity, and Cancer Risk," Arh Hg Rada Toksikol 60(2):217-242.
EMC (Jan. 8, 2020). "Cerdelga 84 mg Hard Capsules," EMC, as retrieved from https://www.medicines.org.uk/emc/product/2615/smpc, 16 pages.
EPR (Dec. 12, 2009). "Drug Metabolism And Pharmacokinetics—An Overview," Eur Pharm Rev, 13 pages.
Gaedigk, A. et al. (Feb. 2008, e-pub Oct. 31, 2007). "The CYP2D6 Activity Score: Translating Genotype Information into a Qualitative Measure of Phenotype," Clinical Pharmacology and Therapeutics 83(2):234-242.
GENZYME (Feb. 20, 2009). "Study of Genzyme Oral Compound for Gaucher Disease Meets Primary Endpoint," ClinicalTrials.gov, Sanofi Press Release, 7 pages, as retrieved from https://www.sanofigenzyme.com/en/about-US/newsroom/archive/2009/2009-02-20-01-45-00.
Hoffmann-Laroche Ltd. "The CYP450 Gene Family and Drug Metabolism," ROCHE Diagnostics, Background Information, News Flash-Press Release, as retrieved on Mar. 17, 2017 from Wayback Machine, https://web.archive.org/web/20070317041808/http://www.roche.com:80/final_cyp_gene_family.pdf, 7 pages.
Ioannides, C. (Jun. 27, 2008). "Cytochromes P450: Role In The Metabolism and Toxicity of Drugs and Other Xenobiotics," Chapter 1 in Royal Society of Chemistry, pp. 15-24.
Ioannides, C. (Jun. 27, 2008). "Cytochromes P450: Role In The Metabolism and Toxicity of Drugs and Other Xenobiotics," Chapters in Royal Society of Chemistry, pp. 255-264.

Lukina, E. et al. (2009). "Latest Data on Genz-112638, an Investigational Oral Therapy for Type 1 Gaucher Disease Phase II Clinical Trial Results After 1 Year of Treatment," Clinical Therapeutics 31(C):S194-S195.
McEachern, K. et al. (Nov. 20, 2007). "24 Genz-112638: A Novel Orally Available Ceramide-Based Inhibitor of Glucosylceramide Synthase for Treating Gaucher Disease," Mol Gen & Met 92(4):S17.
NIH (Sep. 17, 2009). "A Study of Genz-112638 in Patients With Gaucher Disease Who Have Been Stabilized on Cerezyme (ENCORE)," Clinicaltrials.gov Study NCT00943111,5 pages, as retrieved from https://clinicaltrials.gov/ct2/history/NCT00943111?V_5=View#StudyPageTop, XP055378019.
Notice of European Opposition for European Patent No. 3133070, dated May 13, 2020, Proprietor Genzyme Corporation, Opponent Teva Pharmaceutical Industries Ltd, 20 pages.
Notice of European Opposition for European Patent No. 3133070, dated May 14, 2020, Proprietor Genzyme Corporation, Opponent Accord Healthcare Ltd, 20 pages.
Notice of European Opposition for European Patent No. 3133070, dated May 14, 2020, Proprietor Genzyme Corporation, Opponent Hetero Labs Limited, 24 pages.
Peterschmitt, J. et al. (2008). "73. Preliminary Results of a Phase II Clinical Trial of Genz-112638 in Patients with Type I Gaucher Disease," Abstracts, Molecular Genetics and Metabolism 93:S32-S33.
Sharp, C.F. et al. (Jun. 1, 2009, e-pub Apr. 14, 2009). "CYP2D6 Genotype and Its Relationship With Metoprolol Dose, Concentrations and Effect In Patients With Systolic Heart Failure," The Pharmacogenomics Journal 9(3):175-184.
Van Schaik, R.H.N. (Apr. 3, 2008). "Dose Adjustments Based on Pharmacogenetics of CYP450 Enzymes," Chapter6 in The Communications and Publications Division (CPD) of the IFCC 19(1):42-47.
Zhou, S-F. et al. (2009). "Polymorphism of Human Cytochrome P450 Enzymes and Its Clinical Impact," Drug Met Rev 41(2):89-295.
Annex to the Opposition Communication from the EPO in EP3133070 dated May 26, 2021, 12 pages.
Decision of Technical Board of Appeal 3.3.01 of Dec. 18, 2018 for EP2324831, 29 pages.
Decision T 478/17 by EPO Board of Appeal 3.3.02 dated Sep. 8, 2020 to maintain EP2504332 in amended form, according to decision of the Opposition Division dated Dec. 12, 2016, 64 pages.
Food and Drug Administrations (Department of Health and Human Services) (Sep. 12, 2006). "Draft Guidance for Industry on Drug Interaction Studies—Study, Design, Data Analysis, and Implications for Dosing and Labeling Availability," Federal Register 71(126): 2 pages.
Fowler, S. (Jun. 2008, e-pub. Aug. 7, 2008). "In Vitro Evaluation Of Reversible And Irreversible Cytochrom P450 Inhibition: Current Status On Methodologies And Their Utility For Predicting Drug-Drug Interactions," The AAPS Journal 10(2):410-424.
Gekan, S.S. et al. (May 5, 2006). "The Practice of Medicinal Chemistry: Newest Soyakukagaku (2nd half)," Technomics, Inc., Revised 2nd Edition, written and edited by C. G. Wermuth, pp. 394-397. (English Machine Translation).
Jones, B.E. (2007). "Encyclopedia of Pharmaceutical Technology," Third Edition, vol. 1, Informa Healthcare, New York, pp. 406-418.
Letter from the Opponent, Sandoz AG, in response to the Provisional Opinion of the Board in Appeal T 478/17 for EP 2504332 dated Jul. 16, 2020, 10 pages.
Letter from the Opponent, Sandoz OG in Appeal T 478/17, for EP 2504332 dated Apr. 20, 2020, 55 pages.
Letter of the Patentee in Appeal T 478/18, for EP 2504332 dated Aug. 11, 2020, 16 pages.
Letter Regarding the Opposition Procedure and Auxiliary Request 4 as filed by Mathys & Squire with the EPO in EP3133070 on Nov. 16, 2021, 1 page.
Patentee's Observations, Main Request and Auxiliary Requests 1-3 as filed by Mathys & Squire with the EPO in EP3133070 on Jan. 8, 2021, 34 pages.
Provisional Opinion of the Board of Appeal in T 478/17, for EP2504332 dated May 11, 2020, 23 pages.

(56) References Cited

OTHER PUBLICATIONS

Zanger (2008). "Cytochromes P450: Role in the Metabolism and Toxicity of Drugs and other Xenobiotics" Chapter 8, RSC publishing, Ed. Costas Ioannides, pp. 250-251.
Zhang, L. et al. (Jun. 2009). "Predicting Drug-Drug Interactions: An FDA Perspective," The AAPS Journal 11 (2): 300-306.
Interlocutory Decision in Opposition Proceedings (Decision of the Opposition Division in EP3133070 dated Feb. 21, 2022), 83 pages.
Curriculum Vitae of Dr. John Warren, Director and Owner of Medicines Assessment Ltd., 19 pgs. (filed with Letter Accompanying Subsequently Filed Items filed by Brand Murray Fuller LLP in EP3133070 on Jul. 1, 2022).
Declaration of Dr. John Warren, Director of Medicines Assessment Limited, (filed with Letter Accompanying Subsequently Filed Items filed by Brand Murray Fuller LLP in EP3133070 on Jul. 1, 2022), 8 Pages.
EMEA (Dec. 17, 1997). "Note for Guidance on the Investigation of Drug Interactions," Committee for Propriety Medicinal Products (CPMP), pp. 1-14.
EMEA (Jul. 19, 2007). "Guideline on Strategies to Identify and Mitigate Risks for First-in-Human Clinical Trials with Investigational Medicinal Products," Committee for Propriety Medicinal Products (CPMP), pp. 1-12.
EMEA (May 25, 2007). "Reflection Paper on the Use of Pharmacogenetics in the Pharamacokinetic Evaluation of Medicinal Products," Committee for Propriety Medicinal Products (CPMP), pp. 1-6.
Genzyme (Aug. 2014). "Cerdelga 84mg Hard Capsules Summary of Product Characteristics (SmPC)," Genzyme, Reference ID: 3613065, 24 pages.
Hospira UK Ltd. (Apr. 19, 2022). "Irinotecan Hydrochloride 20 mg/ml Concentrate for Solution for Infusion," Medicines.Org, 18 pages, as retrieved on Jun. 27, 2022, from https://www.medicines.org.uk/emc/producU6506/smpc/print.
Hospira UK Ltd. (Apr. 27, 2021). "Iressa 250mg Film-Coated Tablets," Medicines.Org, 14 pages, as retrieved on Jun. 27, 2022, from https://www.medicines.org.uk/emc/producU6602/smpc/print.
Hospira UK Ltd. (Dec. 3, 2020). "Docetaxel Hospira 10 mg/ml Concentrate for Solution for Infusion," Medicines.Org, 37 pages, as retrieved on Jun. 27, 2022, from https://www.medicines.org.uk/emc/producU5762/smpc/print.
Hospira UK Ltd. (May 24, 2022). "Glivec 100 mg Film-Coated Tablets," Medicines.Org, 28 pages, as retrieved on Jun. 27, 2022, fromhttps://www.medicines.org.uk/emc/product/7779/smpc/print.
Letter Regarding Statement of Grounds of Appeal filed by Brand Murray Fuller LLP in EP3133070 on Jul. 1, 2022, 15 pages.
Notice of Grounds of Appeal, concerning EP3133070B, 31 pages, as filed with the EPO on Jun. 28, 2022.

* cited by examiner

Formula (I) Hemitartrate delays onset and progression of peripheral neuropathy in Fabry mice

Treatment of Fabry mice with Formula (I) Hemitartrate improves some markers of kidney function

12-month timepoint

ERT but not SRT reduces blood GL-3 levels in Fabry-Rag mice

Combination ERT/SRT is most effective at reducing GL-3 levels in Fabry-Rag mice liver & kidney SRT but not ERT delays onset of heat-insensitivity in Fabry-Rag mice (11 months)

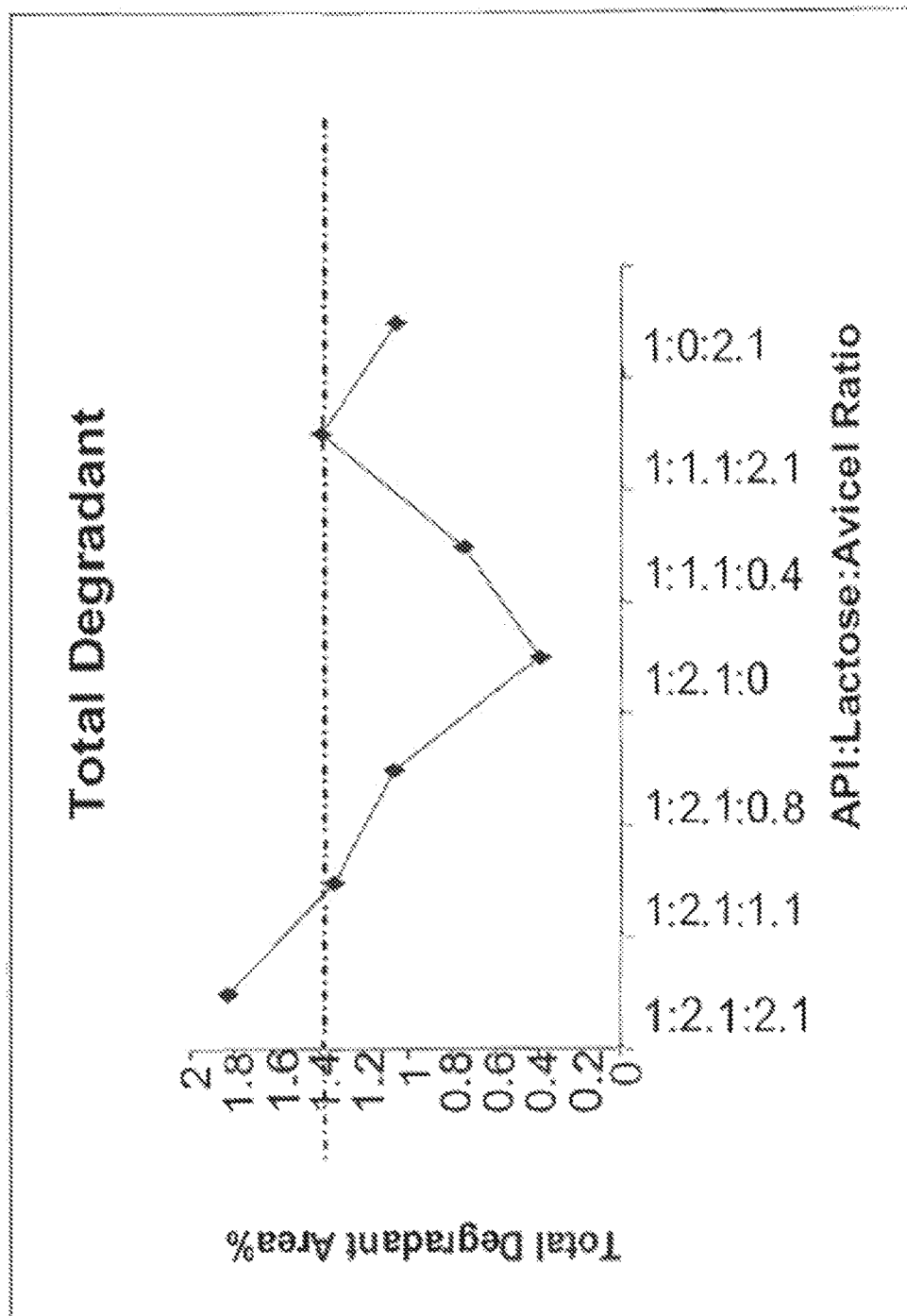

AMORPHOUS AND A CRYSTALLINE FORM OF GENZ 112638 HEMITARTRATE AS INHIBITOR OF GLUCOSYLCERAMIDE SYNTHASE

RELATED APPLICATIONS

This application is a 35 U.S.C. § 371 national stage filing of International Application No. PCT/US2010/057952, filed Nov. 24, 2010, which claims priority under 35 U.S.C. § 119 or 365 to U.S. Provisional Application No. 61/264,748, filed Nov. 27, 2009. The entire contents of each of the aforementioned applications are incorporated herein by reference in their entirety.

BACKGROUND

Glycosphingolipids (GSLs) are a class of naturally-occurring compounds which have a multitude of biological functions, including the ability to promote cell growth, cell differentiation, adhesion between cells or between cells and matrix proteins, binding of microorganisms and viruses to cells, and metastasis of tumor cells. GSLs are derived from glucosylceramide (GlcCer), which is produced from ceramide and UDP-glucose by the enzyme UDP-glucose: N-acylsphingosine glucosyltransferase (GlcCer synthase). The structure of ceramide is shown below:

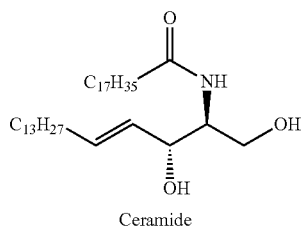

Ceramide

The accumulation of GSLs has been linked to a number of diseases, including Tay-Sachs, Gaucher, and Fabry diseases (see, for example, U.S. Pat. No. 6,051,598). GSLs have also been linked to certain cancers. For example, it has been found that certain GSLs occur only in tumors or at abnormally high concentrations in tumors; exert marked stimulatory or inhibitory actions on tumor growth when added to tumor cells in culture media; and inhibit the body's normal immunodefense system when shed by tumors into the surrounding extracellular fluid. The composition of a tumor's GSLs changes as the tumors become increasingly malignant and antibodies to certain GSLs inhibit the growth of tumors.

Compounds which inhibit GlcCer synthase can lower GSL concentrations and have been reported to be useful for treating a subject with one of the aforementioned diseases. A number of potent inhibitors of GlcCer, referred to herein as "amino ceramide-like compounds", are disclosed in U.S. Pat. Nos. 6,051,598, 5,952,370, 5,945,442, 5,916,911 and 6,030,995. The compound of Formula (I), shown below, is a GlcCer synthase inhibitor currently in clinical trials for the treatment of Gaucher disease:

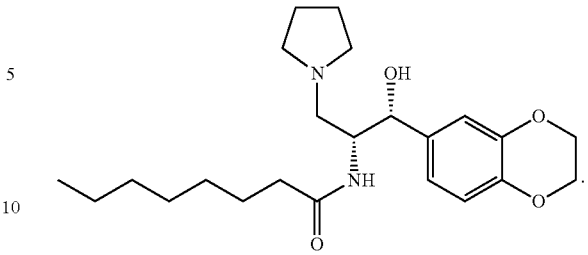

There is a need for salt forms of this drug candidate that are crystalline and otherwise have physical properties that are amenable to large scale manufacture. There is also a need for pharmaceutical formulations in which this drug candidate is stable and effectively delivered to the patient, as well as improved treatment methods utilizing this compound.

SUMMARY OF THE INVENTION

It has been found that the hemitartrate salt of the compound of Formula (I) (hereinafter "Formula (I) Hemitartrate") can be crystallized under well-defined conditions to provide certain non-hygroscopic crystalline forms. Formula (I) Hemitartrate has several advantageous properties when compared to other salts of Formula (I). As described further in Example 1, many Formula (I) salts, including citrate, malate, fumaric, methylsulfonic, and acetic, could not be obtained in solid form. Although the hydrochloric and 1:1 tartrate salt of Formula (I) were obtained in solid form, neither were crystalline and both were too hydroscopic for formulation. Formula (I) Hemitartrate is easier to formulate and synthesize than the free base and the other salts. Formula (I) Hemitartrate is also crystalline, non-hydroscopic, water-soluble and flows better than the corresponding free base (hereinafter "Formula (I) Free Base") and other salts. Thus, these favorable properties make Formula (I) Hemitartrate amenable to large scale manufacture as a drug candidate.

It has also been found that stable granules for capsule formulations of Formula (I) Hemitartrate can be prepared using defined ratios of a water insoluble filler, a water soluble filler and Formula (I) Hemitartrate. Based on this discovery, stable pharmaceutical formulations of Formula (I) Hemitartrate are disclosed.

It has also been found that the compound of Formula (I) or pharmaceutically acceptable salts thereof (including Formula (I) Hemitartrate) are metabolized by the liver, primarily by cytochrome P450 enzymes. Based on this discovery, methods of treatment with the compound of Formula (I) or pharmaceutically acceptable salts thereof (including Formula (I) Hemitartrate) that reduce the potential for drug/drug interactions are disclosed.

It has also been found that Gaucher mice administered recombinant glucocerebrosidase and then Formula (I) Hemitartrate showed lower levels of GL1 in visceral organs and a reduced number of Gaucher cells in the liver compared with treatment with glucocerebrosidase alone or Formula (I) Hemitartrate alone. Based on this discovery, combination therapies with the compound of Formula (I) or pharmaceutically acceptable salts thereof (including Formula (I) Hemitartrate) are also disclosed.

One embodiment of the present application is the hemitartrate salt of the compound represented by Formula (I). As noted above, the hemitartrate salt of the compound represented by Formula (I) is referred to herein as "Formula (I) Hemitartrate." The compound represented by Formula (I) is referred to herein as "Formula (I) Free Base."

Another embodiment of the present application provides a pharmaceutical composition comprising a pharmaceutically acceptable carrier or diluent and Formula (I) Hemitartrate.

Another embodiment provides a method of inhibiting glucosylceramide synthase or lowering glycosphingolipid concentrations in a subject in need thereof by administering to the subject an effective amount of Formula (I) Hemitartrate.

Another embodiment provides the use of Formula (I) Hemitartrate for the manufacture of a medicament for inhibiting glucosylceramide synthase or lowering glycosphingolipid concentrations in a subject in need thereof.

Another embodiment provides the use of Formula (I) Hemitartrate for inhibiting glucosylceramide synthase or lowering glycosphingolipid concentrations in a subject in need thereof.

Another embodiment is a method of treating a subject with Gaucher disease. The method comprises administering to the subject an effective amount of a first therapeutic agent in combination with an effective amount of a second therapeutic agent. The first therapeutic agent is represented by Formula (I) or a pharmaceutically acceptable salt thereof; and the second therapeutic agent is effective for the treatment of Gaucher disease.

Another embodiment is a method of treating a subject with Fabry disease. The method comprises administering to the subject an effective amount of a first therapeutic agent in combination with an effective amount of a second therapeutic agent. The first therapeutic agent is represented by Formula (I) or a pharmaceutically acceptable salt thereof; and the second therapeutic agent is effective for the treatment of Fabry disease.

Another embodiment provides pharmaceutical composition comprising: the hemitartrate salt of a compound represented by Formula (I); at least one water-soluble filler; at least one water-insoluble filler; at least one binder; and at least one lubricant.

Another embodiment of the invention is a method of treating a subject with Fabry disease. The method comprises the steps of:
  a) administering to the subject an effective amount of a compound of Formula (I), or a pharmaceutically acceptable salt thereof;
  b) testing the subject to determine whether the subject is a poor, intermediate or extensive/ultra rapid P450 metabolizer;
  c) if the subject is an intermediate or extensive/ultra rapid P450 metabolizer,
      determining an adjusted effective amount of the compound; and
  d) administering to the subject an adjusted effective amount of the compound of Formula (I) if the subject is an intermediate or extensive/ultra rapid P450 metabolizer and administering to the subject an effective amount of the compound of Formula (I) if the subject is a poor P450 metabolizer.

Another embodiment of the invention is a method of treating a subject with Gaucher disease. The method comprises the steps of:
  a) administering to the subject an effective amount of a compound of Formula (I), or a pharmaceutically acceptable salt thereof;
  b) testing the subject to determine whether the subject is a poor, intermediate or extensive/ultra rapid P450 metabolizer;
  c) if the subject is an intermediate or extensive/ultra rapid P450 metabolizer,
      determining an adjusted effective amount of the compound; and
  d) administering to the subject an adjusted effective amount of the compound of Formula (I) if the subject is an intermediate or extensive/ultra rapid P450 metabolizer and administering to the subject an effective amount of the compound of Formula (I) if the subject is a poor P450 metabolizer.

Another embodiment of the invention is a method of treating a subject with Fabry disease. The method comprises the steps of:
  a) administering to the subject an effective amount of a compound represented by the following structural formula:

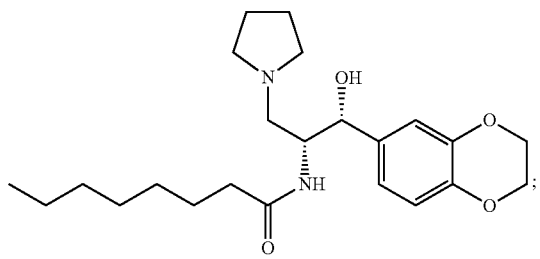 [SMILES: CCCCCCCC(=O)N[C@H](CN1CCCC1)[C@H](O)c1ccc2c(c1)OCCO2]

or a pharmaceutically acceptable salt thereof;
  b) assessing trough plasma levels of the compound in the subject; and
  c) adjusting the amount of compound administered to the subject so that the trough plasma levels of the compound are at least 5 ng/ml. Alternatively, the trough plasma levels and $C_{max}$ of the compound in the subject are assessed in step b) and in step c) the amount of compound administered to the subject is adjusted so that trough plasma levels of the compound in the subject are at least 5 ng/ml and the $C_{max}$ of the compound in the subject is below 100 ng/ml.

Another embodiment of the invention is a method of treating a subject with Gaucher disease. The method comprises the steps of:
  a) administering to the subject an effective amount of a compound represented by the following structural formula:

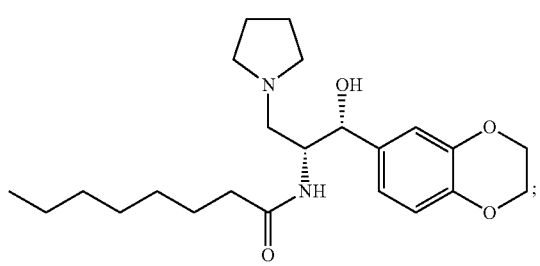 [SMILES: CCCCCCCC(=O)N[C@H](CN1CCCC1)[C@H](O)c1ccc2c(c1)OCCO2]

or a pharmaceutically acceptable salt thereof;
  b) assessing trough plasma levels of the compound in the subject; and c) adjusting the amount of compound administered to the subject so that the trough plasma levels of the compound in the subject are least 5 ng/ml. Alternatively, the trough plasma levels and $C_{max}$ of the compound in the subject are assessed in step b) and in step c) the amount of compound administered to the subject is adjusted so that trough plasma levels of the compound in the subject are at least 5 ng/ml and the $C_{max}$ of the compound in the subject is below 100 ng/ml

BRIEF DESCRIPTION OF THE DRAWINGS

FIG. 15 is a graph showing the total amount of degradation area of an HPLC trace of various blends comprising Formula (I) Hemitartrate, Lactose Monohydrate capsulating grade and Avicel PH 301 (Microcrystalline cellulose) after having been exposed to 85° C. for 3 days. The degradation area of the HPLC trace is ratio of the total area of peaks corresponding to degradation relative to the total area of peaks corresponding to Formula (I) Hemitartrate and degradation products.

DETAILED DESCRIPTION OF THE INVENTION

Figure 1:
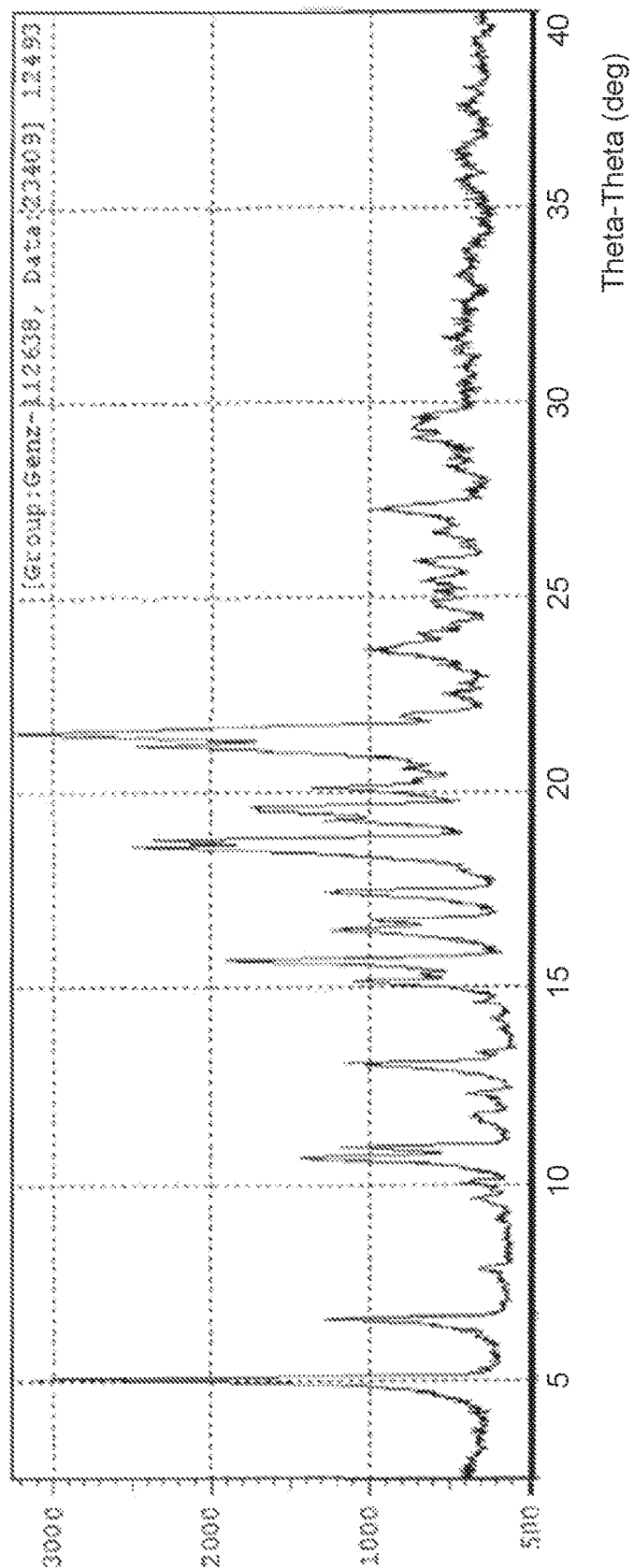
FIG. 1 shows the experimental XRPD pattern (room temperature) for Formula (I) Hemitartrate.

The present application provides unique crystalline forms of Formula (I) Hemitartrate and new pharmaceutical compositions of Formula (I) Hemitartrate comprising the crystalline forms of Formula (I) Hemitartrate described herein. The present application also provides methods of inhibiting glucosylceramide synthase or lowering glycosphingolipid concentrations in a subject in need thereof. Additionally, the present application provides methods for preparing specific crystalline forms of Formula (I) Hemitartrate. The present application also provides stable pharmaceutical formulations of Formula (I) Hemitartrate, combination therapies with the compound of Formula (I) or pharmaceutically acceptable salts thereof (including Formula (I) Hemitartrate) and methods of treatment with the compound of Formula (I) or pharmaceutically acceptable salts thereof (including Formula (I) Hemitartrate) that minimize the risk of drug/drug interactions.

Crystalline Forms of Formula (I) Hemitartrate

In a particular embodiment, at least a particular percentage by weight of Formula (I) Hemitartrate is crystalline. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%.

In another particular embodiment, at least a particular percentage by weight of Formula (I) Hemitartrate is a single crystalline form of Formula (I) Hemitartrate. Particular weight percentages include 70%, 72%, 75%, 77%, 80%, 82%, 85%, 86%, 87%, 88%, 89%, 90%, 91%, 92%, 93%, 94%, 95%, 96%, 97%, 98%, 99%, 99.5%, 99.9%, or a percentage between 70% and 100%.

As used herein, "crystalline" refers to a solid having a crystal structure wherein the individual molecules have a highly homogeneous regular locked-in chemical configuration. Crystalline Formula (I) Hemitartrate can be crystals of a single crystalline form of Formula (I) Hemitartrate, or a mixture of crystals of different single crystalline forms. A single crystalline form means Formula (I) Hemitartrate as a single crystal or a plurality of crystals in which each crystal has the same crystal form.

When a particular percentage by weight of Formula (I) Hemitartrate is a single crystalline form, the remainder of Formula (I) Hemitartrate is some combination of amorphous Formula (I) Hemitartrate, and/or one or more other crystalline forms of Formula (I) Hemitartrate excluding the single crystalline form. When the crystalline Formula (I) Hemitartrate is defined as a specified percentage of one particular crystalline form of Formula (I) Hemitartrate, the remainder is made up of amorphous form and/or crystalline forms other than the one or more particular forms that are specified. Examples of a single crystalline form include Form A of Formula (I) Hemitartrate characterized by one or more properties as discussed herein.

Because tartaric acid has two carboxylic acid groups, it can form salts with differing molar ratios of the compound represented by Formula (I) to tartrate (the conjugate base of tartaric acid). For example, the salt in which there is about a one to one molar ratio of tartrate to Formula (I) is Formula (I) Tartrate (1 tartrate:1 Formula (I)); and the salt in which there is about a one to two molar ratio of tartrate to Formula (I) is Formula (I) Hemitartrate (1 tartrate:2 Formula (I)).

The hemitartrate salt can exist in various stereoisomeric forms. Stereoisomers are compounds that differ only in their spatial arrangement. Enantiomers are pairs of stereoisomers whose mirror images are not superposable, most commonly because they contain an asymmetrically substituted carbon atom that acts as a chiral center. Diastereomers are stereoisomers that are not related as mirror images, most commonly because they contain two or more asymmetrically substituted carbon atoms.

When the stereochemistry is named (as in, for example, L-(+)-tartaric acid) or depicted by structure (as in, for example Formula (I)), the named or depicted stereoisomer is at least 60%, 70%, 80%, 90%, 99% or 99.9% by weight pure relative to the other stereoisomers. When a single enantiomer is named (as in, for example, L-(+)-tartaric acid) or depicted by structure (as in, for example Formula (I)), the depicted or named enantiomer is at least 80%, 90%, 99% or 99.9% by weight optically pure. Percent optical purity by weight is the ratio of the weight of the enantiomer over the weight of the enantiomer plus the weight of its optical isomer.

"Racemate" or "racemic mixture" means a compound of equimolar quantities of two enantiomers, wherein such mixtures exhibit no optical activity; i.e., they do not rotate the plane of polarized light.

Tartaric acid has three stereoisomers: L-(+)-tartaric acid or dextrotartaric acid and its enantiomer, levotartaric acid or D-(−)-tartaric acid, and the achiral form, mesotartaric acid. The L or D designation does not indicate the acid's ability to rotate the plane of polarized light.

Any of the stereoisomers of tartaric acid can be used to prepare Formula (I) Hemitartrate. For example, the hemitartrate can be formed from only one of its stereoisomers, or a combination of them thereof. The hemitartrate salt is selected from D-hemitartrate, L-hemitartrate, hemimesotartaric acid or racemic D,L-hemitartrate. In a specific embodiment, the hemitartrate salt is L-hemitartrate. "L-hemitartrate" means that the hemitartrate salt is formed from L-tartaric acid. Racemic D,L-hemitartrate means that both D-tartrate and L-tartrate were used in the preparation of Formula (I) Hemitartrate. The amount of D-tartrate in racemic D,L-hemitartrate may be greater than, equal to, or less than the amount of L-tartrate present.

"Levorotatory" signifies that polarized light is rotated to the left when passed through an asymmetric compound. The prefix to designate levorotary is "L".

"Dextrorotatory" signifies that polarized light is rotated to the right when passed through an asymmetric compound. The prefix to designate levorotary is "D".

Preparation of Formula (I) Hemitartrate

Formula (I) Hemitartrate can be prepared by mixing Formula (I) with L-tartaric acid in a suitable solvent. Precipitation of Formula (I) Hemitartrate can be assisted by the addition of a seed crystal. The solvents that may be used are methanol, water, ethanol, acetone, ethyl acetate, or combinations thereof.

The particular solid forms of Formula (I) Hemitartrate can be prepared, for example, by slow evaporation, slow cooling, and antisolvent precipitation. The solvents that may be used in these methods include water, heptane, hexane, toluene, dichloromethane, ethanol, isopropyl alcohol, acetonitrile, ethyl acetate, methanol, acetone, methyl tertiary-butyl ether (referred to as "TBME" herein), p-dioxane, and tetrahydrofuran (referred to as "THF" herein).

Formula (I) Hemitartrate solid forms can be prepared by solvent evaporation from a solution of Formula (I) Hemitartrate in a solvent or a solvent mixture. Suitable solvent mixtures include methanol, ethanol, acetone, water, ethyl acetate and dichloromethane. Preferred solvent mixtures include ethanol, methanol, water and acetone.

Formula (I) Hemitartrate solid forms can be prepared through slow cooling of a heated solution of Formula (I) Hemitartrate in a solvent. Suitable solvents include ethanol, methanol, water, acetone, and ethyl acetate.

Formula (I) Hemitartrate solid forms can be prepared through rapid cooling of a heated solution of Formula (I) Hemitartrate in a solvent, by placing the solution in an cooling bath. Suitable solvents include ethanol, methanol, acetone, water, ethyl acetate or mixtures of these solvents.

Formula (I) Hemitartrate solid forms can be prepared by adding a solution of Formula (I) Hemitartrate in a solvent as described above to an anti-solvent at a given temperature. More particularly, the anti-solvent is ethyl acetate, acetone, acetonitrile, toluene, THF, TBME, p-dioxane, isopropanol, or heptane. Particular solvent/antisolvent mixtures include methanol/ethyl acetate, methanol/acetone, methanol/hexane, methanol/heptane, methanol/acetonitrile, methanol/toluene, methanol/THF, methanol/TBME, methanol/p-dioxane, ethanol/ethyl acetate, ethanol/hexane, ethanol/heptane, ethanol, acetone, ethanol/acetonitrile, ethanol/toluene, ethanol/TBME, ethanol/THF, water/THF, water/isopropanol, water/acetonitrile, water/acetone, dichloromethane/heptane, dichloromethane/acetone, dichloromethane/ethyl acetate, dichloromethane/acetonitrile, dichloromethane/toluene, dichloromethane/THF, dichloromethane/TBME, dichloromethane/p-dioxane, and dichloromethane/isopropanol.

Preferred solvent/antisolvent mixtures include methanol/ethyl acetate, methanol/acetone, methanol/TBME, and water/acetone.

As used herein, "anti-solvent" refers to a solvent, in which Formula (I) Hemitartrate has low solubility and cause the Hemitartrate to precipitate out of solution in the form of fine powder or crystals.

Additional methods to generate the solid forms of Formula (I) Hemitartrate include precipitating the solid from ethyl acetate/acetone and optionally drying solid formed at room temperature. In another method, the solid can then be recrystallized from acetone with or without the addition of a seed crystal. Alternatively, Formula (I) Hemitartrate can be precipitated from ethyl acetate/acetone solvents and recrystallized from ethyl acetate. Alternatively, Formula (I) Hemitartrate can then be recrystallized from isopropanol. Alternatively Formula (I) Hemitartrate can be prepared using acetone only with no further recrystallization. Alternatively Formula (I) Hemitartrate can be precipitated from acetone following a brief reflux, without further recrystallization.

Alternatively, Formula (I) Hemitartrate can then be recrystallized from methanol/acetone with or without the addition of a seed crystal. Alternatively, Formula (I) Hemitartrate can then be recrystallized from water/acetone with or without the addition of a seed crystal.

Characterization of Crystalline Forms of Formula (I) Hemitartrate

In a particular embodiment, the crystalline form of Formula (I) Hemitartrate, crystal Form A, is characterized by one, two, three, four or five major XRPD peaks at 2θ angles of 5.1°, 6.6°, 10.7°, 11.0°, 15.9°, and 21.7°. In an even more particular embodiment, the crystalline form is characterized by XRPD peaks at 2θ angles of 5.1°, 6.6°, 10.7°, 11.0°, 13.3°, 15.1°, 15.9°, 16.5°, 17.6°, 18.6°, 18.7°, 19.0°, 20.2°, 21.7° and 23.5°. It is to be understood that a specified 2θ angle means the specified value±0.2°.

As used herein, "major XRPD peak" refers to an XRPD peak with a relative intensity greater than 25%. Relative intensity is calculated as a ratio of the peak intensity of the peak of interest versus the peak intensity of the largest peak.

Methods of Treatment Using Formula (I) Hemitartrate

As used herein, a subject is a mammal, preferably a human patient, but can also be an animal in need of veterinary treatment, such as a companion animal (e.g., dogs, cats, and the like), a farm animal (e.g., cows, sheep, pigs, horses, and the like) or a laboratory animal (e.g., rats, mice, guinea pigs, and the like). Subject and patient are used interchangeably.

One embodiment of the present application is a method of slowing, e.g., inhibiting or reducing the activity of glucosylceramide synthase or lowering glycosphingolipid concentrations in a subject in need thereof by administering to the subject an effective amount of Formula (I) Hemitartrate salt, including crystalline forms thereof, as described above.

A subject in need of treatment is a subject with a condition or disease that benefits from inhibiting glucosylceramide synthase or lowering glycosphingolipid concentrations in the cells, particularly the lysosome or the membrane of cells. Inhibitors of glucosylceramide synthase have been shown to be useful for treating lysosomal storage diseases such as Tay-Sachs, Gaucher or Fabry disease (see, for example, U.S. Pat. Nos. 6,569,889; 6,255,336; 5,916,911; 5,302,609; 6,660,749; 6,610,703; 5,472,969; 5,525,616, the entire teachings of which are incorporated herein by reference).

Examples of conditions or diseases include polycystic kidney disease and membranous glomerulopathy (see U.S. Provisional Patent Applications 61/130,401 and 61/102,541, the entire teachings of which are incorporated herein by reference), Glomerulonephritis and Glomerulosclerosis (See U.S. Provisional Patent Application 61/137,214) lupus (See PCT/US2009/001773, the entire teachings of which are incorporated herein by reference) diabetes, including type 2 diabetes (see WO 2006/053043, the entire teachings of which are incorporated herein by reference); treating disorders involving cell growth and division, including cancer, collagen vascular diseases, atherosclerosis, and the renal hypertrophy of diabetic patients (see U.S. Pat. Nos. 6,916, 802 and 5,849,326, the entire teachings of which are incorporated herein by reference); inhibiting the growth of arterial epithelial cells (see U.S. Pat. Nos. 6,916,802 and 5,849, 326); treating patients suffering from infections (see Svensson, M. et al., "Epithelial Glucosphingolipid Expression as a Determinant of Bacterial Adherence and Cytokine Production," *Infect. and Immun.*, 62:4404-4410 (1994), the entire teachings of which are incorporated herein by reference); preventing the host, i.e., patient, from generating antibodies against the tumor (see Inokuchi, J. et al., "Antitumor Activity in Mice of an Inhibitor of Glycosphingolipid Biosynthesis," *Cancer Lett.*, 38:23-30 (1987), the entire teachings of which are incorporated herein by reference); and treating tumors (see Hakomori, S. "New Directions in Cancer Therapy Based on Aberrant Expression of Glycosphingolipids: Anti-adhesion and Ortho-Signaling Therapy," *Cancer Cells* 3:461-470 (1991), Inokuchi, J. et al., "Inhibition of Experimental Metastasis of Murine Lewis Long Carcinoma by an Inhibitor of Glucosylceramide Synthase and its Possible Mechanism of Action," *Cancer Res.*, 50:6731-6737 (1990) and Ziche, M. et al., "Angiogenesis Can Be Stimulated or Repressed in In Vivo by a Change in GM3:GD3 Ganglioside Ratio," *Lab. Invest.*, 67:711-715 (1992), the entire teachings of which are incorporated herein by reference).

Formula (I) Hemitartrate can also be used for a cancer vaccine-like preparation (see, for example, U.S. Pat. Nos. 6,569,889; 6,255,336; 5,916,911; 5,302,609; 6,660,749; 6,610,703; 5,472,969; 5,525,616).

The compound of Formula (I) or a pharmaceutically acceptable salt thereof (including the hemitartrate salt thereof) can be used in the disclosed methods as a monotherapy, i.e., as the only pharmaceutically active ingredient being administered to treat the indication.

Alternatively, the compound of Formula (I) or a pharmaceutically acceptable salt thereof (including the hemitartrate salt thereof) can be used in the disclosed methods as a combination therapy with other therapeutically active drugs known in the art for treating the desired diseases or indications. "Co-therapy" or "combination" or "combination therapy" or "co-administered" are used interchangeably herein and mean that the compound of Formula (I) or pharmaceutically acceptable salt thereof (including the hemitartrate salt) is administered before, after, or concurrently with one or more other therapeutic agents. In one embodiment, a combination therapy is used to treat a lysosomal disease such as Gaucher disease or Fabry disease. Alternatively, the compound of Formula (I) or pharmaceutically acceptable salt thereof (including the hemitartrate salt) is co-administered simultaneously (e.g., concurrently) as either separate formulations or as a joint formulation. Alternatively, the agents can be administered sequentially, as separate compositions, within an appropriate time frame, as determined by the skilled clinician (e.g., a time sufficient to allow an overlap of the pharmaceutical effects of the therapies). The compound of Formula (I) or pharmaceutically acceptable salt thereof (including the hemitartrate salt) and one or more other therapeutic agents can be administered in a single dose or in multiple doses, in an order and on a schedule suitable to achieve a desired therapeutic effect.

Therapeutic agents effective for the treatment of Gaucher disease include glucocerebrosidase, analogues of glucocerebrosidase, inhibitors of glucosylceramide synthase and molecular chaperones which bind to glucocerebrosidase and restore its correct conformation. Glucocerebrosidase or analogues thereof can be human or mammal derived. Alternatively, glucocerebrosidase and analogues thereof can be obtained recombinately. Analogues of glucocerebrosidase include truncated forms of the enzyme and/or enzymes with amino acid substitutions relative to the native amino sequence of the native enzyme, provided that the biological activity is retained. Examples of analogues of glucocerebrosidase include Imiglucerase (sold under the tradename Cerezyme®) by Genzyme Corporation), Taliglucerase Alfa (to be marketed under the tradename Uplyso® and developed by Protalix Biotherapeutics, Inc.) and Velaglucerase Alfa (developed by Shire PLC), which are recombinant DNA-produced analogue of human β-glucocerebrosidase. Examples of molecular chaperones include isofagomine (in development under the tradename Plicera™ by Amicus Therapeutics, Cranbury, N.J.). Isofagomine is also known as afegostat tartrate and contains the tartrate salt form of isofagomine as its active ingredient. Examples of glucocerebrosidase inhibitors include miglustat (developed under the tradename of Zavesca™ by Actelion Pharmaceuticals Ltd. Allschwil, Switzerland).

Therapeutic agents effective for the treatment of Fabry disease include α galactosidase A, analogues of α galactosidase A and molecular chaperones which bind to α galactosidase A and restore its correct conformation. α Galactosidase A or analogues thereof can be human or mammal derived. Alternatively, α galactosidase A and analogues thereof can be obtained recombinantely. Analogues of α galactosidase A include truncated forms of the enzyme and/or enzymes with amino acid substitutions relative to the native amino sequence of the native enzyme, provided that the biological activity is retained. Examples of analogues of α galactosidase A include Agalsidase beta (a recombinant human α-galactosidase sold under the tradename Fabrazyme® as a freeze-dried medicine by Genzyme Corporation) and Agalsidase alfa (a recombinant protein sold under the tradename Replagal® by Shire PLC). Examples of molecular chaperones include migalastat (developed under the tradename Amigal™ by Amicus Therapeutics, Cranbury, N.J. as a drug containing migalastat hydrochloride as its active ingredient).

In one embodiment, the combination therapy for the treatment of Gaucher or Fabry disease is carried out in two stages. In a first stage, a drug effective for the treatment of Gaucher disease or Fabry disease (typically, glucocerebrosidase of an analogue thereof for Gaucher disease and galactosidase A or an analogue thereof for Fabry disease) is used to stabilize the subject. For example, in Gaucher disease (or Fabry disease), one of these drugs is used to reduce the burden of GL-1 storage in the visceral organs such as in the liver, spleen, lung and/or kidney. Once this has been accomplished, the compound of Formula (I) or a pharmaceutically acceptable salt thereof (including the hemitartrate salt) is used in the second stage as a convenient maintenance therapy. The first stage typically lasts up to one, two, three or four weeks or up to one, two, three, four, six, nine or twelve months, or until the subject's platelet count is equal to or greater than 100,000 mm$^3$; hemoglobin concentration is equal to or greater than 11 g/dl (female) or 12 g/dl (male); and/or the subject's spleen volume is less than or equal to 10 multiples of normal and liver volumes are less than or equal to 1.5 multiples of normal. Administration of the first stage is typically ended once therapy with the compound of Formula (I) is initiated.

As used herein, an "effective amount" refers to an amount effective to alleviate the existing symptoms of the subject being treated with minimal unacceptable side effects in the subject. The exact formulation, route of administration, and dosage is chosen by the individual physician in view of the patient's condition. Dosage amount and interval can be adjusted individually to provide plasma levels of the active compound that are sufficient to maintain desired therapeutic effects. In addition to the patient's condition and the mode of administration, the dose administered would depend on the severity of the patient's symptoms and the patient's age and weight. An effective amount will typically result in plasma trough levels of the compound above at least 5 ng/ml. If plasma trough levels are below 5 ng/ml following administration of an effective amount of the compound, the dose being administered to that subject is changed to an "adjusted effective amount" such that the trough levels of the compound are at least 5 ng/ml. Alternatively, if trough plasma levels of the compound are below 5 ng/ml and/or the $C_{max}$ is above 100 ng/ml following administration of an effective amount of the compound, the dose being administered to the subject is changed to an "adjusted effective amount" such that the trough plasma levels of the compound are at least 5 ng/ml and the $C_{max}$ is below 100 ng/ml. Effective amounts can range from 0.1 to 500 mg/per day. Alternatively, the effective amount ranges from 50-300 mg/day. In another alternative, the effective amount ranges from 100-300 mg/day. The compound of the present application may be administered continuously or at specific timed intervals. For example, the compound of the present application may be administered 1, 2, 3, or 4 times per day, such as, e.g., a daily or twice-daily formulation. Commercially available assays may be employed to determine optimal dose ranges and/or schedules for administration.

In one embodiment, an effective amount for the compound of Formula (I) or a pharmaceutically acceptable salt thereof (including the hemitartrate salt described above) is (whether as a monotherapy or as a co-therapy) a daily dose of from 25 milligrams to 300 milligrams (alternatively 25 milligrams to 150 milligrams; in another alternative from 50 milligrams to 300 milligrams; and in another alternative from 100 milligrams to 300 milligrams), such as 25, 50, 100, 200 or 300 milligrams per day. In a specific embodiment, an effective amount of the compound of Formula (I) or a pharmaceutically acceptable salt thereof (including Formula (I) Hemitartrate) is (whether as a monotherapy or as a co-therapy) a twice daily dose of 50 milligrams (for a total of 100 milligrams per day), 100 milligrams (for a total of 200 milligrams per day) or 150 milligrams (for a total of 300 milligrams per day). In an alternative embodiment, an effective amount for the compound of Formula (I) or a pharmaceutically acceptable salt thereof (including Formula (I) Hemitartrate) is (whether as a monotherapy or as a co-therapy) administered as a once daily dose of 100 milligrams/day, 200 milligrams/day or 300 milligrams/day.

In another embodiment, an effective amount is determined is by assuming that the subject is a "poor P450 metabolizer" and then assessing trough plasma levels and/or $C_{max}$. The amount administered to the subject is then changed to an adjusted effective amount, as described below, if the trough plasma levels are below 5 ng/ml; or the trough levels of the compound are below 5 ng/ml and/or the $C_{max}$ is above 100 ng/ml; or if the subject is determined to be an intermediate or extensive/ultrarapid P450 metabolizer. An effective amount for poor P450 metabolizers is (whether as a monotherapy or as a co-therapy) commonly between 100-200 milligrams per day, for example 100 or 200 milligrams, as a once daily dose or twice daily dose.

Typically, the pharmaceutical compositions of the present application can be administered before or after a meal, or with a meal. As used herein, "before" or "after" a meal is typically within two hours, preferably within one hour, more preferably within thirty minutes, most preferably within ten minutes of commencing or finishing a meal, respectively.

It has now been found that the compound of Formula (I) and pharmaceutically acceptable salts thereof (including Formula (I) Hemitartrate) is metabolized by the liver, primarily by cytochrome P450 enzymes. Cytochrome P450s ("CYPs") are the principal hepatic xenobiotic metabolizing enzymes. There are eleven xenobiotic-metabolizing cytochrome P450s expressed in a typical human liver (i.e., CYP1A2, CYP2A6, CYP2B6, CYP2C8/9/18/19, CYP2D6, CYP2E1 and CYP3A4/5). It has now also been found that CYP2D6 and CYP3A4 are the primary cytochrome P450 isoforms that are responsible for de-toxifying the compound of Formula (I) and its pharmaceutically active salts, such as Formula (I) Hemitartrate. The level of activity of P450 enzymes differs according to the individual. For example, individuals can be classified as poor, intermediate and extensive/ultra rapid P450 metabolizers. Because lower levels of P450 activity in an individual can give rise to drug/drug interactions ("DDI"), another embodiment of the invention is to determine whether the subject is a poor, intermediate and extensive/ultra rapid P450 metabolizer. If the subject is an intermediate or extensive/ultra rapid metabolizer, then the dose administered to that subject should be raised to an "adjusted effective dose", i.e., the amount which results in trough plasma levels of the compound of at least 5 ng/ml; or the amount which results in trough levels of the compound or at least 5 ng/ml and a $C_{max}$ of the compound below 100 ng/ml. The dose can raised incrementally and the subject retested once, twice, three, four or as many times as necessary to achieve an adjusted effective dose.

For the CYP 2D6 gene there are four predicted phenotypes:

A "poor P450 metabolizer" carries two mutant alleles, which result in complete loss of enzyme activity.

A, "intermediate P450 metabolizer" possess one reduced activity allele and one null allele.

A "extensive P450 metabolizer" possess at least one and no more than two normal functional alleles.

A "ultra rapid P450 metabolizer" carries multiple copies (3-13) of functional alleles and produce excess enzymatic activity.

A subject is typically assessed as being a poor, intermediate or extensive/ultra rapid P450 metabolizer either through genotyping or through the monitoring of the trough plasma levels of a drug that is metabolized by a P450 enzyme such as CYP2D6 or CYP3A4. Commonly, the trough plasma levels and/or $C_{max}$ of the compound of Formula (I) or a pharmaceutically acceptable salt thereof, including Formula (I) hemitartrate are monitored in the subject for up to one, two, three or four weeks, or up to one, two, three, six, nine or twelve months or more following initiation of treatment with the compound. Adjustments to the dose are made, as necessary, to maintain the levels within the described limits, i.e., a trough plasma level at or above 5 ng/ml.

Subjects can become poor P450 metabolizers as a result of being treated with certain drugs that are P450 enzyme inhibitors. Examples of such drugs include paroxetine, fluoxetine, quinidine, or ketoconazole. Alternatively, a subject is a poor P450 metabolizer as a result of low expression of a P450 enzyme. In such instances, the low expression can be assessed by determining P450 enzyme expression in the subject, i.e., genotyping the subject for the P450 enzyme. For example, expression of CYP2D6 is commonly assessed by PCR (McElroy et. al. "CYP2D6 Genotyping as an Alternative to Phenotyping for Determination of Metabolic Status in a Clinical Trial Setting", AAPS Pharmsi (2000) 2(4):article 33 (http://www.pharmsci.org/)) or by microarray based pharmacogenomic testing (Background Information, Roche Diagnostics "The CYP450 Gene Family and Drug Metabolism", Hoffmann La Roche Ltd.), the entire teachings of which are incorporated herein by reference. As such, the subject can be conveniently genotyped for P450 expression (e.g., CYP2D6) prior to the initiation of treatment and administered an adjusted effective amount, if necessary. In the event of genotyping prior to the initiation of treatment, it is still advisable to monitor trough plasma levels and $C_{max}$ of the compound and adjust the dose, as necessary.

Effective amounts for migalastat, agalsidase β, imiglucerase, isofagomine and miglustat are as described on the drug label or as carried out in the clinical trials of each drug.

The compound of Formula (I) can react with pharmaceutically acceptable acids to form a pharmaceutically acceptable salt. Examples of pharmaceutically acceptable acids included inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Pharmaceutical Compositions Including Formula (I) Hemitartrate

Suitable formulations and modes of administration for the compound of Formula (I) or a pharmaceutically acceptable salt thereof (including the hemitartrate salt thereof) include those described in U.S. Pat. No. 7,253,185, the entire teachings of which are incorporated herein by reference. A preferred formulation for Formula (I) Hemitartrate is described in the following paragraphs.

One embodiment of the invention is a pharmaceutical composition comprising Formula (I) Hemitartrate, at least one water-soluble filler, at least one water-insoluble filler, at least one binder, and at least one lubricant. Suitable water-soluble fillers can include, for example, anhydrous lactose, lactose monohydrate, mannitol, sodium chloride, powdered sugar, sorbitol, sucrose, inositol and pregelatinized starch. Suitable water-insoluble fillers can include, for example, microcrystalline cellulose, calcium phosphate and starch. Suitable binders can include, for example, pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate. Suitable lubricants can include, for example, hydrogenated vegetable oil, calcium stearate, and glyceryl behenate. In one embodiment of the pharmaceutical composition, the water-soluble filler is selected from the group consisting of anhydrous lactose, lactose monohydrate, mannitol, sodium chloride, powdered sugar, sorbitol, sucrose, inositol and pregelatinized starch; the water-insoluble filler is selected from the group consisting of microcrystalline cellulose, calcium phosphate and starch the binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the lubricant is selected from the group consisting of hydrogenated vegetable oil, calcium stearate, and glyceryl behenate.

The pharmaceutical formula comprises between 8 wt % to 32 wt %, between 8 wt % to 24 wt %, between 12 wt % to 20 wt % or between 14 wt % to 18 wt % of the water insoluble filler on a dry solids basis.

The pharmaceutical formula comprises between 26 wt % to 50 wt %, between 30 wt % to 46 wt %, between 34 wt % to 46 wt % or between 38 wt % to 44 wt % of the water soluble filler on a dry solids basis.

The pharmaceutical composition comprises between 30 wt % and 45 wt %, between 35 wt % and 40 wt % and 36 wt % to 39 wt % Formula (I) Hemitartrate on a dry solids basis.

The pharmaceutical formulation typically comprises between 2 wt % and 6 wt % binder on a dry solids basis.

The pharmaceutical formulation typically comprises between 0.1 wt % and 2 wt % binder on a dry solids basis.

In a specific embodiment, the pharmaceutical formula comprises between 8 wt % to 32 wt % water insoluble filler, between 26 wt % to 50 wt %, water soluble filler, between 30 wt % and 45 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

In a specific embodiment, the pharmaceutical formula comprises between 8 wt % to 32 wt % water insoluble filler, between 26 wt % to 50 wt %, water soluble filler, between 35 wt % and 40 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

In another specific embodiment, the pharmaceutical formula comprises between 8 wt % to 24 wt % water insoluble filler, between 30 wt % to 46 wt %, water soluble filler, between 35 wt % and 40 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

In another specific embodiment, the pharmaceutical formula comprises between 12 wt % to 20 wt % water insoluble filler, between 34 wt % to 46 wt %, water soluble filler, between 35 wt % and 40 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

In another specific embodiment, the pharmaceutical formula comprises between 14 wt % to 18 wt % water insoluble filler, between 38 wt % to 44 wt %, water soluble filler, between 35 wt % and 40 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

In another specific embodiment, the pharmaceutical formula comprises between 14 wt % to 18 wt % water insoluble filler, between 38 wt % to 44 wt %, water soluble filler, between 36 wt % and 39 wt % Formula (I) Hemitartrate, between 2 wt % and 6 wt % binder and between 0.1 wt % and 2 wt % binder, all on a dry solids basis. More specifically, the water-soluble filler is lactose monohydrate; and the water-insoluble filler is microcrystalline cellulose. Even more specifically the water-soluble filler is lactose monohydrate; the water-insoluble filler is microcrystalline cellulose; the binder is hydroxypropyl methylcellulose; and the lubricant is glyceryl behenate.

The invention is illustrated by the following examples, which are not intended to be limiting in any way.

EXPERIMENTAL

Example 1

Preparation of Salts of Formula (I)

The hemitartrate salt of Formula I is readily crystallized and exhibits many beneficial properties as compared to other salts. For example, the following acids were used in the preparation of salts of the compound represented by Formula (I): citric acid (generating salts in 1:1, 1:2, and 1:3 (salt:Formula I) ratios); L-malic (1:1 and 1:2); methane sulfonic acid (1:1); fumaric acid (1:1 and 1:2); hydrochloric acid (1:1); acetic acid (1:1) and tartaric acid (1:1 and 1:2). Only salts generated by hydrochloric acid (1:1); tartaric acid (1:1) and tartaric acid (1:2) were of solid form. Of these three salts hydrochloric acid (1:1) and tartaric acid (1:1) were found to be hygroscopic and non-crystalline and therefore unacceptable for use in a pharmaceutical product. The hemitartrate (1 salt:2 Formula I) of the compound represented by Formula I was found to be crystalline and non-hygroscopic.

Acetone Preparation of Formula (I) Hemitartrate

L-tartaric acid (6.02 g, 40.11 mmol, 0.497 equivalents) was dissolved in acetone (175 mL) by refluxing the solution and then cooling to room temperature. Formula (I) Free Base (32.67 g, 80.76 mmol) was dissolved in acetone (300 mL) at room temperature. The L-tartaric acid solution was added to the Formula (I) Free Base solution at room temperature over 15 min. A white precipitate formed half way through the addition. The mixture was stirred at room temperature for 0.5 h hours and then briefly refluxed and cooled to room temperature. After stirring a room temperature for 0.5 h, the white precipitate was filtered. The white solid was washed twice with acetone (2×130 mL). The solid was air dried and then vacuum dried at 55-60° C. The yield was 36.66 g (95%).

5% Methanol in Acetone Preparation of Formula (I) Hemitartrate.

Formula (I) Free Base, 10 g/24.7 mmol, was dissolved in 5% Methanol/Acetone 120 mL or 240 mL. L-tartaric acid, 1.85 g/12.3 mmol, was dissolved in 5% Methanol/Acetone 60 mL or 120 mL (N or 2N) by warming to 40-45° C., and this solution was added to the first solution. After 1 hour without precipitation, 1 mg of Formula (I) Hemitartrate was added as a seed crystal. Precipitation occurred after 5 minutes, and the reaction continued to stir for 30 minutes more. The reaction was then heated at reflux for 5 minutes (the precipitate was completely soluble) and then cooled to room temperature in a water bath 20-22° C. Precipitate formed and the reaction continued to stir for 3 hours. The final product was collected by filtration and was washed with acetone, 2×40 mL, and then dried in the vacuum oven at 55-60° C. for 16 hours. Product weight was 8.72 g/74% yield.

1% Water in Acetone Preparation of Formula (I) Hemitartrate.

Formula (I) Free Base (10 g/24.7 mmol) was dissolved in 1% Water/Acetone 120 mL or 240 mL at room temperature. L-tartaric acid, 1.85 g/12.3 mmol, was dissolved in 1% Water/Acetone 60 mL or 120 mL (N or 2N) by warming to 40-45° C., and this solution was added to the first solution. After 1 hour without precipitation, 1 mg of Formula (I) hemitartrate was added as a seed crystal. Precipitation occurred after 5 minutes, and the reaction continued to stir for 30 minutes. The reaction was then heated at reflux for 5 minutes (the precipitate was not completely soluble) and then cooled to room temperature in a water bath 20-22° C. Precipitate formed and the reaction continued to stir for 3 hours. The final product was collected by filtration and was washed with acetone, 2×40 mL, and then dried in the vacuum oven at 55-60° C. for 16 hours. Product weight was 8.62 g 73% yield.

5% Methanol in Acetone Recrystallization of Formula (I) Hemitartrate.

Formula (I) Hemitartrate (3.06 g) was dissolved in 116 mL of 5% methanol in acetone at reflux. The solution was cooled to room temperature and stirred at room temperature for 2 h. The white precipitate was filtered and washed with 10 mL of 5% methanol in acetone and then acetone (15 mL). After vacuum drying for 18 h at 55-60° C., received 2.38 g of Formula (I) Hemitartrate (78% recovery).

1% $H_2O$ in Acetone Recrystallization of Formula (I) Hemitartrate.

Formula (I) Hemitartrate (3.05 g) was dissolved in 125 mL of 1% $H_2O$ in acetone at reflux. The solution was cooled to room temperature and stirred at room temperature for 2 h. The white precipitate was filtered and washed with 10 mL of 1% $H_2O$ in acetone and then acetone (15 mL). After vacuum drying overnight at 55-60° C., 2.35 g of Formula (I) Hemitartrate (77% recovery) was obtained.

Example 2

Preparation Crystalline Formula (I) Hemitartrate

Formula (I) Hemitartrate was crystallized by several methods. Batch 1 was prepared using ethyl acetate/acetone solvents and dried at room temperature. Batch 3 was prepared using ethyl acetate/acetone solvents and recrystallized from ethyl acetate. Batch 4 was recrystallized from acetone using Batch 1 material. Batch 5 was recrystallized from isopropanol. Batch 7 was prepared using ethyl acetate/ acetone solvent similar to Batch 1 but in a large scale, Batch 8 was prepared using acetone only with no further recrystallization. Batch 9 was prepared using acetone only with brief reflux, again no further recrystallization.

TABLE 1

Summary of polymorphism screening of Batches 1-9 of Formula (I) Hemitartrate

| Batch No. | Processing Method | DSC Melting Point (° C.) | Enthalpy (J/g) | Microscope | TGA |
|---|---|---|---|---|---|
| 1 | Acetone/ethyl acetate precipitation* | 162 | −81.4 | Crystal | 99.91% at 100° C. 98.73% at 175° C. |
| 2 | Acetone/ethyl acetate precipitation- dried at room temperature* | 164 | −95.6 | Crystal | N/A |
| 3 | Acetone/ethyl acetate precipitation- dried at 55-60° C. | 166 | −97.8 | Crystal | 100.0% at 100° C. 99.98% at 153° C. |
| 4 | Recrystallization from acetone | 166 | −107.2 | Crystal | 100.2% at 100° C. 100.2% at 153° C. |
| 5 | Recrystallization from isopropanol | 166 | −102.6 | Crystal | 100.0% at 100° C. 100.0% at 153° C. |
| 7 | Acetone/ethyl acetate precipitation | 166 | −99.4 | Crystal** | 100.1% at 100° C. 99.91% at 153° C. |
| 8 | Acetone precipitation | 165 | −100.7 | Crystal** | 100.0% at 100° C. 100.0% at 153° C. |
| 9 | Acetone precipitation with brief reflux | 165 | −100.2 | Crystal** | |

*containing some free base in the DSC thermogram.
**containing habits changed in these batches from rod, plate-shaped to needle, rod, and irregular shapes.

Crystal forms of Formula (I) Hemitartrate were also prepared using slow evaporation, slow cooling, fast cooling and anti-solvent precipitation with a variety of solvents.

Slow Evaporation Method. A weighed sample (usually 20 mg) was treated with aliquots of the test solvent. Aliquots were typically 100-200 μL. Between solvent additions, the mixture was shaken or sonicated. When the solids dissolved, as judged by visual inspection, the solution was allowed to evaporate under ambient conditions in an open vial covered with aluminum foil perforated with pinholes. Solubilities were estimated from these experiments based on the total solvent added to obtain a clear solution.

TABLE 2

Approximate solubility of Formula (I) Hemitartrate at room temperature (20-25° C.).

| Organic Solvent | Approximate Solubility (mg/mL) |
|---|---|
| Heptane | Not Available |
| Hexane | Not Available |
| Toluene | <5 |
| Dichloromethane | 100 |
| Ethanol | 29 |
| Isopropyl alcohol | <5 |
| Acetonitrile | <5 |
| Ethyl Acetate | <5 |
| Methanol | >200 |
| Acetone | <5 |

TABLE 2-continued

Approximate solubility of Formula (I) Hemitartrate at room temperature (20-25° C.).

| Organic Solvent | Approximate Solubility (mg/mL) |
|---|---|
| Methyl t-butyl ether (TBME) | <5 |
| p-Dioxane | <5 |
| Tetrahydrofuran (THF) | <5 |

TABLE 3

Summary of polymorphism using slow evaporation approach.

| Organic Solvent | Solid form generated from Slow Evaporation | DSC Melting Point (° C.) | Enthalpy (J/g) | Microscope | TGA |
|---|---|---|---|---|---|
| Methanol | No | N/A | N/A | N/A | N/A |
| Ethanol | Yes | 165 | −95.0 | Crystal** | 100.0% at 100° C. 100.0% at 150° C. |

**particles were plate and rod-shaped

Slow/Fast Cooling Method. Formula (I) Hemitartrate was dissolved in a test solvent at 50-60° C. The resulting solution was then allowed to cool to ambient temperature (slow cool). If no solids formed after a day, the vials were placed in a refrigerator. For fast cool experiments, the resulting solution was then allowed to cool in a refrigerator. The solids were collected by filtration an air-dried.

TABLE 4

Summary of polymorphism using slow cooling approach.

| Organic Solvent | Solid form generated from Slow Cooling | DSC Melting Point (° C.) | Enthalpy (J/g) | Microscope | TGA |
|---|---|---|---|---|---|
| Ethanol | Yes | 167 | −106.2 | Crystal** | 100.1% at 100° C. 100.1% at 150° C. |

**particles were plate and rod-shaped

TABLE 5

Summary of polymorphism using fast cooling approach.

| Organic Solvent | Solid form generated from Fast Cooling | DSC Melting Point (° C.) | Enthalpy (J/g) | Microscope | TGA |
|---|---|---|---|---|---|
| Ethanol | Yes | 167 | −106.2 | Crystal** | 100.0% at 100° C. 100.0% at 150° C. |

**particles were plate and rod-shaped

Anti-Solvent Method. Formula (I) Hemitartrate was dissolved in a solvent. An anti-solvent was added to the solution. The solids that formed were collected by filtration an air-dried.

TABLE 6

Summary of polymorphism screening using anti-solvent approach

| Organic Solvent | Solid form generated from Anti-solvent Approach | DSC Melting Pont (° C.) | Enthalpy (J/g) | Microscope | TGA |
|---|---|---|---|---|---|
| Methanol/ ethyl acetate | Yes | 167 | −99.5 | Crystal* | 100.1% at 100° C. 100.1% at 150° C. |
| Methanol/ acetone | Yes | 167 | −106.2 | Crystal* | 100.3% at 100° C. 100.2% at 150° C. |
| Methanol/ acetonitrile | No | N/A | N/A | N/A | N/A |
| Methanol/ toluene | No | N/A | N/A | N/A | N/A |
| Methanol/ THF | No | N/A | N/A | N/A | N/A |
| Methanol/ TBME | Yes | 167 | −102.0 | Crystal* | 100.2% at 100° C. 100.1% at 150° C. |
| Methanol/ p-dioxane | No | N/A | N/A | N/A | N/A |
| Water/THF | No | N/A | N/A | N/A | N/A |
| Water/ TMBE | No | N/A | N/A | N/A | N/A |
| Water/ isopropanol | No | N/A | N/A | N/A | N/A |
| Water/ acetonitrile | No | N/A | N/A | N/A | N/A |
| Water/ acetone | No | N/A | N/A | N/A | N/A |
| Dicholoro-methane/ heptane | Yes | 165 | −89.2 | Crystal** | 100.0% at 100° C. 99.99% at 150° C. |
| Dicholoro-methane/ ethyl acetate | Yes | 167 | −97.8 | Crystal* | 100.2% at 100° C. 100.1% at 150° C. |
| Dicholoro-methane/ toluene | Yes | 164 | −89.8 | Crystal* | 99.95% at 100° C. 99.86% at 150° C. |
| Dicholoro-methane/ TBME | Yes | 167 | −98.6 | Crystal** | 100.0% at 100° C. 99.91% at 150° C. |
| Dicholoro-methane/p-dioxane | Yes (little) | N/A | N/A | N/A | N/A |
| Dicholoro-methane/ isopropanol | No | N/A | N/A | N/A | N/A |

: The particles were plate and rod-shaped.
**Individual particles had more than one bifrigence color.
*** The particles were needle and rod-shaped.

Example 3

Physical Properties of Formula (I) Hemitartrate

Differential scanning calorimetry (DSC). DSC data was collected on a TA Q100 instrument utilizing nitrogen as the purge gas. Approximately 2-5 mg of sample was weighed accurately into an aluminum DSC pan. The pan was covered with a lid and perforated with a forceps. The sample cell was equilibrated at 30° C. and heated at a rate of 10° C. per minute to a final temperature of 220° C.

Hot stage microscopy. Hot stage microscopy was performed using a Linkam hot stage (model FTIR 600) mounted on a Leica DM LP microscope equipped with a Sony DXC-970MD 3CCD camera for image collection. A 40× objective was used with polarized light to view samples. Each samples was placed between two cover slips. Each sample was visually observed as the stage was heated. Images were captured using Links version 2.27 (Linkam). The hot stage was calibrated using USP melting point standards.

The endothermic transition observed in the DSC profile was confirmed to be a melting transition at a temperature between 160-163° C. by hot stage microscopy.

Example 4

X-ray Powder Diffraction of Formula (I) Hemitartrate

All the X-ray Powder Diffraction (XRPD) analyses were done at SSCI, Inc. (West Lafayette, Ind. 47906). XPRD analyses were performed using a Shimadzu XRD-6000 X-ray powder diffractometer using Cu K α radiation. The instrument is equipped with a fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. The theta-two theta continuous scan at 3°/min (0.4 sec/0.02° step) from 2.5 to 40° 2θ was used. A silicon standard was analyzed to check the instrument alignment. Data were collected and analyzed using XRD-6000 v 4.1.

Example 5

Comparison of Formula (I) Hemitartrate to Formula (I) Free Base

The solid characterization of the free base and the hemitartrate salt are summarized in Table 7. Formula I Hemitartrate has superior properties as compared to Formula I free base. For example, Formula I Hemitartrate has a higher melting point (>150° C.), higher packing energy (greater endothermic enthalpy), lower variance in particle size, higher aqueous solubility (over 300 mg/mL in water), suitable crystal shape, and higher bulk density as compared to Formula I Free Base.

TABLE 7

Summary of solid state and physical and chemical properties of Formula (I) Free Base and Formula (I) Hemitartrate.

| Physical Characteristics | Formula (I) Free Base | Formula (I) Hemitartrate |
|---|---|---|
| Melting Point (° C.) | 86-88 | 163 |
| Endothermic enthalpy (J/g) | 75-82 | 96-106 |
| Particle size (μm) | <10 to 100 | ~3 (Average) |
| Aqueous solubility (mg/mL) | 0.04 | >216 |
| Crystalline | Yes | Yes |
| Crystal Shape | Needle | Plate, rod, some irregular |
| Hygroscopicity (40° C./75% RH) | None | None |
| Bulk Density | ~0.2 | 0.4-0.5 |

Example 6

In Vitro Activity and Specificity

Activity of Formula (I) Hemitartrate at inhibiting glycosphingolipid synthesis in vitro. Two assays were used to quantify the inhibitory activity of Formula (I) Hemitartrate for glucosylceramide synthase. Since glucosylceramide is the first and rate-limiting step in the biosynthesis of glycosphingolipids, a flow cytometry assay that measured cell surface levels of GM1 and GM3 was used to indirectly assess the activity of the inhibitor in intact cells. Incubating K562 or B16/F10 cells for 72 h with increasing amounts of Formula (I) Hemitartrate (0.6-1000 nM) resulted in a dose-dependent reduction of cell surface levels of both GM1 and GM3. The mean $IC_{50}$ value for inhibiting the cell surface presentation of GM1 in K562 cells was 24 nM (range 14-34 nM) (Table 8) and that for GM3 in B16/F10 cells was 29 nM (range 12-48 nM). No overt cellular toxicity was noted in either cell line even when tested at the highest dose.

An alternative assay for activity measured inhibition of glucosylceramide synthase in human cell derived microsomes. In this assay, microsomes were prepared from human melanoma A375 cells by sonication and centrifugation. The microsomal preparation was incubated with a fluorescent ceramide substrate (NBD-C6-ceramide), UDP-glucose, and increasing amounts of Formula (I) Hemitartrate (0-1000 nM) for one hour at room temperature. Following the incubation, fluorescently labeled glucosylceramide and unreacted ceramide were separated and quantitated by reverse-phase HPLC and fluorescence detection. In this assay the $IC_{50}$ value for inhibiting glucosylceramide synthesis ranged from 20 to 40 nM. This value was similar to those obtained above for GM1 and GM3 and suggests that measurements of these cell surface glycolipids are good surrogates of the activity of Formula (I) Hemitartrate for glucosylceramide synthase.

Specificity of substrate synthesis inhibition by Formula (I) Hemitartrate. The specificity of Formula (I) Hemitartrate was evaluated in a series of in vitro cell-based and cell-free assays. The intestinal glycosidase enzymes were assayed in rat tissue homogenates (see U. Andersson, et al., Biochem. Pharm. 59 (2000) 821-829, the entire teachings of which are incorporated herein by reference), and the glycogen debranching enzyme was assayed in a cell free assay as described (see U. Andersson, et al., Biochem. Pharm. 67 (2004) 697-705, the entire teachings of which are incorporated herein by reference). No detectable inhibition of intestinal glycosidases (lactase, maltase, sucrase), α-glucosidase I and II, and the cytosolic debranching enzyme (α-1,6-glucosidase), was found at concentrations up to 2500 μM (Table 8).

Non-lysosomal glucosylceramidase and lysosomal glucocerebrosidase were assayed in intact human cells using $C_6$-NBD-glucosylceramide as substrate (see H. S. Overkleeft, et al. J. Biol. Chem. 273 (1998) 26522-26527, the entire teachings of which are incorporated herein by reference). Conduritol β epoxide (a specific inhibitor of lysosomal glucocerebrosidase) was used to differentiate lysosomal versus the non-lysosomal activity. Glucocerebrosidase activity was also measured by fluorescence-activated cell sorting (FACS). K562 cells were cultured with increasing amounts of Formula (I) Hemitartrate in the presence of 1 μM 5-(pentafluorobenzoylamino)-fluorescein di-β-D-glucopyranoside (PFB-FDGlu, Molecular Probes/Invitrogen. Carlsbad, Calif.) for 30-60 min. Cells were immediately chilled on ice and the fluorescence quantitated is above. The non-lysosomal glucosylceramidase was weakly inhibited with an $IC_{50}$ of 1600 μM. There was no inhibition of lysosomal glucocerebrosidase, the enzyme that is deficient in Gaucher disease, up to the highest concentration of 2500 μM (Table 8). Hence, a differential of approximately 40,000 in the concentration was required to inhibit glucosylceramide synthase compared to any of the other enzymes tested.

TABLE 8

Biochemical activities Formula (I) Hemitartrate in vitro

| | |
|---|---|
| Substrate inhibition potency (in vitro $IC_{50}$): | ~0.024 μM |
| Enzyme specificities, $IC_{50}$: | |
| α-Glucosidase I and II: | >2500 μM |
| Lysosomal glucocerebrosidase (GBA1): | >2500 μM μM |
| Non-lysosomal glucosylceramidase (GBA2): | 1600 μM |
| Glycogen debranching enzyme: | >2500 μM |
| Enzyme specificities, $K_i$: | |
| Sucrase inhibition: | No inhib. to 10 μM |
| Maltase inhibition: | No inhib. to 10 μM |

Example 7

Improved Management of Lysosomal Glucosylceramide Levels in a Mouse Model

A. Fabry Disease.

To determine if the combined use of both enzyme replacement therapy (ERT) and substrate reduction therapy (SRT) may maintain enzyme debulking or provide additional benefits, the relative efficacies of separate and combined therapies in a murine model of Fabry disease (Fabry-Rag) were compared. The parental Fabry mice is described in Wang, A M et al. Am. J. Hum. Genet. 59: A208 (1996). The Fabry-Rag is crossed with a RAG-1 mouse and does not develop mature lymphocytes or T-cells (immune-compromised).

Animal Studies.

For the monotherapy studies, Fabry mice were put on study at 1 month old (prevention model). Treatment groups received Formula (I) Hemitartrate (Genzyme Corp., Cambridge, Mass.) as a component of the pellet food diet. The drug was formulated at 0.15% (w/w) in standard 5053 mouse chow (TestDiet, Richmond, Ind.) and provided ad libitum. This formulation provided 300 mg/kg of Formula (I) Hemitartrate per day in a 25 g mouse.

For the combination therapy studies, Fabry-Rag mice were put on study at 3 months old (treatment model). Mice in group A received intravenous injections of recombinant human alpha-galactosidase A (Genzyme Corp.) at a dose of 1 mg/kg every 2 months (i.e. 3, 5, 7 and 9 months old). Group B received the same intravenous enzyme doses plus it received Formula (I) Hemitartrate (Genzyme Corp., Cambridge, Mass.) as a component of the pellet food diet. The drug was formulated at 0.15% (w/w) in standard 5053 mouse chow (TestDiet, Richmond, Ind.) and provided ad libitum. This formulation provided 300 mg/kg of Formula (I) Hemitartrate per day in a 25 g mouse. Group C received enzyme injections every 4 months (i.e. 3 and 7 months old) and was on the same drug-in-food diet as group B. Group D received only the drug-in-food diet (same as groups B and C). Group E was untreated Fabry-Rag mice and group F were wild-type controls. See FIG. 10.

Quantitation of Tissue Globotriaosylceramide (GL-3, Gb3) Levels

Quantitation of GL-3 was by Tandem Mass Spectrometry essentially as for GL-1.

Hot plate Assay was performed as described previously (Ziegler, R J et al. *Molec. Ther.* 15(3), 492-500 (2007).

Results

Monotherapy of Fabry Mice with Formula (I) Hemitartrate

SRT was evaluated in a mouse model of Fabry disease, which is caused by a deficiency of α-galactosidase A activity. Therapy with Formula (I) Hemitartrate started with one month-old Fabry mice and continued until the mice reached one year of age. The animals were dosed with 300 mg/kg Formula (I) Hemitartrate in their diet each day. Behavioral tests (i.e., hot-plate assay) and biochemical tests (i.e., urinalysis and GL-3 level analysis in tissues/blood/urine) of the mice were performed bimonthly.

Figure 7:
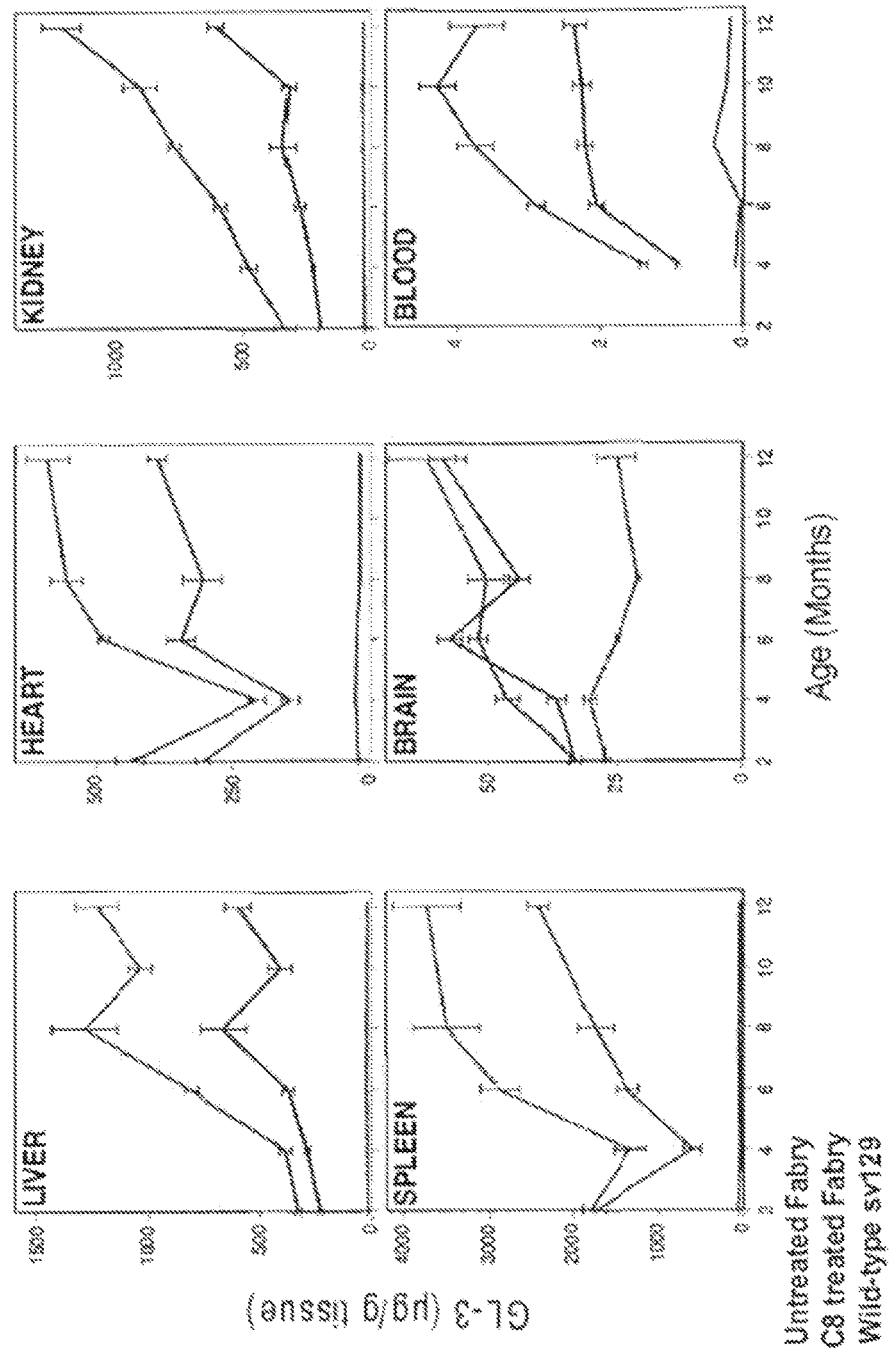
FIG. 7 shows the effect of Formula (I) Hemitartrate therapy on the accumulation of GL-3 in Fabry mouse liver, heart, kidney, spleen, brain, and blood.
Figure 8:
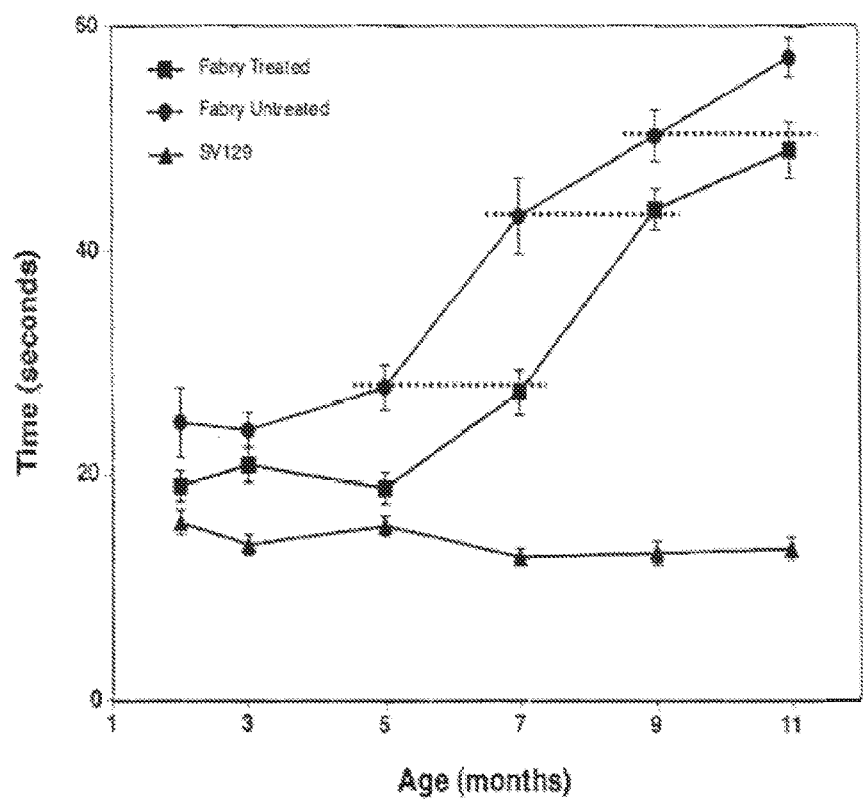
FIG. 8 shows a graph of the effect of Formula (I) Hemitartrate therapy on the onset and progression of peripheral neuropathy in Fabry mice.
Figure 9:
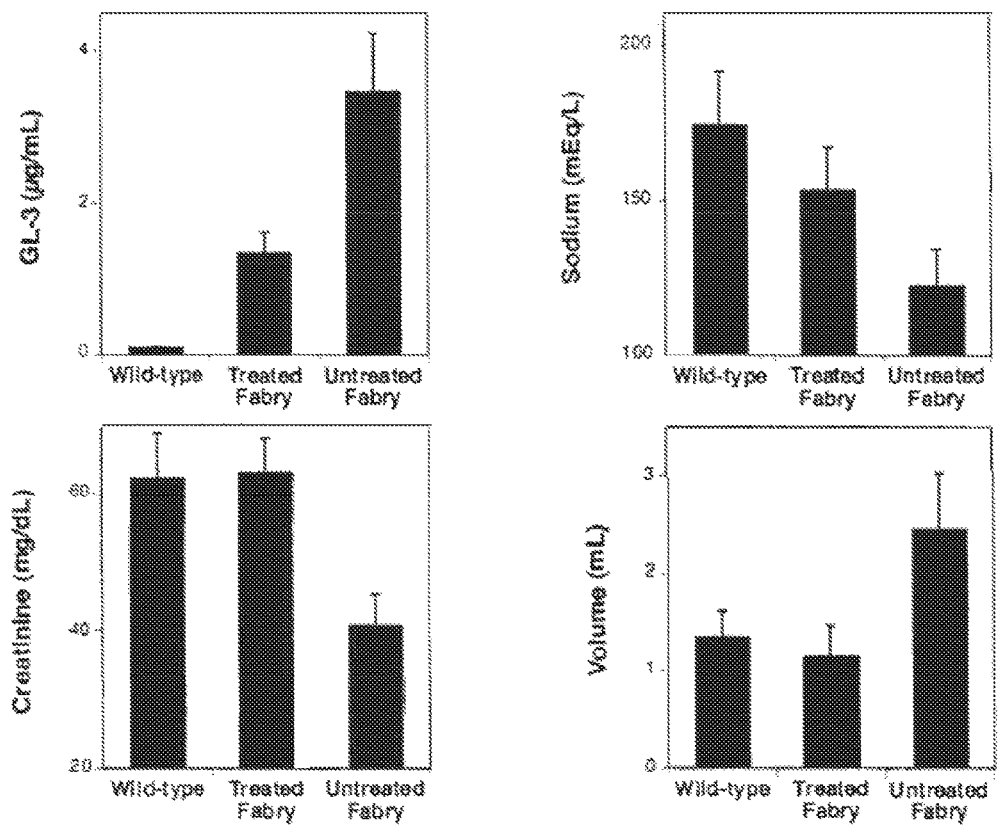
FIG. 9 shows graphs of measurements of some markers of kidney function in Fabry mice treated with Formula (I) Hemitartrate.

As shown in FIG. 7, administration of Formula (I) Hemitartrate to Fabry-Rag mice over a period of 11 months abated the rate of lysosomal accumulation of globotriaoslyceramide (GL-3) in the somatic organs (liver, kidney, heart and spleen) by approximately 50%. This translated to a delay in disease progression as evidenced by a later presentation of insensitivity to an aversive heat stimulus (see FIG. 8) and a prevention of deterioration of urinalysis factors, e.g., urine volume, creatinine and sodium levels (see FIG. 9). Hence, Formula (I) Hemitartrate-mediated inhibition of glucosylceramide synthase that catalyzes the first step in the synthesis of glycosphingolipids, is not only advantageous in animal models of Gaucher disease but also of Fabry disease, and could also have positive effects in other glycosphingolipidoses.

Figure 10:
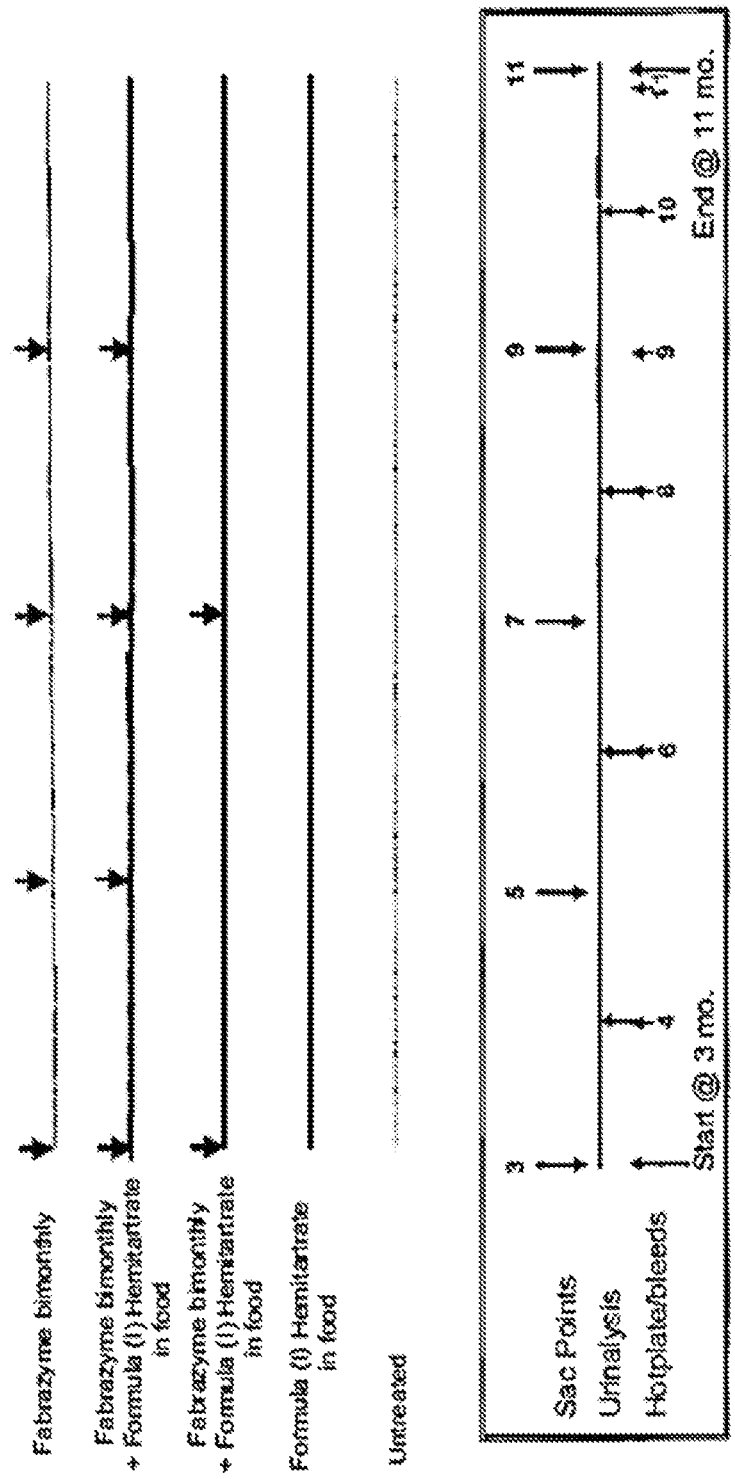
FIG. 10 shows a timeline for ERT and SRT studies of mouse populations receiving different drug therapies: A) Fabrazyme bimonthly, no Formula (I) Hemitartrate; B) Fabrazyme bimonthly and Formula (I) Hemitartrate in food; C) Fabrazyme administered at the beginning of the study and at month four of the study and Formula (I) Hemitartrate in food; D) no Fabrazyme, Formula (I) Hemitartrate in food; and E) no drug therapy.

Combination Therapy of Fabry Mice with α-Galactosidase A and Formula (I) Hemitartrate The efficacy of ERT alone and in combination with SRT using Formula (I) Hemitartrate was evaluated in five populations of Fabry-Rag mice (n=12/group). Beginning at three-months of age, the mice were subjected to a schedule of behavioral tests (i.e. hot-plate assay) and biochemical tests (i.e., GL-3 level analysis in tissues/blood/urine), as shown in FIG. 10. In mice subjected to ERT, 1 mg/kg doses of α-galactosidase A were administered on the schedule as shown in FIG. 10. In mice subjected to SRT, 300 mg/kg doses of Formula (I) Hemitartrate were administered daily in the mouse diet.

Figure 11:
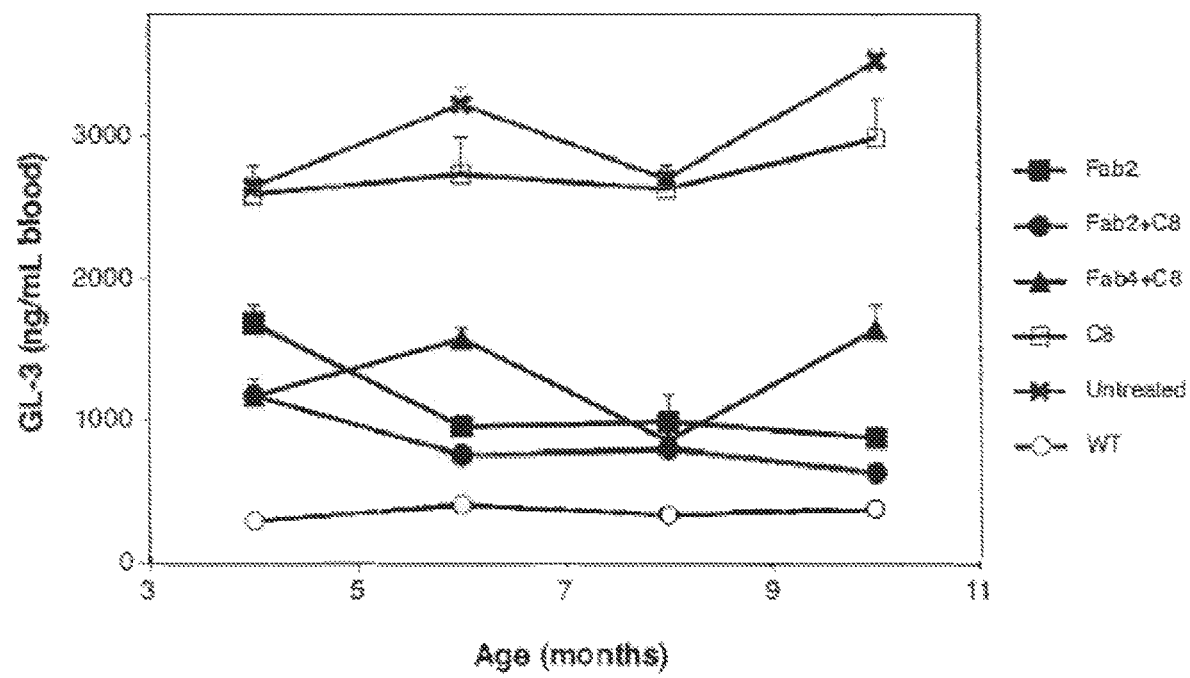
FIG. 11 shows graphs of blood GL-3 levels in ng/mL of blood in six populations (n=?) of mice (A-E Fabry-Rag; and F wild-type); the mice populations received the following therapies: A) Fabrazyme bimonthly, no Formula (I) Hemitartrate; B) Fabrazyme bimonthly and Formula (I) Hemitartrate in food; C) Fabrazyme administered at the beginning of the study and at month four of the study and Formula (I) Hemitartrate in food; D) no Fabrazyme, Formula (I) Hemitartrate in food; E) no drug therapy; and F) no drug therapy.
Figure 12:
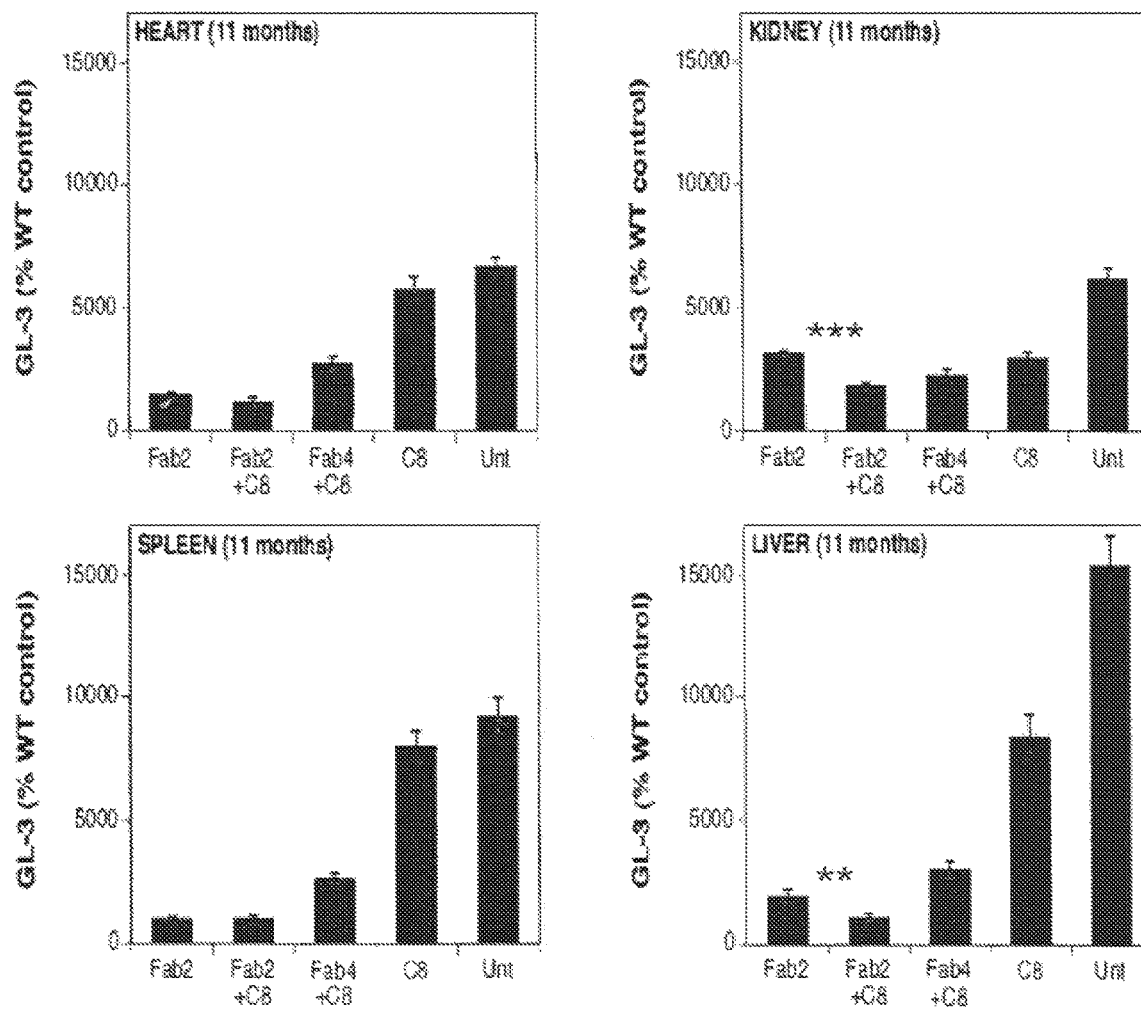
FIG. 12 shows graphs of GL-3 levels in Fabry-Rag mice liver and kidney; the mice populations (n=?) received the following therapies: A) Fabrazyme bimonthly, no Formula (I) Hemitartrate; B) Fabrazyme bimonthly and Formula (I) Hemitartrate in food; C) Fabrazyme administered at the beginning of the study and at month four of the study and Formula (I) Hemitartrate in food; D) no Fabrazyme, Formula (I) Hemitartrate in food; and E) no drug therapy

As shown in FIG. 11, ERT reduces blood GL-3 levels in Fabry-Rag mice, whereas SRT does not. As shown in FIG. 12, combination ERT/SRT is most effective at reducing GL-3 levels in Fabry-Rag mice liver and kidney.

Figure 13:
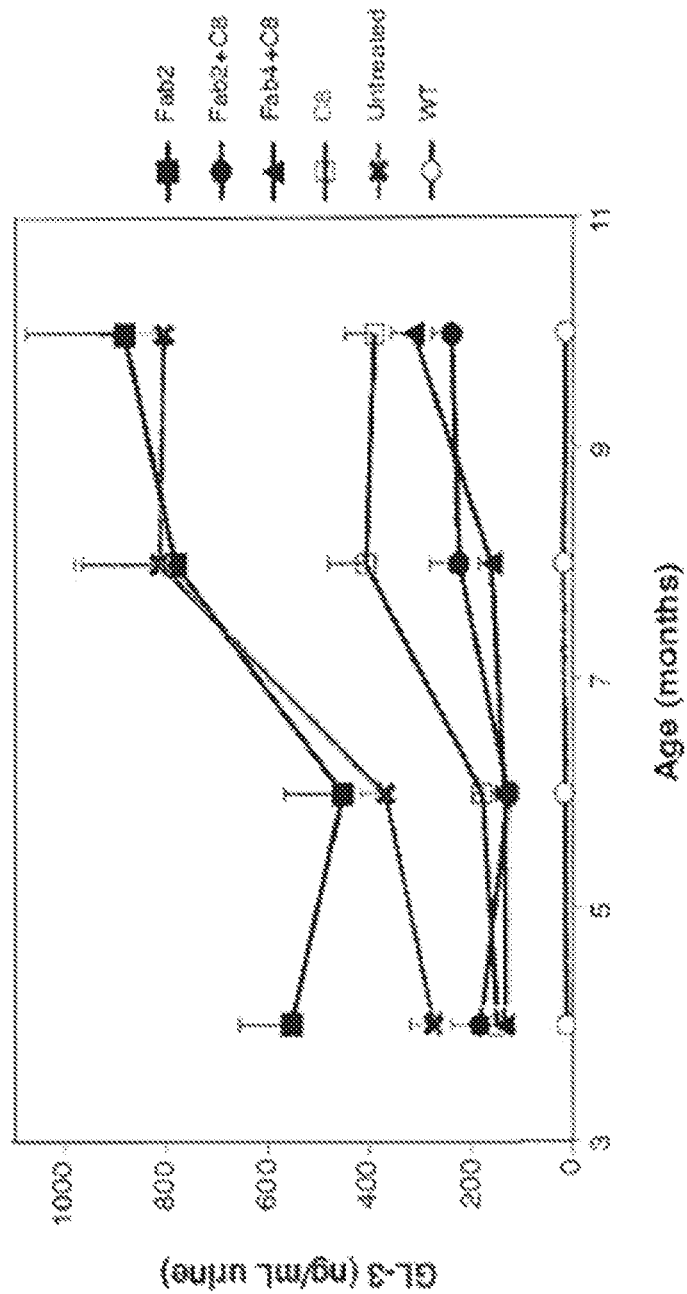
FIG. 13 shows graphs of urine GL-3 levels in Fabry-Rag mice; the mice populations (n=?) received the following therapies: A) Fabrazyme bimonthly, no Formula (I) Hemitartrate; B) Fabrazyme bimonthly and Formula (I) Hemitartrate in food; C) Fabrazyme administered at the beginning of the study and at month four of the study and Formula (I) Hemitartrate in food; D) no Fabrazyme, Formula (I) Hemitartrate in food; and E) no drug therapy.
Figure 14:
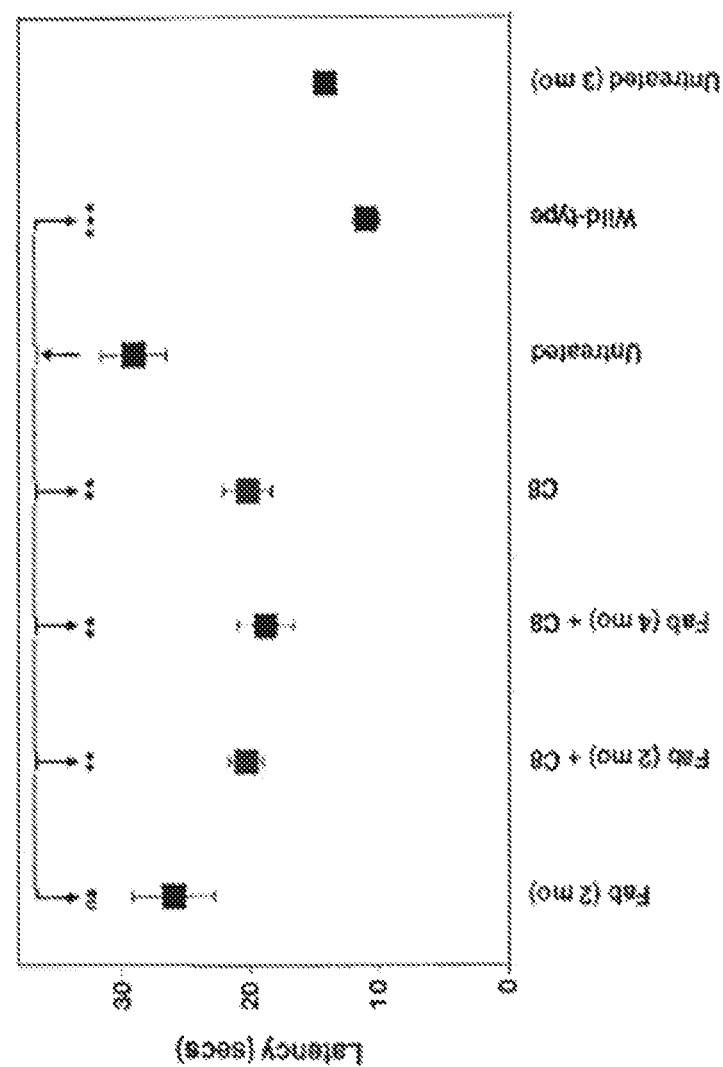
FIG. 14 is a graph showing the latency in seconds of heat sensitivity of Fabry-Rag mice receiving the following therapies: Fabrazyme bimonthly, no Formula (I) Hemitartrate; Fabrazyme bimonthly and Formula (I) Hemitartrate in food; Fabrazyme administered at the beginning of the study and at month four of the study and Formula (I) Hemitartrate in food; no Fabrazyme, Formula (I) Hemitartrate in food; no drug therapy; wild-type mice; and untreated at three months.

As shown in FIG. 13, SRT reduces urine GL-3 levels in Fabry-Rag mice, whereas ERT does not. As shown in FIG. 14, SRT but not ERT delays onset of heat-insensitivity in Fabry-Rag mice.

In summary, Fabry-Rag mice treated with a combination Fabrazyme and Formula (I) Hemitartrate exhibited improvements in disease markers over ERT or SRT alone in a treatment model in the following ways: significantly reduced liver and kidney GL-3 accumulation with combination therapy; improved urine GL-3 in SRT groups; improved blood GL-3 in ERT groups; and delayed peripheral neuropathy in SRT groups.

B. Gaucher disease. To determine if the sequential use of both enzyme replacement therapy (ERT) and substrate reduction therapy (SRT) may provide additional benefits, the relative efficacies of separate and sequential therapies in a murine model of Gaucher disease (D409V/null) were compared.

Methods

Animal studies. Procedures involving animals were reviewed and approved by the Institutional Animal Care and Use Committee (IACUC) at Genzyme Corporation following the guidelines issued by the Association for Assessment and Accreditation of Laboratory Animal Care (AAALAC).

The Gaucher mouse (D409V/null) is a model of type 1 Gaucher disease exhibiting accumulation of glucosylceramide in liver, spleen and lungs but lacks bone or brain pathology (see Y-H. Xu, et al., *Am. J. Pathol.* 163, 2003, 2093-2101, the entire teachings of which are incorporated herein by reference). Animals of both sexes were placed on study at 3 months of age as previous experiments had indicated that there was no difference in response between males and females to recombinant glucocerebrosidase or Formula (I) Hemitartrate. The study had 6 groups of mice with group A being sacrificed after 2 weeks to provide baseline levels of tissue glucosylceramide. Groups B, C, and D all received recombinant human glucocerebrosidase (Genzyme Corp., Cambridge, Mass.) (10 mg/kg) intravenously via a tail-vein (100 µL) every 2 days for a total of 8 injections. Group B was sacrificed at the end of this regimen (at the same time as group A) to provide enzyme-reduced levels of tissue glucosylceramide. Groups D and E were both fed Formula (I) Hemitartrate (Genzyme Corp., Cambridge, Mass.) as a component of the pellet food diet. The drug was formulated at 0.075% (w/w) in standard 5053 mouse chow (TestDiet, Richmond, Ind.) and provided ad libitum. This formulation provided 150 mg/kg of Formula (I) Hemitartrate per day in a 25 g mouse. Group F received no treatment and was sacrificed along with groups C, D and E 12 weeks after the start of the study. Food consumption and mouse weights were monitored three times per week to determine drug intake and the potential impact of the drug on overall health. Animals were killed by carbon dioxide inhalation and their tissues harvested immediately. Half of each tissue was snap frozen on dry ice and stored at −80° C. until ready for further processing. The other half was processed for histological analysis.

Quantitation of tissue glucosylceramide levels Glucosylceramide levels were quantified by mass spectrometry as described previously (see K. McEachern, et al., *J. Gene. Med.* 8 (2006) 719-729; T. Doering, *J. Biol. Chem.* 274 (1999) 11038-11045, the entire teachings of both are incorporated herein by reference). A known mass of tissue was homogenized in 2:1 (v/v) chloroform:methanol and incubated at 37° C. for 15 min. Samples were centrifuged and the supernatants were extracted with 0.2 volumes of water overnight at 4° C. The samples were centrifuged, the aqueous phase was discarded, and the organic phase was dried down to a film under nitrogen. For electrospray ionization mass spectrometry (ESI/MS) analysis, tissue samples were reconstituted to the equivalent of 50 ng original tissue weight in 1 ml chloroform:methanol (2:1, v/v) and vortexed for 5 min. Aliquots (40 µL) of each sample were delivered to Waters total recovery vials and 50 µL of a 10 µg/mL d3-C16-GL-1 internal standard (Matreya, Inc., Pleasant Gap, Pa.) was added. Samples were dried under nitrogen and reconstituted with 200 µL of 1:4 (v/v) DMSO:methanol. ESI/MS analysis of glucosylceramides of different carbon chain lengths was performed on a Waters alliance HPLC (Separation Module 2695) coupled to a Micromass Quattro Micro system equipped with an electrospray ion source. Lipid extract samples (20 µL) were injected onto a C8 column (4 mL×3 mm i.d; Phenomenex, Torrance, Calif.) at 45° C. and eluted with a gradient of 50 to 100% acetonitrile (2 mM ammonium acetate, 0.1% formic acid) at 0.5 mL/min. The first 0.5 min was held at 50% organic and then quickly switched to 100% for the final 3.5 min. The source temperature was held constant at 150° C. and nitrogen was used as the desolvation gas at a flow rate of 670 L/h. The capillary voltage was maintained at 3.80 KV with a cone voltage of 23 V, while the dwell time for each ion species was 100 ms. Spectra were acquired by the MRM mode to monitor eight dominant isoforms (C16:0, C18:0, C20:0, C22:1, C22:0, C22:1-OH, C24:1, and C24:0). Quantitation of glucosylceramide was based on the sum of these eight isoforms relative to the internal standard, with a calibration curve ranging from 0.1 to 10 µg/mL.

Histology. For histological analysis, tissues were fixed in zinc formalin (Electron Microscopy Sciences, Hatfield, Pa.) at room temperature for 24 h, then stored in PBS at 4° C. until ready for further processing. All samples were dehydrated in ethanol, cleared in xylenes, infiltrated and embedded in Surgipath R paraffin (Surgipath, Richmond, Ill.). Five micron sections were cut using a rotary microtome and dried in a 60° C. oven prior to staining. Sections were deparaffinized in Hemo-De (Scientific Safety Solvents, Keller, Tex.) and rehydrated in descending concentrations of ethanol followed by a PBS wash. The sections were stained with Hematoxylin and Eosin (H&E) and labeled using a rat anti-mouse CD68 monoclonal antibody (Serotec, Raleigh, N.C.) to identify macrophages. After washing for 5 min in PBS, the slides were dehydrated in ethanol and cleared in Hemo-De prior to mounting with SHUR/Mount™ coverglass mounting medium (TBS, Durham, N.C.). The percent area of CD68 immunopositivity in the liver was quantified using MetaMorph (MDS Analytical Technologies, Toronto, Canada) analysis of ten 400× images per tissue section. A board certified veterinary pathologist blinded to group designation examined all the sections.

Results

Dosing regimen of glucocerebrosidase for debulking accumulated GL1 in the liver, spleen and lung of 3 month-old Gaucher mice. To investigate the relative merits of combination and monotherapy with either enzyme or substrate reduction therapy, the enzyme regimen that maximally depleted GL1 levels in the visceral organs of Gaucher mice was first determined. Three month-old Gaucher mice (D409V/null) were intravenously administered 2, 4 or 8 doses of 10 mg/kg recombinant human glucocerebrosidase. The mice that were treated with 2 or 4 doses of the enzyme received drug infusions every 3 days while those that were treated with 8 doses received the enzyme every 2 days. The use of a shorter time interval between infusions in animals that received 8 treatments was designed to minimize the potential impact of any immune response to the administered human enzyme. The animals were killed 7 days following the last enzyme infusion and the amount of GL1 remaining in their livers, spleens, and lungs were measured.

Treatment with 2 doses of glucocerebrosidase reduced the levels of GL1 in the liver by 50%. Increasing the number of enzyme infusions to 4 or 8, as expected, reduced the liver GL1 levels to a greater extent (by approximately 75%). The less than complete lowering of GL1 levels, even with 8 doses, is consistent with the experience in Gaucher subjects showing that hepatosplenomegaly is reduced only after an extended period of treatment (see G. A. Grabowski, et al., Ann. Int. Med. 122 (1995) 33-39, the entire teachings of which are incorporated herein by reference). The substrate levels in the spleens of Gaucher mice were more refractory to enzyme treatment. Administration of 2 doses of glucocerebrosidase did not significantly alter GL1 levels from those noted in untreated controls. Increasing the number of enzyme infusions to 4 or 8 reduced the splenic GL1 levels by about 50%. In the lung, a reduction to approximately 60% of untreated control was observed after 8 doses. The slightly lower extent of substrate reduction in the lung was probably due to poorer accessibility of the infused enzyme to the lipid-laden alveolar macrophages. The observation of greater GL1 clearance in the liver when compared with the spleen and lung likely reflects the biodistribution of the enzyme following systemic infusion (see S. M. Van Patten, et al. Glycobiology 17 (2007) 467-478, the entire teachings of which are incorporated by reference). Based on these results, the treatment regimen consisting of 8 consecutive doses of 10 mg/kg glucocerebrosidase administered at 2 days intervals was used for the subsequent studies.

Figure 2:
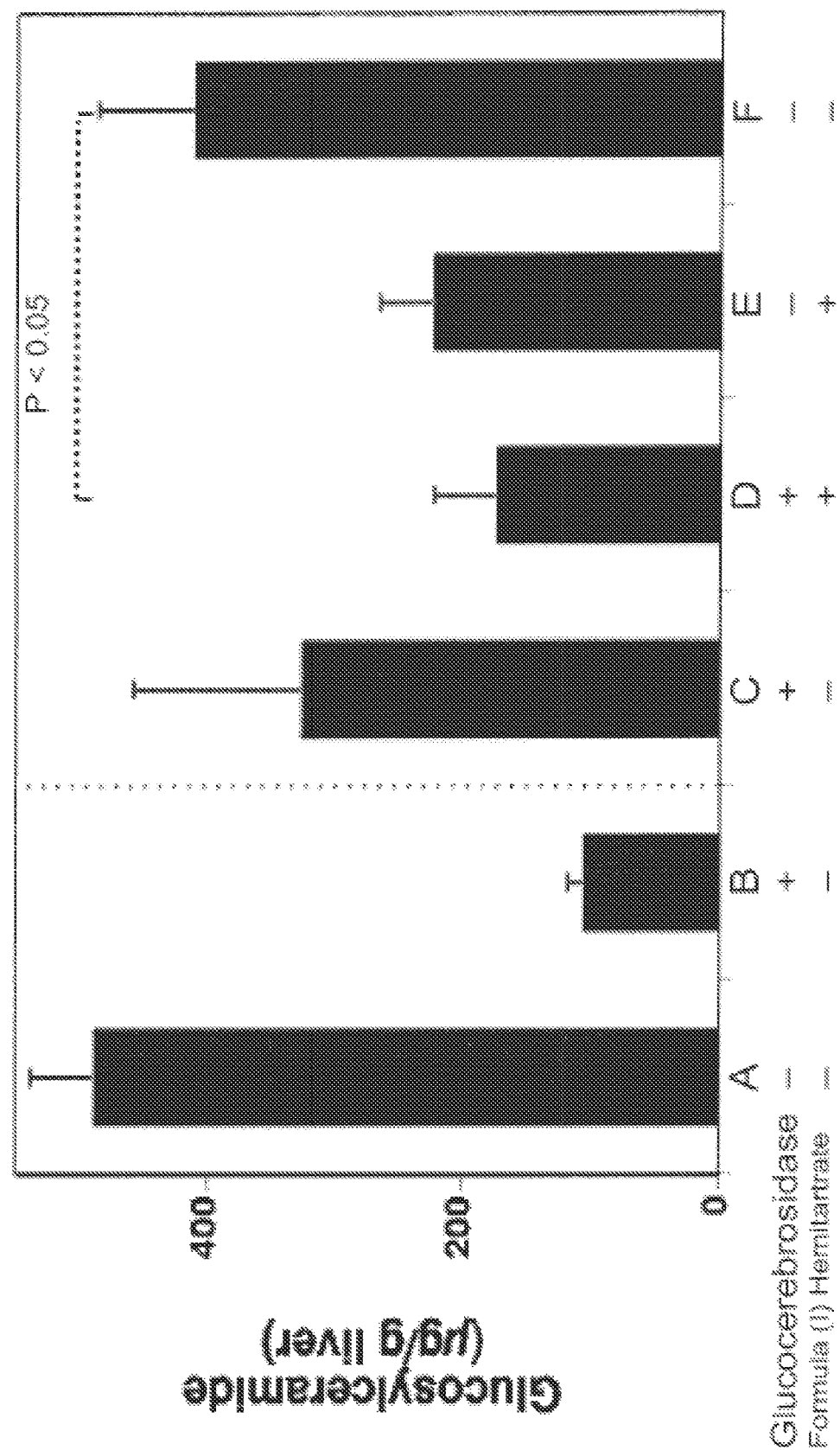
FIG. 2 is a graph of the efficacy of enzyme and substrate reduction therapies at lowering glucosylceramide levels in the liver of Gaucher mice. Liver GL1 levels were measured in untreated 3 month-old Gaucher mice (A) and following 2 weeks of treatment with recombinant glucocerebrosidase (B). Mice treated with recombinant glucocerebrosidase were analyzed 10 weeks later without further treatment (C) or after therapy with Formula (I) Hemitartrate (D) at 150 mg/kg feed. GL1 levels in the liver of mice administered Formula (I) Hemitartrate alone for the entire period of study (E) and in untreated, age-matched controls (F) are also shown. Data are expressed as means±standard error of the mean (SEM) (1=5). Statistical significance was determined using the unpaired t test.

Relative abilities of enzyme and substrate reduction therapy to lower GL1 levels in the liver of Gaucher mice. Cohorts of 3-month-old Gaucher mice were treated with either recombinant glucocerebrosidase or Formula (I) Hemitartrate separately or sequentially. Mice in groups B, C and D were given 8 doses of enzyme as described above (over a period of 2 weeks) to clear accumulated GL1. Different groups were then fed either regular chow or chow containing Formula (I) Hemitartrate (150 mg/kg/day) for an additional 10 weeks with group F receiving no treatment and serving as the naïve control. Irrespective of the chow formulation, the mice ate comparable amounts of food and there were no discernible differences in weight gain. Approximately 80% of the stored GL1 levels were cleared from the liver following 2 weeks of enzyme therapy alone. When these animals were allowed to progress without further treatment for 10 weeks, their liver GL1 levels increased indicating that re-accumulation of the substrate had occurred during the intervening period (FIG. 2, column C). These levels were not significantly different from those of untreated controls (FIG. 2, column F). However, if the mice were treated with enzyme and then Formula (I) Hemitartrate in their food over a 10 week period, their liver GL1 levels were significantly lower than the untreated controls (FIG. 2, column D & F). This result suggests that the additional treatment with Formula (I) Hemitartrate had slowed the re-accumulation of the substrate. Interestingly, Gaucher mice treated with Formula (I) Hemitartrate alone during the entire study period (12 weeks) also showed lower GL-1 levels (FIG. 2, column E) when compared to untreated, age-matched controls (FIG. 2, column F) though the difference was not significant. The ability of SRT alone to reduce GL1 levels in this animal model is consistent with our previous report (see K. A. McEachern, et al., Mol. Genet. Metab. 91 (2007) 259-267, the entire teachings of which are incorporated herein by reference) and likely reflects the fact that the Gaucher mice (D409V/null) retain residual enzymatic activity (see Y-H. Xu, et al., *Am. J. Pathol.* 163, 2003, 2093-2101, the entire teachings of which are incorporated herein by reference).

Figure 3:
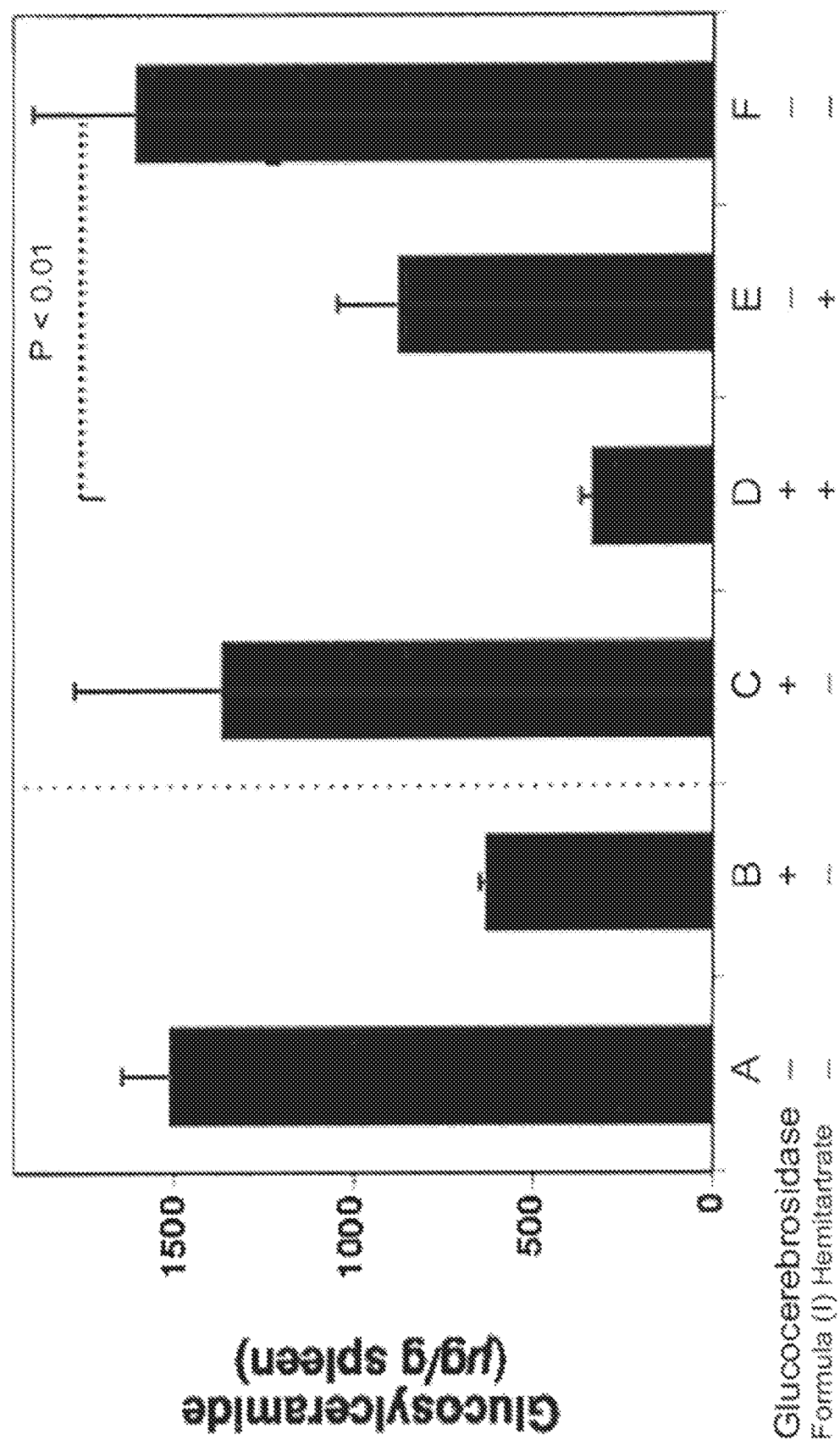
FIG. 3 is a graph of the efficacy of enzyme and substrate reduction therapies at lowering glucosylceramide levels in the spleen of Gaucher mice. Spleen GL1 levels were measured in untreated 3 month-old Gaucher mice (A) and following 2 weeks of treatment with recombinant glucocerebrosidase (B). Mice treated with recombinant glucocerebrosidase were analyzed 10 weeks later without further treatment (C) or after therapy with Formula (I) Hemitartrate (D). GL1 levels in the spleen of mice administered Formula (I) Hemitartrate alone for the entire period of study (E) and in untreated, age-matched controls (F) are also shown. Data are expressed as means±standard error of the mean (SEM) (n=5). Statistical significance was determined using the unpaired t test.

Relative abilities of enzyme and substrate reduction therapy to lower GL1 levels in the spleen of Gaucher mice. Treating 3 month-old Gaucher mice with recombinant glucocerebrosidase alone for 2 weeks reduced splenic GL1 levels by approximately 60% (FIG. 3, column B). When these animals were allowed to age for an additional 10 weeks without further intervention, the substrate levels returned to those observed at the start of the study (FIG. 3, column C) and were not significantly different from the untreated control (FIG. 3, column F). This suggests that the rate of re-accumulation of GL1 in the spleen was higher than in the liver. This supposition was also supported by the observation of higher basal levels of the substrate in the spleen (~1500 mg/g tissue; FIG. 2, column A) than in the liver (~500 mg/g tissue; FIG. 3, column A). Animals that had been treated with enzyme and then Formula (I) Hemitartrate for the next 10 weeks showed the greatest reduction in splenic GL1 levels (FIG. 3, column D) and these were significantly lower than those in the untreated control spleens (FIG. 3, column F). This indicated that the deployment of SRT not only delayed the re-accumulation of substrate but also acted to further reduce the burden of storage in this organ. It would appear that at least in this instance, the net effect of the residual endogenous enzyme and substrate reduction led to a further decline in overall substrate levels. The observation of lower splenic GL1 levels in the mice treated with Formula (I) Hemitartrate alone for 12 weeks (FIG. 3, column E) than in untreated controls (FIG. 3, column F) is consistent with this notion, though the difference was not significant. Hence, in mild Gaucher type 1 patients with high residual enzyme activity, treatment with ERT followed by SRT could potentially accelerate the rate and perhaps even the extent of clearance of the offending substrate.

Figure 4:
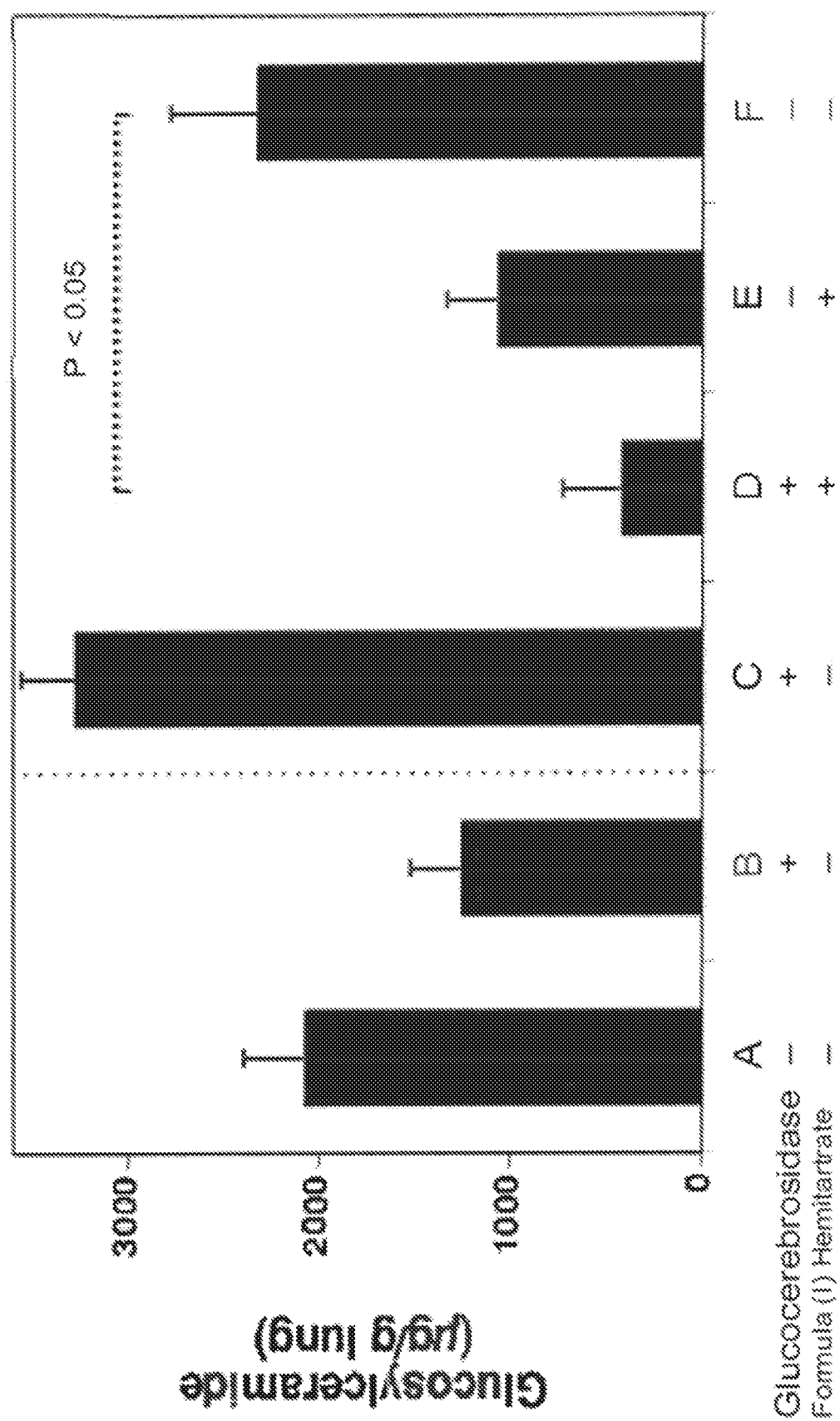
FIG. 4 is a graph of the efficacy of enzyme and substrate reduction therapies at lowering glucosylceramide levels in the lung of Gaucher mice. Lung GL1 levels were measured in untreated 3 month-old Gaucher mice (A) and following 2 weeks of treatment with recombinant glucocerebrosidase (B). Mice treated with recombinant glucocerebrosidase were analyzed 10 weeks later without further treatment (C) or after therapy with Formula (I) Hemitartrate (D). GL1 levels in the lung of mice administered Formula (I) Hemitartrate alone for the entire period of study (E) and in untreated, age-matched controls (F) are also shown. Data are expressed as means±standard error of the mean (SEM) (n=5). Statistical significance was determined using the impaired t test.
Figure 5:
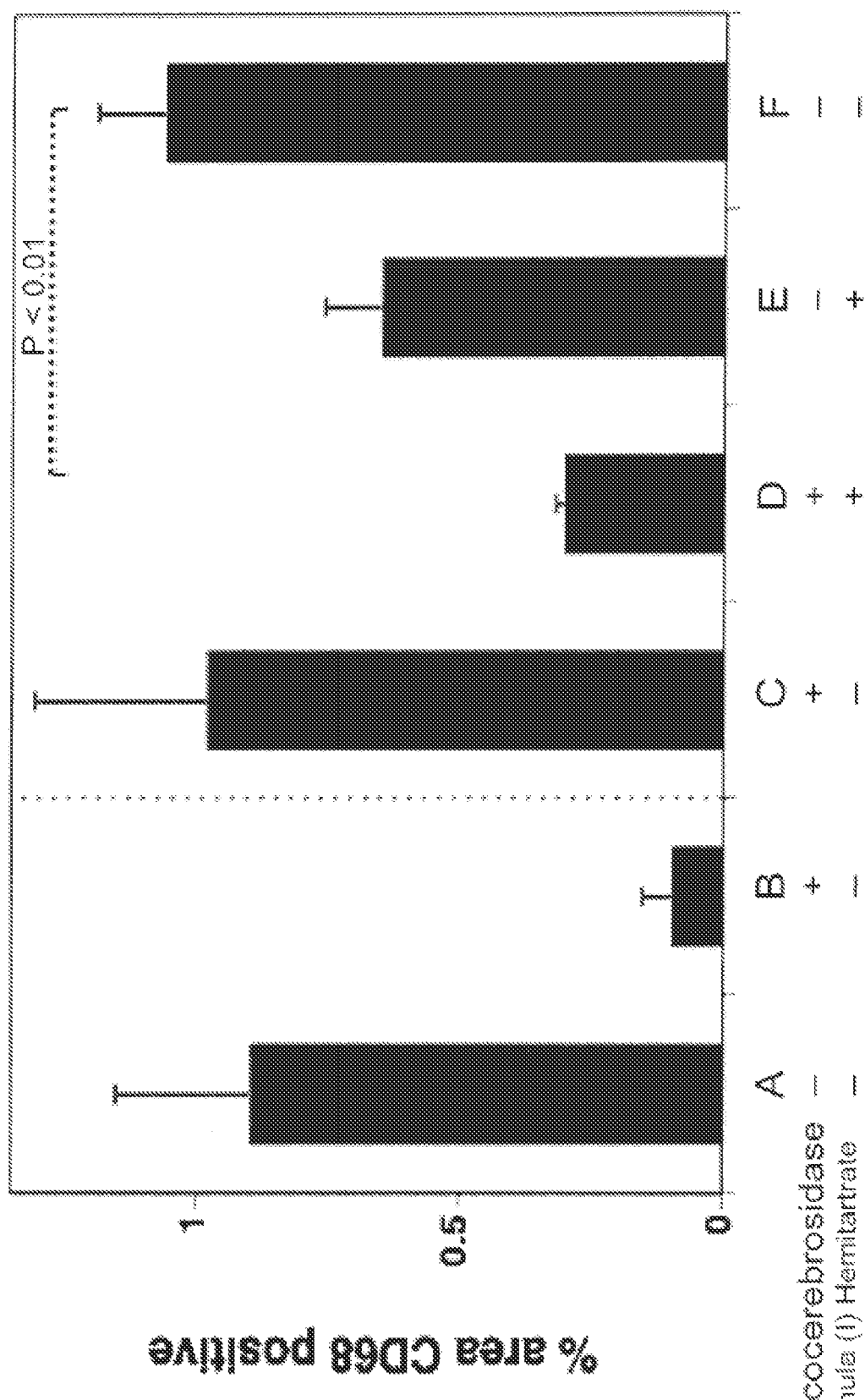
FIG. 5 is a graph showing the quantitation of the extent of CD68 staining in the liver. The extent of CD68-positive staining on the liver sections was quantified using MetaMorph software. Shown are levels in untreated 3 month-old Gaucher liver (A) or following treatment with glucocerebrosidase (B). Mice treated with enzyme and then analyzed 10 weeks later without further therapeutic intervention (C) or after therapy with Formula (I) Hemitartrate (D) are also illustrated. The extent of staining in the liver of Gaucher mice administered Formula (I) Hemitartrate alone (E) and in untreated, age-matched control mice (F) are also shown. The data was collated from an analysis of ten 400× images per section from each of the mice. Statistical significance was determined using the unpaired t test.

Relative abilities of enzyme and substrate reduction therapy to lower GL1 levels in the lung of Gaucher mice. As noted earlier, pulmonary GL1 levels were least effectively cleared by intravenous administration of recombinant glucocerebrosidase. Treatment of 3 month-old Gaucher mice with enzyme for 2 weeks resulted in only a 30% reduction in substrate levels in the lung (FIG. 4, column B). The cohort of animals fed normal chow for the next ensuing 10 weeks showed, as expected, re-accumulation of GL1 and were not significantly different from the untreated levels (FIG. 4, column C & F). In contrast, animals fed chow containing Formula (I) Hemitartrate over the same intervening period showed a reduction in substrate levels to below those administered enzyme alone (FIG. 4, column D) and were significantly lower than those in the untreated controls (FIG. 4, column F). Again, this suggests that in the lung, as in the spleen, the net effect of Formula (I) Hemitartrate (in the presence of residual endogenous enzyme activity) not only retarded the re-accumulation of GL1 but also acted to further reduce them to below the starting levels. As with the other visceral organs, treatment by Formula (I) Hemitartrate alone was effective in lowering pulmonary GL1 levels (FIG. 4, column E) when compared to untreated controls (FIG. 4, column F).

Histopathological analysis of the liver of Gaucher mice after enzyme and substrate reduction treatment. To visualize the effects of the different therapeutic regimens in the liver, tissue sections were stained for CD68, a macrophage marker. Analysis of liver sections from untreated 3 month-old Gaucher mice showed the presence of large numbers of lipid-engorged, CD68-positive Gaucher cells that remained largely unchanged when analyzed 12 weeks later. Consistent with the biochemical data above, livers of animals administered recombinant glucocerebrosidase over a period of 2 weeks showed substantial clearance of the lipid in these abnormal macrophages. If these animals were allowed to age an additional 10 weeks without further treatment, there was evidence of re-accumulation of GL1 as indicated by the re-emergence of Gaucher cells. However, this increase in Gaucher cells was negated if the mice were given substrate reduction therapy with Formula (I) Hemitartrate over the same intervening period. As noted earlier, Gaucher mice that received Formula (I) Hemitartrate alone also showed reduced accumulation of the substrate, although not to the same degree as those that received a combination of ERT and SRT. The extent of CD68-positive staining on the various sections was also quantified using MetaMorph software (FIG. 18). The degree of staining in these sections mirrored the amounts of liver GL1 levels determined biochemically (FIG. 15) further supporting the suggestions on the relative merits of the different treatment regimens.

Example 8

Efficacy of Formula (I) Hemitartrate in a Mouse Model of Gaucher Disease

Animal studies. Procedures involving animals were reviewed and approved by an Institutional animal care and use committee (IACUC) following Association for assessment and accreditation of laboratory animal care (AAALAC), State and Federal guidelines. The Gaucher gba$^{D409V/null}$ mice (See Y.-H. Xu. et al., Am. J. Pathol. 163 (2003) 2093-2101, the entire teachings of which are incorporated herein by reference) were allowed to mature according to study requirements. No difference in phenotype or response to Formula (I) Hemitartrate has been found between males and females, so both sexes were used in the studies. Formula (I) Hemitartrate delivery was by a single daily oral gavage at a volume of 10 mL/kg. Animals were acclimated to oral gavaging with a similar volume of water for one week prior to initiation of treatment. Formula (I) Hemitartrate was dissolved in Water For Injection (WFI; VWR, West Chester, Pa.) and administered in a dose escalation from 75 mg/kg/day to 150 mg/kg/day over the course of nine days, with three days at each dose and increments of 25 mg/kg/day. Mice were weighed three times per week to monitor the potential impact of the drug on their overall health. Animals were killed by carbon dioxide inhalation and their tissues harvested immediately. Half of each tissue was snapped frozen on dry ice and stored at −80° C. until ready for further processing. The other half was collected for histological analysis.

Quantitation of tissue glucosylceramide levels by high performance thin layer chromatography. High performance thin layer chromatography (HP-TLC) analysis were as described (A. Abe, et al., J. Clin. Inv. 105 (2000) 1563-1571; H. Zhao, et al. Diabetes 56 (2007) 1341-1349; and S. P. F. Miller, et al. J. Lab. Clin. Med. 127 (1996) 353-358, the entire teachings of each are incorporated herein by reference). Briefly, a total lipid fraction was obtained by homogenizing tissue in cold PBS, extracting with 2:1 (v/v) chloroform:methanol, and sonicating in a water bath sonicator. Samples were centrifuged to separate the phases and the supernatant was recovered. The pellets were re-sonicated in chloroform:methanol:saline, centrifuged and the resulting second supernatant was collected and combined with the first. A 1:1 (v/v) chloroform:saline mixture was aided to the combined supernatants, vortexed, and centrifuged. After discarding the upper aqueous layer, methanol:saline was added, vortexed and re-centrifuged. The organic phase was taken and dried under nitrogen, dissolved in 2:1 (v/v) chloroform:methanol at 1 mL per 0.1 g original tissue weight and stored at −20° C.

A portion of the lipid extract was used to measure total phosphate, (See B. N. Ames, Methods Enzymol. 8 (1966) 115-118, the entire teachings of which are incorporated herein by reference), i.e., the phospholipid content to use as an internal standard. The remainder underwent alkaline methanolysis to remove phospholipids that migrate with glucosylceramide on the HP-TLC plate. Aliquots of the extracts containing equivalent amounts of the total phosphate were spotted onto a HP-TLC plate along with known glucosylceramide standards (Matreya inc. Pleasant Gap, Pa.). The lipids were resolved and visualized with 3% cupric acetate monohydrate (w/v). 15% phosphoric acid (v/v) followed by baking for 10 min at 150° C. The lipid bands were scanned on a densitometer (GS-700, Bio-Rad, Hercules, Calif.) and analyzed by Quantity One software (Bio-Rad).

Quantitation of tissue glucosylceramide levels by mass spectrometry. Glucosylceramide was quantified by mass spectrometry as described. (See K. McEachern, et al. J. Gene Med. 8 (2006) 719-729; T. Doering, et al., J. Biol. Chem. 274 (1999) 11038-11045, the entire teachings of each are incorporated herein by reference). Tissue was homogenized in 2:1 (v/v) chloroform:methanol and incubated at 37° C. Samples were centrifuged and the supernatants were extracted with 0.2 volumes of water overnight. The samples were centrifuged again, the aqueous phase was discarded, and the organic phase dried down to a film under nitrogen.

For electrospray ionization mass spectrometry (ESI/MS) analysis, tissue samples were reconstituted to the equivalent of 50 ng original tissue weight in 1 mL chloroform/methanol (2:1, v/v) and vortexed for 5 min. Aliquots of each sample (40 µL) were delivered to Waters total recovery vials and 50 µL a 10 µg/mL d3-C16-GL-1 internal standard (Matreya, Inc., Pleasant Gap, Pa.) was added. Samples were dried under nitrogen and reconstituted with 200 µL of 1:4 DMSO:methanol. ESI/MS analysis of glucosylceramides of different carbon chain lengths was performed on a Waters alliance HPLC (Separation Module 2695) coupled to a Micromass Quattro Micro system equipped with an electrospray ion source. Twenty microliter lipid extract samples were injected on a C8 column (4 ml×3 mm i.d; Phenomenex, Torrance, Calif.) at 45° C. and eluted with a gradient of 50-100% acetonitrile (2 mM ammonium acetate, 0.1% formic acid) at 0.5 mL/min. The first 0.5 min are held at 50% organic and then quickly switched to 100% for the final 3.5 min. The source temperature was held constant at 150° C. and nitrogen was used as the desolvation gas at a flow rate of 670 L/h. The capillary voltage was maintained at 3.80 KV with a cone voltage of 23 V, while the dwell time for each ion species was 100 ms. Spectra were acquired by the MRM mode to monitor eight dominant isoforms (C16:0, C18:0, C20:0, C22:1. C22:0. C22:1-OH, C24:1, and C24:0). Quantitation of glucosylceramide is based on the sum of these eight isoforms to the internal standard, with a calibration curve range from 0.1 to 10 µg/mL.

Histology. For histological analysis, tissues were fixed in zinc formalin (Electron Microscopy Sciences, Hatfield, Pa.) at room temperature for 24 h, then stored in PBS at 4° C. until ready for further processing. All samples were dehydrated in ascending concentrations of alcohol, cleared in xylenes and infiltrated and embedded in Surgipath R paraffin (Surgipath, Richmond, Ill.). Five micron sections were cut using a rotary microtome and dried in a 60° C. oven prior to staining. Sections were deparaffinized in xylenes, and rehydrated in descending concentrations of alcohol followed by a water wash. After a 1 min rinse in 3% acetic acid, slides were stained for 40 min in 1% Alcian Blue 8GX (Electron Microscopy Sciences) in 3% acetic acid pH 2.0. After rinsing in water and oxidizing in 1% periodic acid for 1 min. slides were stained with Schiff's reagent (Surgipath) for 12 min. After washing for 5 min in hot water, the slides were dehydrated in alcohol and cleared in xylenes prior to mounting with SHUR/Mount™ coverglass mounting medium (TBS, Durham, N.C.). Gaucher cells identified morphologically in the liver were quantified using a manual cell count per 10 high power fields (HPFs, 400×).

Results

Effect of administering of Formula (I) Hemitartrate to D409V/null mice. The effect of administering Formula (I) Hemitartrate to D409V/null mice was assessed. Approximately 7-month-old mice were administered 150 mg/kg/day Formula (I) Hemitartrate (a dose shown in preliminary studies to be effective at inhibiting glucosylceramide synthase) by oral gavage for 10 weeks. This treatment had no notable effects on the well-being or feeding habits of the mice. Measurements of their body weight throughout the study showed no significant deviation from those of untreated mice suggesting that Formula (I) Hemitartrate was well tolerated at a dose shown to be effective at inhibiting the synthase.

Figure 6:
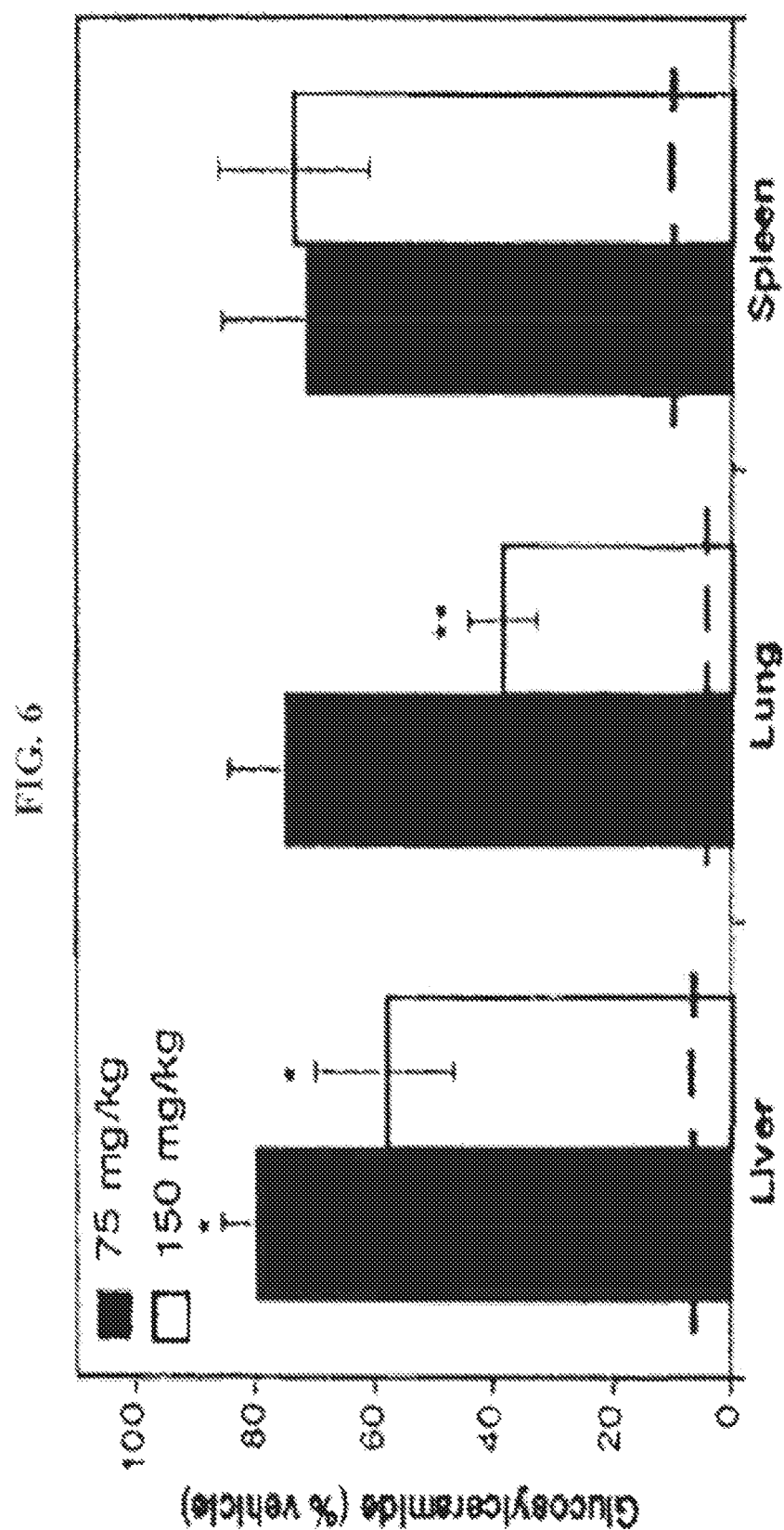
FIG. 6 is a graph that shows the efficacy of Formula (I) Hemitartrate in young D409V/null mice. Formula (I) Hemitartrate was administered to 10-week-old D409V/null mice daily by oral gavage at a dose of 75 or 150 mg/kg for 10 weeks. Glucosylceramide levels in liver, lung, vasculature and spleen were evaluated at the end of the study by HP-TLC. Data are presented as a percentage of GL-1 in untreated age-matched control mice. Dashed lines indicate glucosylceramide levels observed in normal wild type mice. $*p<0.05$; $**p<0.01$ relative to untreated control (two-tailed, unpaired t-test). Data are represented as means+standard error of the mean (SEM) n=5 for 75 mg/kg; n=6 for 150 mg/kg).

Efficacy of Formula (I) Hemitartrate at treating young, pre-symptomatic Gaucher, mice. Formula (I) Hemitartrate was evaluated for abatement of the lysosomal accumulation of glucosylceramide and the appearance of Gaucher cells in young (10-week old) D409V/null mouse. These young Gaucher mice exhibit low levels of GL-1 in the affected tissues. Ten-week-old animals were administered either 75 or 150 mg/kg/day of Formula (I) Hemitartrate by oral gavage for 10 weeks. Measurement of glucosylceramide levels showed a dose-dependent reduction when compared to age-matched vehicle-treated controls. In the cohort that had been treated with 150 mg/kg/day, glucosylceramide levels were 60, 40 and 75% of those in the controls, in the liver, lung and spleen, respectively (FIG. 6). The statistically significantly lower levels of glucosylceramide observed in the liver and lung of treated D409V/null mice indicated that Formula (I) Hemitartrate was effective at reducing the accumulation of this glycosphingolipid in these tissues.

Histopathological evaluation of the livers of untreated D409V/null mice at the end of the study (20 weeks of age) showed the presence of Gaucher cells throughout the liver. Mice treated with 150 mg/kg/day of Formula (I) Hemitartrate for 10 weeks showed only the occasional presence of Gaucher cells that were also invariably smaller in size. Quantitation of these cells in a number of different sections confirmed that the frequency of Gaucher cells were significantly lower in the Formula (I) Hemitartrate-treated mice. Together, these biochemical and histological findings suggested that daily oral administration of Formula (I) Hemitartrate to pre-symptomatic Gaucher mice was effective at decreasing the accumulation of glucosylceramide in the affected tissues and the consequent formation of Gaucher cells in the liver.

Efficacy of Formula (I) Hemitartrate in treating older Gaudier mice with pre-existing pathology. The efficacy of Formula (I) Hemitartrate at arresting or reversing disease progression in older, symptomatic Gaucher mice was also evaluated. Seven-month old D409V/null mice were administered 150 mg/kg/day Formula (I) Hemitartrate by oral gavage for 10 weeks. Analyses of glucosylceramide levels in the liver, lung and spleen of treated mice at 5 and 10 weeks post-treatment showed they had not increased beyond those observed at the start of the study. Alter 10 weeks of treatment, glucosylceramide levels were determined to be 60% lower in liver, 50% lower in lung and 40% lower in spleen than in vehicle-treated mice. These results showed that Formula (I) Hemitartrate was effective at inhibiting the further accumulation of glucosylceramide in mice with an existing burden of storage pathology.

Histopathological analysis of tissue sections showed a reduced number of Gaucher cells in the liver of treated D409V/null mice when compared to untreated controls. Quantitation of the number of Gaucher cells corroborated the biochemical findings; treated D409V/null mice displayed Gaucher cell counts that were not significantly different from those at the beginning of treatment at both the 5- and 10-week time points. Gaucher cell numbers at both these time points were significantly lower than those of untreated D409V/null mice. Together, these data demonstrate that Formula (I) Hemitartrate effectively inhibited further glucosylceramide accumulation and Gaucher cell development in animals with pre-existing pathology.

Discussion

Formula (I) Hemitartrate demonstrated a high degree of specificity for the enzyme glucosylceramide synthase. There was also no measurable inhibition of glucocerebrosidase activity at the effective dose, which is an important feature when treating Gaucher disease type 1 patients, the majority of whom retain residual glucocerebrosidase activity. At the effective dose of 150 mg/kg/day, there were no observable gastro-intestinal issues and there was no difference in body weights between the treated and control untreated groups. Serum concentrations at and above the $IC_{50}$ (24-40 nM) were readily attainable with oral doses that were below the maximum tolerated level. Formula (I) Hemitartrate also was readily metabolized and cleared: both parent compound and metabolites effectively cleared within 24 h as shown in single and repeat oral dose ADME studies with 14C-radio-labelled compound in rats and dogs.

Using a non-optimized dosing regimen of a single daily oral gavage successfully prevented glucosylceramide accumulation in both young, pre-symptomatic mice and in older Gaucher mice that already exhibited storage pathology. The young, 10-week old mice, although harboring elevated glucosylceramide levels relative to wild-type controls, had not yet developed the characteristic engorged tissue macrophages, termed Gaucher cells. Treatment with 150 mg/kg/day of Formula (I) Hemitartrate halted all measurable disease progression and inhibited the development of Gaucher cells. In older mice exhibiting a higher level of lysosomal glucosylceramide and number of Gaucher cells, there was no further increase in the levels of the glycosphingolipid or in the number of storage cells after either 5 weeks or 10 weeks of treatment. As the major source of glucosylceramide in Gaucher cells is reported to be extracellular in origin these results implied that Formula (I) Hemitartrate inhibition of glucosylceramide synthase was systemic.

The observation that Formula (I) Hemitartrate was effective in preventing further accumulation of glucosylceramide suggests a therapeutic strategy that could further enhance the treatment of Gaucher disease.

In summary, the data presented here demonstrated that Formula (I) Hemitartrate is an active and specific inhibitor of glucosylceramide synthase exhibiting no overt adverse effects in a mouse model of Gaucher disease. It successfully prevented disease progression in both pre-symptomatic and older diseased Gaucher mice by inhibiting glucosylceramide accumulation and Gaucher cell formation. These findings suggest that Formula (I) Hemitartrate may represent yet another therapeutic option for both pediatric and adult Gaucher type 1 disease and potentially other glycosphingolipid storage disorders.

Example 9

Phase 2 Clinical Trial of Formula (I) Hemitartrate

Methods. This clinical trial of Formula (I) Hemitartrate, given 50 or 100 mg bid orally, treated 26 adults with Gaucher disease type 1 (GD1) (16F:10M; mean age of 34 years, range 18-60; all Caucasian) at 7 sites in 5 countries. Patients were to have splenomegaly (volume 10 normal) and either thrombocytopenia (platelets 45,000-100,000/mm$^3$) or anemia (hemoglobin 8-10 g/dl, female; 8-11 g/dl, male). None received enzyme replacement or substrate reduction therapy in the prior 12 months. The composite primary efficacy endpoint is globin level (+0.5 g/dl) or platelet count (+15%) after 52 weeks of treatment. Liver volume, chitotriosidase, glucosylceramide are also assessed. Patients continue to be treated and monitored long-term.

Results. Week 52 data were available for up to 20 patients; 4 others withdrew prematurely and 2 were ongoing. The composite primary endpoint was met by 19 of the 20 patients. Mean (1 SD) changes from baseline to Week 52 were: hemoglobin +1.6 (11.35) g/dL; platelet count +43.6% (137.59%); spleen and liver volume (multiples of normal) 40.2% (110.44%) and 15.8% (110.39%), respectively; and chitotriosidase 49.9% (120.75%). Plasma glucosylceramide levels normalized after 4 weeks in all patients, Formula (I) Hemitartrate was well tolerated with an acceptable safety profile. Seven related adverse events in 6 patients have been reported as related; all were mild and transient in nature.

Example 10

Formula (I) Hemitartrate Pharmaceutical Composition, 100 mg Capsules

Method of Preparation of 100 mg Capsules: Formula (I) Hemitartrate, microcrystalline cellulose, lactose monohydrate, and hypromellose, EIS were separately passed through a 20 mesh screen. Amounts of the screened ingredients indicated in Table 9 were blended in a high-shear granulator for nine to twelve minutes.

TABLE 9

Pharmaceutical Formulation for 100 mg Capsules

| Ingredient | Unit Amount 100 mg Capsule (mg) | % per Unit Dose (% w/w) | Nominal Batch Size: 71,000 Capsules Total Quantity 19.2 kg |
|---|---|---|---|
| Formula (I) Hemitartrate | 100.0 | 37.0 | 7.1 |
| Microcrystalline cellulose | 45.0 | 16.7 | 3.2 |
| Lactose monohydrate | 111.5 | 41.3 | 7.9 |
| Hypromellose, E15 | 10.8 | 4.0 | 0.8 |
| Glyceryl behenate | 2.7 | 1.0 | 0.2 |
| Filled weight (mg) | 270 | | 248-292 mg |
| Total % composition | | 100.0 | 19.2 kg |

The ingredients were then wet granulated by the addition of purified water (2.2 kg; 11.7% of dry ingredients' weight) to the granulator bowl until completion, as visually confirmed. The wet granulation was discharged from the bowl and passed through a rotating impeller, screening mill. The wet granulation was then dried in a direct heating, static, solid, bed, tray dry oven at 50±5° C. to moisture content of not more than 3.5%, as confirmed by in-process check. The dry granules were then passed through a screening mill and the screened granules were transferred to a V-blender. Glyceryl behenate (0.2 kg) was added to the V-blender, and the final blend was mixed until the blend was uniform, as determined by an in-line or off-line blend uniformity test, typically for ten to twenty minutes. The final blend was then encapsulated in a #2-size capsule using a semi-automatic capsule filler to the appropriate fill weight (270 mg average), and the filled capsules were deducted before packaging.

Example 11A

Formula (I) Hemitartrate Pharmaceutical Composition, 10 mg Capsules

Method of Preparation 410 mg Capsules: The procedure of Example 10 was followed up to the encapsulation step. To produce a 10 mg capsule, the final blend was encapsulated in a #4 or #5-size capsule using a capsule filling machine to the appropriate fill weight (27 mg average), and the filled capsules were dedusted before packaging.

Example 11B

Formula (I) Hemitartrate Pharmaceutical Composition, 50 mg Capsules

Method of Preparation of 50 mg Capsules: The procedure of Example 10 was followed up to the encapsulation step. To produce a 50 mg capsule, the final blend was encapsulated in a #3-size capsule using a capsule filling machine to the appropriate fill weight (135 mg average), and the filled capsules were dedusted before packaging.

Example 11C

Formula (I) Hemitartrate Pharmaceutical Composition, 150 mg Capsules

Method of Preparation of 150 mg Capsules: The procedure of Example 10 was followed up to the encapsulation step. To produce a 150 mg capsule, the final blend was encapsulated in a #0-size capsule using a capsule filling machine to the appropriate fill weight (405 mg average), and the filled capsules were dedusted before packaging.

Example 12

Formula (I) Hemitartrate Pharmaceutical Composition, 25 mg Capsules

Method of Preparation of 25 mg Capsules: The procedure of Example 10 was followed up to the encapsulation step. To produce a 25 mg capsule, the final blend was encapsulated in a #4-size capsule using a capsule filling machine to the appropriate fill weight (67.5 mg average), and the filled capsules were dedusted before packaging.

Example 13

Formula (I) Hemitartrate Drug Interactions—CYP2D6 Inhibitors

A study was performed to evaluate the pharmacokinetics, safety and tolerability of multiple oral doses of Formula (I) Hemitartrate (100 mg BID) administered with and without paroxetine (30 mg once daily), a potent inhibitor of CYP2D6. This was an open-label, fixed-sequence study in 36 healthy subjects (17 males and 19 females). The secondary objectives were to evaluate the PK of paroxetine in combination with multiple doses of Formula (I) Hemitartrate (100 mg BID) in healthy subjects and to further evaluate Formula (I) Hemitartrate PK following multiple-dose compared with single-dose Formula (I) Hemitartrate administration.

The mean PK parameters of the free base of Formula (I) Hemitartrate as it exists in plasma were nonlinear and showed a 2-fold accumulation in AUC and $C_{max}$ with repeated administration (100 mg BID) as compared to single dose administration. Concomitant administration of Formula (I) Hemitartrate and paroxetine resulted in a 7-fold increase in $C_{max}$ and 9-fold increase in AUC as compared to the multiple-dose administration of Formula (I) Hemitartrate alone. These results indicate that paroxetine can inhibit the metabolism of Formula (I) Hemitartrate and increases blood plasma concentrations of the drug. Similar effects would be expected with other potent CYP2D6 inhibitors (e.g. fluoxetine and quinidine) and careful monitoring of drug plasma levels and potential dose adjustments are necessary when Formula (I) Hemitartrate is co-administered with a drug known to be a potent CYP2D6 inhibitor. Paroxetine concentrations were about 1.5- to 2-fold higher than expected which suggests that Formula (I) Hemitartrate or one of its metabolites may be a mild inhibitor of CYP2D6.

Example 14

Formula (I) Hemitartrate Drug Interactions—CYP3A4 Inhibitors and p-Glycoprotein (PGP) Inhibitors A study was performed to evaluate the pharmacokinetics, safety, and tolerability of multiple doses of Formula (I) Hemitartrate (100 mg twice daily) with and without multiple-dose ketoconazole (400 mg once daily) in healthy male and female subjects. This was an open-label fixed-sequence study in 36 healthy subjects (18 males and females) consisting of 3 periods which included 100-mg single-dose administration of Formula (I) Hemitartrate, multiple-dose administration of Formula (I) Hemitartrate, and concomitant administration of Formula (I) Hemitartrate 100 mg (twice daily) with ketoconazole 400 mg (once daily). Repeated administration of Formula (I) Hemitartrate and ketoconazole, a strong inhibitor of Cytochrome p450 3A4 ("CYP 3A4") and p-glycoprotein, resulted in a 4-fold increase in exposure of the free base of the Formula (I) Hemitartrate as it exists in plasma at steady state. Thus, patients already receiving Formula (I) Hemitartrate may require a temporary dose reduction while on concomitant therapy with strong inhibitors of CYP 3A4 or p-glycoprotein.

Example 15

Stability Studies for Formula (I) Hemitartrate Formulation

Blends were prepared by mixing Formula (I) Hemitartrate and excipients (Lactose Monohydrate capsulating grade, Avicel PH 301 (Microcrystalline cellulose) and Methocel E15 Prem LV (Hydroxypropylmethylcellulose) in a scintillation vial at about a two gram scale. 15.6% water was added to the blend and mixed to form wet granules. The wet granules were screened using a #10 sieve (opening of 2000 microns). The screened granules were then dried in an oven at 50° C. for 2 hours. The dried granules were screened using a #18 sieve (opening of 1000 microns). The lubricant, glyceryl behenate, was added to the blend and mixed to form the final blend. The blends prepared are shown in the table below:

TABLE

| Lot # | AP | Lactose Monohydrate | Avicel PH 101 | 50 mg/100 mg Formulation | Comment |
|---|---|---|---|---|---|
| 1 | 1 | 2.1 | 2.1 | 50 | control |
| 2 | 1 | 2.1 | 0 | 50 | without Avicel |
| 3 | 1 | 0 | 2.1 | 50 | without Lactose |
| 4 | 1 | 2.1 | 1.1 | 50 | less Avicel |
| 5 | 1 | 1.1 | 2.1 | 50 | less Lactose |
| 6 | 1 | 2.1 | 0.8 | 50 | Avicel and Lactose ratio comparable to 100 mg |
| 7 | 1 | 1.1 | 0.4 | 100 | control |

Methocel (HPMC) was used in the range of 2 to 4%
Compritol ATO 88 was used in the range of 1 to 1.6%

The seven formulation blends, which have different API:lactose:Avicel ratios, listed above were exposed to a high temperature at 85° C. for 3 days (a forced-degradation study condition) in order to understand the degradation rate and the stability of each formulation. This accelerated condition was chosen based on the study results that the extent of the degradation products of the 50 mg drug product at 24 months was similar to those obtained at 85° C. for 3 days.

The forced-degradation study was performed using a reverse phase gradient HPLC method which used a C18 column (Waters T3, 3 μm, 100×4.6 mm), mobile phases consisting of water and acetonitrile with 0.1% trifluoroacetic acid (TFA), UV detection at 280 nm, column temperature at 40° C., and flow rate at 2 mL/min. The gradient started at holding at 5% B (acetonitrile and 0.1% TFA) for 0.5 minutes, and then ramping up organic component at 4.83% B per minute up to 15 minutes.

The total degradants of each formulation blend was summed and plotted against the ratio of API:Lactose:Avicel and the results are shown in FIG. 15. The study results suggest that while keeping the API and Lactose ratio constant, decreasing the amount of avicel improves the stability of the formulation. When avicel is removed, the formulation has API:Lactose:Avicel ratio of 1:2.1:0, it is the most stable formulation. When the lactose is removed, the formulation has a API:Lactose:Avicel Ratio of 1:0:2.1, and this formulation is not the most unstable comparing to other ratios. The combined information suggests that lactose stabilizes the formulation, while avicel destabilizes the formulation. However, when both excipients are present, they interact with each other. The ratio most be adjusted to obtain a stable formulation.

For active pharmaceutical ingredients like Formula (I) hemihydrate that are water soluble, microcrystalline cellulose helps to form granules during wet granulation as it is insoluble in water. If microcrystalline cellulose was not used, a sharp change occurs from the granule stage to a paste form. The paste form was difficult to handle and the resulting particles after drying do not have the suitable mechanical strength and particle size distribution. The pharmaceutical composition that has 37 wt % of a Formula (I) Hemitartrate, 41.0 wt % of a water-soluble filler; 16.7 wt % of an insoluble filler, 2 wt % to about 6 wt % of a binder; and about 0.1 wt % to about 2 wt % of a lubricant, all on a dry solids basis has the best stability profile with respect to the amount of degradants formed.

The teachings of all patents, published applications and references cited herein are incorporated by reference in their entirety.

While this has been particularly shown and described with references to example embodiments thereof, it will be understood by those skilled in the art that various changes in form and details may be made therein without departing from the scope of the encompassed by the appended claims.

What is claimed is:

1. A hemitartrate salt of a compound represented by the following structural formula:

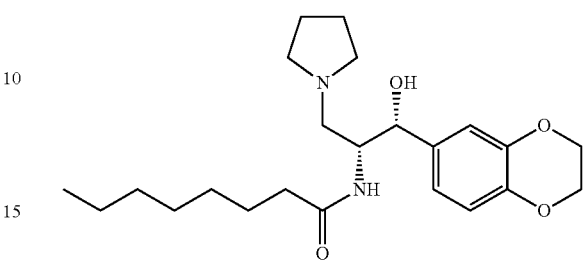

wherein the salt is in a crystalline form, the crystalline form characterized by at least two major X-ray powder diffraction peaks at 2θ angles selected from the group consisting of 5.1°, 6.6°, 10.7°, 11.0°, 15.9°, and 21.7°, wherein the specified 2θ angle means the specified value ±0.2°, and the X-ray powder diffraction diagram is obtained by using Cu K α radiation.

2. The hemitartrate salt of claim 1, wherein the hemitartrate salt is L-hemitartrate.

3. The hemitartrate salt of claim 1, wherein the crystalline form is characterized by major X-ray powder diffraction peaks at 2θ angles of 5.1°, 6.6°, 10.7°, 11.0°, 15.9°, and 21.7°, wherein the specified 2θ angle means the specified value±0.2°.

4. The hemitartrate salt of claim 1, wherein the crystalline form is characterized by X-ray powder diffraction peaks at 2 θ angles of 5.1°, 6.6°, 10.7°, 11.0°, 13.3°, 15.1°, 15.9°, 16.5°, 17.6°, 18.6°, 18.7°, 19.0°, 20.2°, 21.7°, and 23.5°, wherein the specified 2θ angle means the specified value±0.2°.

5. A pharmaceutical composition comprising the hemitartrate salt of claim 1, and a pharmaceutically acceptable carrier or diluent.

6. A pharmaceutical composition comprising:
the hemitartrate salt of claim 1;
at least one water-soluble filler;
at least one water-insoluble filler;
at least one binder; and
at least one lubricant.

7. The pharmaceutical composition of claim 6, wherein the at least one water-soluble filler is selected from the group consisting of anhydrous lactose, lactose monohydrate, mannitol, sodium chloride, powdered sugar, sorbitol, sucrose, inositol and pregelatinized starch; the at least one water-insoluble filler is selected from the group consisting of microcrystalline cellulose, calcium phosphate and starch; the at least one binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the at least one lubricant is selected from the group consisting of hydrogenated vegetable oil, calcium stearate, and glyceryl behenate.

8. The pharmaceutical composition of claim 7, wherein the composition comprises 14 wt % to 18 wt % of the at least one water-insoluble filler on a dry solids basis.

9. The pharmaceutical composition of claim 7, wherein the composition comprises 35 wt % to 40 wt % of the hemitartrate salt; 26 wt % to 50 wt % of lactose monohydrate; 8 wt % to 32 wt % of microcrystalline cellulose; 2 wt % to 6 wt % of hydroxypropyl methylcellulose; and 0.1 wt % to 2 wt % of glyceryl behenate, all on a dry solids basis.

10. A pharmaceutical composition comprising:
    the hemitartrate salt of claim 2;
    at least one water-soluble filler;
    at least one water-insoluble filler;
    at least one binder; and
    at least one lubricant.

11. The pharmaceutical composition of claim 10, wherein the at least one water-soluble filler is selected from the group consisting of anhydrous lactose, lactose monohydrate, mannitol, sodium chloride, powdered sugar, sorbitol, sucrose, inositol and pregelatinized starch; the at least one water-insoluble filler is selected from the group consisting of microcrystalline cellulose, calcium phosphate and starch; the at least one binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the at least one lubricant is selected from the group consisting of hydrogenated vegetable oil, calcium stearate, and glyceryl behenate.

12. The pharmaceutical composition of claim 10, wherein the composition comprises 14 wt % to 18 wt % of the at least one water-insoluble filler on a dry solids basis.

13. The pharmaceutical composition of claim 10, wherein the composition comprises 35 wt % to 40 wt % of the hemitartrate salt; 26 wt % to 50 wt % of lactose monohydrate; 8 wt % to 32 wt % of microcrystalline cellulose; 2 wt % to 6 wt % of hydroxypropyl methylcellulose; and 0.1 wt % to 2 wt % of glyceryl behenate, all on a dry solids basis.

14. A pharmaceutical composition comprising:
    the hemitartrate salt of claim 3;
    at least one water-soluble filler;
    at least one water-insoluble filler;
    at least one binder; and
    at least one lubricant.

15. The pharmaceutical composition of claim 14, wherein the at least one water-soluble filler is selected from the group consisting of anhydrous lactose, lactose monohydrate, mannitol, sodium chloride, powdered sugar, sorbitol, sucrose, inositol and pregelatinized starch; the at least one water-insoluble filler is selected from the group consisting of microcrystalline cellulose, calcium phosphate and starch; the at least one binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the at least one lubricant is selected from the group consisting of hydrogenated vegetable oil, calcium stearate, and glyceryl behenate.

16. The pharmaceutical composition of claim 14, wherein the composition comprises 14 wt % to 18 wt % of the at least one water-insoluble filler on a dry solids basis.

17. The pharmaceutical composition of claim 14, wherein the composition comprises 35 wt % to 40 wt % of the hemitartrate salt; 26 wt % to 50 wt % of lactose monohydrate; 8 wt % to 32 wt % of microcrystalline cellulose; 2 wt % to 6 wt % of hydroxypropyl methylcellulose; and 0.1 wt % to 2 wt % of glyceryl behenate, all on a dry solids basis.

18. A pharmaceutical composition comprising:
    the hemitartrate salt of claim 4;
    at least one water-soluble filler;
    at least one water-insoluble filler;
    at least one binder; and
    at least one lubricant.

19. The pharmaceutical composition of claim 18, wherein the at least one water-soluble filler is selected from the group consisting of anhydrous lactose, lactose monohydrate, mannitol, sodium chloride, powdered sugar, sorbitol, sucrose, inositol and pregelatinized starch; the at least one water-insoluble filler is selected from the group consisting of microcrystalline cellulose, calcium phosphate and starch; the at least one binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the at least one lubricant is selected from the group consisting of hydrogenated vegetable oil, calcium stearate, and glyceryl behenate.

20. The pharmaceutical composition of claim 18, wherein the composition comprises 14 wt % to 18 w t% of the at least one water-insoluble filler on a dry solids basis.

21. The pharmaceutical composition of claim 18, wherein the composition comprises 35 wt % to 40 wt % of the hemitartrate salt; 26 wt % to 50 wt % of lactose monohydrate; 8 wt % to 32 wt % of microcrystalline cellulose; 2 wt % to 6 wt % of hydroxypropyl methylcellulose; and 0.1 wt % to 2 wt % of glyceryl behenate, all on a dry solids basis.

22. A pharmaceutical composition comprising:
    the hemitartrate salt of claim 5;
    at least one water-soluble filler;
    at least one water-insoluble filler;
    at least one binder; and
    at least one lubricant.

23. The pharmaceutical composition of claim 22, wherein the at least one water-soluble filler is selected from the group consisting of anhydrous lactose, lactose monohydrate, mannitol, sodium chloride, powdered sugar, sorbitol, sucrose, inositol and pregelatinized starch; the at least one water-insoluble filler is selected from the group consisting of microcrystalline cellulose, calcium phosphate and starch; the at least one binder is selected from the group consisting of pre-gelatinized starch, sodium carboxymethyl cellulose, hydroxypropyl cellulose, hydroxypropyl methyl cellulose, polyvinyl pyrrolidone, copolyvidone, gelatin, natural gums, starch paste, sucrose, corn syrup, polyethylene glycols and sodium alginate; and the at least one lubricant is selected from the group consisting of hydrogenated vegetable oil, calcium stearate, and glyceryl behenate.

24. The pharmaceutical composition of claim 22, wherein the composition comprises 14 wt % to 18 wt % of the at least one water-insoluble filler on a dry solids basis.

25. The pharmaceutical composition of claim 22, wherein the composition comprises 35 wt % to 40 wt % of the hemitartrate salt; 26 wt % to 50 wt % of lactose monohydrate; 8 wt % to 32 wt% of microcrystalline cellulose; 2 wt % to 6 wt % of hydroxypropyl methylcellulose; and 0.1 wt % to 2 wt % of glyceryl behenate, all on a dry solids basis.

* * * * *